(12) United States Patent
Phillips et al.

(10) Patent No.: US 10,821,293 B2
(45) Date of Patent: Nov. 3, 2020

(54) SYSTEMS AND METHODS FOR NEURO-EEG SYNCHRONIZATION THERAPY

(71) Applicant: Wave Neuroscience, Inc., Newport Beach, CA (US)

(72) Inventors: James William Phillips, Fountain Valley, CA (US); Yi Jin, Irvine, CA (US)

(73) Assignee: Wave Neuroscience, Inc., Newport Beach, CA (US)

( * ) Notice: Subject to any disclaimer, the term of this patent is extended or adjusted under 35 U.S.C. 154(b) by 116 days.

(21) Appl. No.: 16/054,803

(22) Filed: Aug. 3, 2018

(65) Prior Publication Data

US 2019/0070428 A1 Mar. 7, 2019

Related U.S. Application Data

(60) Continuation of application No. 15/232,692, filed on Aug. 9, 2016, now Pat. No. 10,065,048, which is a
(Continued)

(51) Int. Cl.
*A61N 2/00* (2006.01)
*A61N 2/12* (2006.01)
(Continued)

(52) U.S. Cl.
CPC .............. *A61N 2/008* (2013.01); *A61B 5/048* (2013.01); *A61B 5/407* (2013.01); *A61B 5/4029* (2013.01);
(Continued)

(58) Field of Classification Search
CPC ..... A61B 5/4029; A61B 5/407; A61B 5/4076; A61B 5/7257; A61B 5/4035; A61B 5/048;
(Continued)

(56) References Cited

U.S. PATENT DOCUMENTS 3,821,949 A 7/1974 Hartzell et al.
4,727,857 A 3/1988 Hoerl
(Continued)

FOREIGN PATENT DOCUMENTS

DE 3417773 2/1985
DE 29821635 U1 7/1999
(Continued)

OTHER PUBLICATIONS

Angelakis et al., EEG Neurofeedback: A brief overview and an example of peak alpha frequency training for cognitive enhancement in the elderly, Clin. Neuropsychol., 21(1):110-29 (2007).
(Continued)

*Primary Examiner* — Christine H Matthews
*Assistant Examiner* — Joshua Daryl D Lannu
(74) *Attorney, Agent, or Firm* — Buchalter, a professional corp.; Kari L. Barnes

(57) ABSTRACT

Described are methods, devices, and systems for a novel, inexpensive, easy to use therapy for a number of disorders. Described are methods and devices to treat disorders that involves no medication. Methods and devices described herein use alternating magnetic fields to gently "tune" the brain and affect mood, focus, and cognition of subjects.

27 Claims, 35 Drawing Sheets

Related U.S. Application Data continuation of application No. 14/051,378, filed on Oct. 10, 2013, now Pat. No. 9,446,259, which is a division of application No. 12/942,922, filed on Nov. 9, 2010, now Pat. No. 8,585,568.

(60) Provisional application No. 61/260,779, filed on Nov. 12, 2009.

(51) Int. Cl.
*A61N 2/02* (2006.01)
*A61B 5/00* (2006.01)
*A61B 5/048* (2006.01)

(52) U.S. Cl.
CPC .......... *A61B 5/4035* (2013.01); *A61B 5/4076* (2013.01); *A61B 5/7257* (2013.01); *A61N 2/004* (2013.01); *A61N 2/02* (2013.01); *A61N 2/12* (2013.01); *A61B 2560/0468* (2013.01)

(58) Field of Classification Search
CPC . A61N 2/004; A61N 2/02; A61N 2/12; A61N 2/008
See application file for complete search history.

(56) References Cited

U.S. PATENT DOCUMENTS

| | | |
|---|---|---|
| 5,036,858 A | 8/1991 | Carter et al. |
| 5,092,835 A | 3/1992 | Schurig et al. |
| 5,409,445 A | 4/1995 | Rubins |
| 5,453,072 A | 9/1995 | Anninos et al. |
| 5,496,258 A | 3/1996 | Anninos et al. |
| 5,632,720 A | 5/1997 | Kleitz |
| 5,667,469 A | 9/1997 | Zhang et al. |
| 5,691,324 A | 11/1997 | Sandyk |
| 5,697,883 A | 12/1997 | Anninos et al. |
| 5,707,334 A | 1/1998 | Young |
| 5,769,778 A | 6/1998 | Abrams et al. |
| 5,788,624 A | 8/1998 | Lu et al. |
| 5,817,000 A | 10/1998 | Souder |
| 5,935,054 A | 8/1999 | Loos |
| 5,954,629 A | 9/1999 | Yanagidaira et al. |
| 6,001,055 A * | 12/1999 | Souder .................. A61N 2/008 600/9 |
| 6,083,252 A | 7/2000 | King et al. |
| 6,157,278 A | 12/2000 | Katznelson et al. |
| 6,194,852 B1 | 2/2001 | Lovatt et al. |
| 6,231,497 B1 | 5/2001 | Souder |
| 6,234,953 B1 | 5/2001 | Thomas et al. |
| 6,238,333 B1 | 5/2001 | Loos |
| 6,266,556 B1 | 7/2001 | Ives et al. |
| 6,290,638 B1 | 9/2001 | Canedo et al. |
| 6,402,678 B1 | 6/2002 | Fischell et al. |
| 6,463,328 B1 | 10/2002 | John |
| 6,488,617 B1 | 12/2002 | Katz |
| 6,537,197 B1 | 3/2003 | Ruohonen et al. |
| 6,648,812 B2 | 11/2003 | Ardizzone |
| 6,663,557 B2 | 12/2003 | Werny |
| 6,679,825 B2 | 1/2004 | Alicea |
| 6,978,179 B1 | 12/2005 | Flagg et al. |
| 7,033,312 B2 | 4/2006 | Rohan et al. |
| 7,102,144 B2 | 9/2006 | Matsuda et al. |
| 7,258,659 B2 | 8/2007 | Anninou et al. |
| 7,282,021 B2 | 10/2007 | Rohan et al. |
| 7,297,100 B2 | 11/2007 | Thomas et al. |
| 8,465,408 B2 | 6/2013 | Phillips et al. |
| 8,475,354 B2 | 7/2013 | Phillips et al. |
| 8,480,554 B2 | 7/2013 | Phillips et al. |
| 8,585,568 B2 | 11/2013 | Phillips et al. |
| 8,870,737 B2 | 10/2014 | Phillips et al. |
| 8,888,672 B2 | 11/2014 | Phillips et al. |
| 8,888,673 B2 | 11/2014 | Phillips et al. |
| 8,926,490 B2 | 1/2015 | Phillips et al. |
| 8,961,386 B2 | 2/2015 | Phillips et al. |
| 9,015,057 B2 | 4/2015 | Phillips et al. |
| 9,272,159 B2 | 3/2016 | Phillips et al. |
| 9,308,387 B2 | 4/2016 | Phillips et al. |
| 9,446,259 B2 | 9/2016 | Phillips et al. |
| 9,456,784 B2 | 10/2016 | Helekar et al. |
| 9,649,502 B2 | 5/2017 | Phillips et al. |
| 9,713,729 B2 | 7/2017 | Phillips et al. |
| 9,962,555 B1 | 5/2018 | Charles |
| 10,065,048 B2 | 9/2018 | Phillips |
| 2002/0007128 A1 | 1/2002 | Ives et al. |
| 2002/0147380 A1 | 10/2002 | Ardizzone |
| 2002/0153015 A1 | 10/2002 | Garibaldi et al. |
| 2002/0183587 A1 | 12/2002 | Dormer |
| 2003/0093028 A1 | 5/2003 | Spiegel |
| 2004/0138578 A1 | 7/2004 | Pineda et al. |
| 2004/0143296 A1 | 7/2004 | Wang et al. |
| 2004/0210102 A1 | 10/2004 | Van |
| 2005/0043774 A1 | 2/2005 | Devlin et al. |
| 2005/0070778 A1 | 3/2005 | Lackey et al. |
| 2005/0107654 A1 | 5/2005 | Riehl et al. |
| 2005/0107655 A1 | 5/2005 | Holzner |
| 2005/0118266 A1 | 6/2005 | Khan et al. |
| 2005/0118286 A1 | 6/2005 | Suffin et al. |
| 2005/0124847 A1 | 6/2005 | Ardizzone et al. |
| 2005/0124848 A1 | 6/2005 | Holzner |
| 2005/0154426 A1 | 7/2005 | Boveja et al. |
| 2005/0182287 A1 | 8/2005 | Becker |
| 2005/0187423 A1 | 8/2005 | Ardizzone et al. |
| 2005/0228209 A1 | 10/2005 | Schneider et al. |
| 2005/0256539 A1 | 11/2005 | George et al. |
| 2006/0015153 A1 | 1/2006 | Gliner et al. |
| 2006/0058572 A1 | 3/2006 | Anninou et al. |
| 2006/0094924 A1 | 5/2006 | Riehl et al. |
| 2006/0149119 A1 | 7/2006 | Wang |
| 2006/0161039 A1 | 7/2006 | Juliana et al. |
| 2006/0189866 A1 | 8/2006 | Thomas et al. |
| 2006/0212090 A1 | 9/2006 | Lozano et al. |
| 2006/0217781 A1 | 9/2006 | John et al. |
| 2006/0258950 A1 | 11/2006 | Hargrove et al. |
| 2006/0287566 A1 | 12/2006 | Zangen et al. |
| 2007/0004957 A1 | 1/2007 | Hilburg |
| 2007/0100389 A1 | 5/2007 | Jaax et al. |
| 2007/0106170 A1 | 5/2007 | Dunseath, Jr. et al. |
| 2007/0142874 A1 | 6/2007 | John et al. |
| 2007/0179558 A1 | 8/2007 | Gliner et al. |
| 2007/0191727 A1 | 8/2007 | Fadem |
| 2007/0203390 A1 | 8/2007 | Rohan et al. |
| 2007/0208209 A1 | 9/2007 | Holcomb |
| 2007/0282156 A1 | 12/2007 | Konings |
| 2008/0009772 A1 | 1/2008 | Tyler et al. |
| 2008/0046013 A1 | 2/2008 | Lozano |
| 2008/0081941 A1 | 4/2008 | Tononi |
| 2008/0125669 A1 | 5/2008 | Suffin et al. |
| 2008/0262287 A1 | 10/2008 | Dussau |
| 2009/0082690 A1 | 3/2009 | Phillips et al. |
| 2009/0198144 A1 | 8/2009 | Phillips et al. |
| 2009/0204015 A1 | 8/2009 | Phillips et al. |
| 2010/0185042 A1 | 7/2010 | Schneider et al. |
| 2011/0034822 A1 | 2/2011 | Phillips et al. |
| 2011/0112427 A1 | 5/2011 | Phillips et al. |
| 2011/0118536 A1 | 5/2011 | Phillips et al. |
| 2011/0137104 A1 | 6/2011 | Phillips et al. |
| 2013/0144108 A1 | 6/2013 | Phillips et al. |
| 2013/0150650 A1 | 6/2013 | Phillips et al. |
| 2014/0163305 A1 | 6/2014 | Watterson |
| 2014/0276182 A1 | 9/2014 | Helekar et al. |
| 2016/0045756 A1 | 2/2016 | James et al. |
| 2017/0120066 A1 | 5/2017 | Phillips et al. |
| 2017/0312536 A1 | 11/2017 | Phillips |
| 2018/0126184 A1 | 5/2018 | Phillips |
| 2018/0214710 A1 | 8/2018 | Charles |
| 2018/0229049 A1 | 8/2018 | Phillips |

FOREIGN PATENT DOCUMENTS

| | | |
|---|---|---|
| EP | 2197534 A1 | 6/2010 |
| EP | 2498857 A1 | 9/2012 |
| WO | WO-9615829 A2 | 5/1996 |
| WO | WO-9629114 A1 | 9/1996 |

(56) References Cited

FOREIGN PATENT DOCUMENTS

| | | |
|---|---|---|
| WO | WO-03058518 A2 | 7/2003 |
| WO | WO-2007067148 A1 | 6/2007 |
| WO | WO-2008074707 A1 | 6/2008 |
| WO | WO-2009036040 A1 | 3/2009 |
| WO | WO-2009042718 A1 | 4/2009 |
| WO | WO-2009042720 A1 | 4/2009 |
| WO | WO-2009042721 A1 | 4/2009 |
| WO | WO-2009042722 A1 | 4/2009 |
| WO | WO-2011017466 A1 | 2/2011 |
| WO | WO-2011059986 A1 | 5/2011 |
| WO | WO-2018136431 A1 | 7/2018 |

OTHER PUBLICATIONS

Anninos et al., "MEG evaluation of Parkinson's diseased patients after external magnetic stimulation," Acta neurol. Belg. 107:5-10, 2007.
Anninos et al., "Nonlinear Analysis of Brain Activity in Magnetic Influenced Parkinson Patients," Brain Topography 13(2):135-144, 2000.
Applied Signal Processing. (2004) 20 pgs., http://users.abo.fi/htoivone/courses/sbappl/asp_chapter1.pdf.
"Arns et al., Letter to the editor. Potential differential effects of 9 Hz rTMS and 10 Hz rTMS in the treatment of depression. Brain Stimulation, 3:124-126 (2010)".
Arns et al., "Potential differential effects of 9Hz rTMS and 10 Hz rTMS in the treatment of depression," Letter to the Editor, Brain Stimulation 3: 124-126, 2010.
Blum, Computer-based electroencephalography: technical basics, basis for new applications, and potential pitfalls, Electroencephalography and Clinical Neurophysiology 106, pp. 118-126, 1998.
Discovery Science: Transcranial Magnetic Stimulation Treatment for Addiction, Autism, Depression (Dr. Yi Jin) from PopSci's Future of Pleasure originally broadcast Oct. 26, 2009 [retrieved on Dec. 16, 2011, 4 pages] Retrieved from the Internet: http://www.youtube.com/watch?v=E3tPuB31CYc.
EP18160327.5 European Search Report dated Dec. 24, 2018.
European Patent Application No. 08833077 Supplementary Search Report and Written Opinon dated Dec. 21, 2010.
European Patent Application No. 08833077.4 Communication dated May 23, 2016.
European Patent Application No. 10830602.8 Communication dated Jun. 30, 2016.
First Annual Brain and Behavior Symposium: The Future of the Brain (Dr. Yi Jin) (Jun. 8, 2007) [retrieved on Dec. 16, 2011, 11 pages] Retrieved from the Internet: http://neurosciencecenter.brooksideinstitute.com/2007_symposium_03Speaker.asp.
Gasquet et al., "Pharmacological treatment and other predictors of treatment outcomes in previously untreated patients with schizophrenia; results from the European Schizophremia Outpatient Health Outcomes (SOHO) study," Int. Clin. Psychopharmacol. 20:199-205, 2005.
Gaussian Peak Fit VI., LabVIEW 2009 Help. National Instruments. 4 pgs., Jun. 2009.
Hamidi et al., "Repetitive transcranial magnetic stimulation affects behavior by biasing endogenous cortical oscillations," Frontiers in Integrative Neuroscience 3(14):1-12, 2009.
Japanese Patent Application No. 2017-8983 Office Action dated Nov. 27, 2017.
Jin, et al., "Therapeutic effects of individualized alpha frequency transcranial magnetic stimulation (alpha TMS) on the negative symptoms of schizophrenia," Schizophr. Bull. 32(3):556-561, 2006.
Jin, Y. et al., "Alpha EEG predicts visual reaction time," Int. J. Neurosci. 116:1035-1044, 2006.
Klimesch et al., "EEG alpha oscillations: The inhibition-timing hypothesis," Brain Research Reviews 53:63-88, 2003.
Klimesch et al., "Enhancing cognitive performance with repetitive transcranial magnetic stimulation at human individual alpha frequency," Eur. J. Neuroscience 17:1129-1133, 2003.
Leuchter, et al.The relationship between brain oscillatory activity and therapeutic effectiveness of transcranial magnetic stimulation in the treatment of major depressive disorder. Frontiers in Human Neuroscience. vol. 7, Article 37, pp. 1-12. Feb. 26, 2013.
MERT: Magno-EEG Resonant Therapy (Aug. 29, 2007) [retrieved on Dec. 19, 2011, 5 pages] Retrieved from the Internet: http://web.archive.org/web/20080514214345/http://neurosciencecenter.brooksideinstitute.com/mert.asp.
Myung, Tutorial on Maximum Likelihood Estimation, Journal of Mathematical Psychology, 47, pp. 90-100, 2003.
O'Haver, Curve Fitting C: Non-Linear Iterative Curve Fitting, 5 pages, Jun. 6, 2009. http://web.archive.org/web/20090606121639/http://terpconnect.umd.edu/~toh/spectrum/CurveFittingC.html.
PCT/US08/77569 International Preliminary Report on Patentability dated Mar. 30, 2010.
PCT/US08/77569 International Search Report dated Jan. 26, 2009.
PCT/US08/77569 International Written Opinion dated Jan. 26, 2009.
PCT/US08/77571 International Preliminary Report on Patentability dated Mar. 30, 2010.
PCT/US08/77571 International Search Report dated Nov. 21, 2008.
PCT/US08/77571 International Written Opinion dated Nov. 21, 2008.
PCT/US08/77573 International Preliminary Report on Patentability dated Mar. 30, 2010.
PCT/US08/77573 International Search Report dated Nov. 24, 2008.
PCT/US08/77573 International Written Opinion dated Nov. 24, 2008.
PCT/US08/77575 International Preliminary Report on Patentability dated Mar. 30, 2010.
PCT/US08/77575 Search Report dated Dec. 9, 2008.
PCT/US10/056075 International Preliminary Report on Patentability dated May 24, 2012.
PCT/US10/056075 International Search Report and Written Opinion dated Mar. 14, 2011.
PCT/US10/44465 International Preliminary Report on Patentability dated Feb. 7, 2012.
PCT/US10/44465 International Search Report and Written Opinion dated Sep. 29, 2010.
PCT/US2018/13903 International Search Report and Written Opinion dated May 15, 2018.
Real-Time Filtering in BioExplorer. 7 pages. Jan. 25, 2007. http://web.archive.org/web/20070125020332/http://www.brain-trainer.com/Filtering.pdf.
Sauseng et al., "Spontaneous locally restricted EEG alpha activity determines cortical excitability in the motor cortex," Neuropsychologia 47:284-288, 2009.
Triggs et al., Effects of Left Frontal Transcranial Magnetic Stimulation on Depressed Mood, Cognition, and Corticomotor Threshold, Society of Biological Psychiatry, 45:1440-1446, 1999.
U.S. Appl. No. 12/237,295 Office Action dated Dec. 6, 2011.
U.S. Appl. No. 12/237,295 Office Action dated May 23, 2014.
U.S. Appl. No. 12/237,295 Office Action dated May 9, 2011.
U.S. Appl. No. 12/237,295 Office Action dated Oct. 21, 2013.
U.S. Appl. No. 12/237,304 Office Action dated Feb. 12, 2015.
U.S. Appl. No. 12/237,304 Office Action dated Jan. 6, 2017.
U.S. Appl. No. 12/237,304 Office Action dated Jul. 3, 2012.
U.S. Appl. No. 12/237,304 Office Action dated Jul. 8, 2016.
U.S. Appl. No. 12/237,304 Office Action dated Oct. 10, 2017.
U.S. Appl. No. 12/237,304 Office Action dated Oct. 8, 2015.
U.S. Appl. No. 12/237,304 Office Action dated Sep. 25, 2013.
U.S. Appl. No. 12/237,319 Office Action dated Jul. 19, 2012.
U.S. Appl. No. 12/237,328 Office Action dated Oct. 12, 2011.
U.S. Appl. No. 12/850,547 Office Action dated Jul. 19, 2012.
U.S. Appl. No. 12/850,547 Office Action dated Oct. 13, 2011.
U.S. Appl. No. 12/942,922 Office Action dated Nov. 19, 2012.
U.S. Appl. No. 12/944,549 Office Action dated Mar. 25, 2014.
U.S. Appl. No. 12/944,549 Office Action dated Sep. 13, 2013.
U.S. Appl. No. 12/944,591 Office Action dated Apr. 7, 2014.
U.S. Appl. No. 12/944,591 Office Action dated Sep. 23, 2013.
U.S. Appl. No. 13/675,466 Office Action dated Aug. 1, 2014.
U.S. Appl. No. 13/675,466 Office Action dated Feb. 25, 2016.
"U.S. Appl. No. 13/675,466 Office Action dated Jul. 1, 2016".

(56) References Cited

OTHER PUBLICATIONS

U.S. Appl. No. 13/675,466 Office Action dated Aug. 26, 2015.
U.S. Appl. No. 13/675,466 Office Action dated Mar. 26, 2015.
U.S. Appl. No. 13/681,964 Office Action dated Jan. 22, 2014.
U.S. Appl. No. 13/682,057 Office Action dated Jan. 22, 2014.
U.S. Appl. No. 13/682,057 Office Action dated Jul. 11, 2014.
U.S. Appl. No. 13/682,057 Office Action dated Mar. 12, 2015.
U.S. Appl. No. 13/682,057 Office Action dated Jun. 30, 2015.
U.S. Appl. No. 13/682,057 Office Action dated Nov. 5, 2014.
U.S. Appl. No. 13/682,098 Office Action dated Feb. 11, 2015.
U.S. Appl. No. 13/682,098 Office Action dated Jan. 24, 2014.
U.S. Appl. No. 13/682,098 Office Action dated Jun. 30, 2014.
U.S. Appl. No. 13/682,098 Office Action dated Aug. 14, 2015.
U.S. Appl. No. 13/682,147 Office Action dated Apr. 25, 2013.
U.S. Appl. No. 13/682,147 Office Action dated Dec. 20, 2013.
U.S. Appl. No. 13/682,181 Office Action dated Jun. 27, 2014.
U.S. Appl. No. 13/893,171 Office Action dated Aug. 29, 2014.
U.S. Appl. No. 13/893,171 Office Action dated Jan. 2, 2015.
U.S. Appl. No. 13/893,171 Office Action dated Nov. 28, 2016.
U.S. Appl. No. 14/051,378 Office Action dated Jan. 5, 2015.
U.S. Appl. No. 14/051,378 Office Action dated Jul. 30, 2015.
U.S. Appl. No. 14/051,378 Office Action dated Mar. 24, 2016.
U.S. Appl. No. 14/051,378 Office Action dated Nov. 19, 2015.
U.S. Appl. No. 14/827,107 Office Action dated Aug. 31, 2018.
U.S. Appl. No. 15/232,692 Office Action dated Dec. 14, 2017.
U.S. Appl. No. 15/634,351 Office Action dated Sep. 10, 2018.
U.S. Appl. No. 12/237,319 Office Action dated Oct. 14, 2011.
U.S. Appl. No. 12/237,328 Office Action dated Jul. 19, 2012.
U.S. Appl. No. No. 13/682,181 Office Action dated Feb. 12, 2014.
U.S. Appl. No. 15/583,802 Office Action dated Aug. 28, 2017.
What is TMS? (Jun. 8, 2011) [online][retrieved on Dec. 19, 2011] Retrieved from the Internet: http://web.archive.org/web/20101014023718/http://braintreatmentcenter.com/tms.html; and http://www.braintreatmentcenter.com/addiction.

* cited by examiner $$A(f) = Ge^{(-(f-s)^2/2d^2)}$$

$$H(X, A) = \sum_{f=s-1Hz}^{s+1Hz} |X(f) - A(f)|$$

| Energy | Low | High |
|---|---|---|
| Metabolism | Low | High |
| BOLD | Low | High |
| rCBF | Low | High |
| Alpha power | High | Low |
| Q factor | High | Low |
| MDD Indication? | Yes | No |

Figure 40

SYSTEMS AND METHODS FOR NEURO-EEG SYNCHRONIZATION THERAPY

RELATED APPLICATIONS

This application is a continuation of U.S. patent application Ser. No. 15/232,692, filed Aug. 9, 2016, now U.S. Pat. No. 10,065,048, which is a Continuation of U.S. patent application Ser. No. 14/051,378, filed Oct. 10, 2013, now U.S. Pat. No. 9,446,259, which is a divisional of U.S. patent application Ser. No. 12/942,922, filed Nov. 9, 2010, now U.S. Pat. No. 8,585,568, which claims the benefit of U.S. Provisional Patent Application No. 61/260,779, filed Nov. 12, 2009, the content of each of which are incorporated herein by reference in their entirety.

BACKGROUND OF THE INVENTION

Mental disorders generate serious problems for the affected people, their families, and society. Currently, psychiatrists and neurophysiologists treat these disorders with a variety of medications, many of which have significant negative side effects.

Repetitive Transcranial Magnetic Stimulation (rTMS) uses an electromagnet placed on the scalp that generates a series of magnetic field pulses roughly the strength of an MRI scan. Some studies have shown that rTMS can reduce the negative symptoms of schizophrenia and depression under certain circumstances. To generate low frequency magnetic field pulses using an electromagnet such as in rTMS requires high current. Over time, this high current results in significant heat that must be actively dissipated.

SUMMARY OF THE INVENTION

Described are methods and systems for novel, inexpensive, easy to use therapy for a number of mental disorders. Described are methods and devices to treat mental disorders that involve no medication. Methods and devices described herein gently "tune" the brain and affect mood, focus, and cognition of human subjects. Methods and devices described herein gently "tune" the brain and affect mood, focus, and cognition of subjects.

In one aspect are methods of treating a subject, comprising: (a) adjusting output of a magnetic field for influencing an intrinsic frequency of a specified EEG band of the subject toward a pre-selected or target intrinsic frequency of the specified EEG band; and (b) applying said magnetic field close to a head of the subject.

Provided herein are methods of treating a subject, comprising determining the intrinsic frequency (f) of the subject within the specified EEG band by: obtaining EEG data of the subject's brain; removing any DC component in the signal; performing a Fast Fourier Transformation, X(f), on the EEG data; and achieving a fitted Gaussian curve, A(f), of the EEG data by: using the equation $A(f)=Ge^{(-f-s)^2/2d^2}$ (also depicted in FIG. 34), wherein G is gain, d is standard deviation, and s is the mean frequency based on the specified EEG band, and determining a goodness of fit measure by optimizing using the following equation $$H(X, A) = \sum_{f=s-1Hz}^{s+1Hz} |X(f) - A(f)|$$

(also depicted in FIG. 35), by: estimating a first mean frequency, a first standard of deviation, and first gain for the first optimizing loop, shifting the gain, G, up or down slightly from the first gain, determining a new gain resulting in a better fit than that of the first gain, shifting the standard of deviation, d, up or down slightly from the first standard of deviation, determining a new standard of deviation resulting in a better fit than that of the first standard of deviation, shifting the mean frequency, s, up or down slightly from the first mean frequency, determining a new mean frequency resulting in a better fit than that of the first mean frequency, and repeating steps 2), 3), and 4), in which the first gain, the first standard of deviation, and the first mean frequency are replaced with a second gain, a second standard of deviation, and a second mean frequency, respectively, until the three parameters are optimized, comparing the intrinsic frequency from step (a) to an average intrinsic frequency of a healthy population database; if the intrinsic frequency from step (a) is higher than the average intrinsic frequency of the healthy population database, shifting down the intrinsic frequency of the subject by applying a magnetic field close to a head of the subject, wherein said magnetic field has a frequency lower than the intrinsic frequency of the subject; and if the intrinsic frequency from step (a) is lower than the average intrinsic frequency of the healthy population database, shifting up the intrinsic frequency of the subject by applying a magnetic field close to a head of the subject, wherein said magnetic field has a frequency higher than the intrinsic frequency of the subject.

Provided herein is a method of using a Transcranial Magnetic Stimulation (TMS) device for influencing an intrinsic frequency of a subject within a specified EEG band, comprising: adjusting output of said TMS device; changing EEG frequency, Q-factor, or coherence by repetitive firing of a magnetic field using said TMS device; and applying said magnetic field close to a head of the subject, wherein the intrinsic frequency of the subject within the specified EEG band is determined by: obtaining EEG data of the subject's brain; removing any DC component in the signal; performing a Fast Fourier Transformation, X(f), on the EEG data; and achieving a fitted Gaussian curve, A(f), of the EEG data by: using the equation $A(f)=Ge^{(-f-s)^2/2d^2}$ (also depicted in FIG. 34), wherein G is gain, d is standard deviation, and s is the mean frequency based on the specified EEG band, and determining a goodness of fit measure by optimizing using the following equation $$H(X, A) = \sum_{f=s-1Hz}^{s+1Hz} |X(f) - A(f)|$$

(also depicted in FIG. 35), by: estimating a first mean frequency, a first standard of deviation, and first gain for the first optimizing loop, shifting the gain, G, up or down slightly from the first gain, determining a new gain resulting in a better fit than that of the first gain, shifting the standard of deviation, d, up or down slightly from the first standard of deviation, determining a new standard of deviation resulting in a better fit than that of the first standard of deviation, shifting the mean frequency, s, up or down slightly from the first mean frequency, determining a new mean frequency resulting in a better fit than that of the first mean frequency, and repeating steps 2), 3), and 4), in which the first gain, the first standard of deviation, and the first mean frequency are replaced with a second gain, a second standard of deviation, and a second mean frequency, respectively, until the three parameters are optimized.

In some embodiments, the method comprises the step of measuring EEG data of the subject after the applying step. In some embodiments, the method comprises the steps of: adjusting frequency of said magnetic field based on the EEG data of the subject; and repeating the applying step with an adjusted frequency. In some embodiments, applying of the magnetic field applies the magnetic field to a diffuse area in a brain of the subject. In some embodiments, the magnetic field is generated by movement of at least one permanent magnet. In some embodiments, said movement comprises at least one of rotational motion, linear motion, and swing motion. In some embodiments, a frequency of the magnetic field with the specified EEG band is from about 0.5 Hz to about 100 Hz. In some embodiments, the strength of the at least one permanent magnet is from about 10 Gauss to about 4 Tesla. In some embodiments, the distance between the at least one permanent magnet and the subject is from about 1/32 in to about 12 in. In some embodiments, the step of applying the magnetic field is for about 5 minutes to about two hours. In some embodiments, the method comprises repeating the applying step after an interval about 6 hours to about 14 days.

In some embodiments, the magnetic field is generated by a Transcranial Magnetic Stimulation device which generates the magnetic field using an electromagnetic coil.

In some embodiments, a frequency of the magnetic field with the specified EEG band is from about 0.5 Hz to about 100 Hz.

In some embodiments, the method comprises: (a) locating a first electrode operable to detect electrical brain activity on the subject in at least one of an area of low electrical resistivity on a subject, and an area with substantially no electrical impulse interference on a subject; (b) locating a second electrode operable to detect a reference signal on the subject; and (c) determining the intrinsic frequency from the electrical brain activity detected by the first electrode and the reference signal detected by the second electrode.

In some embodiments, the method improves an indication selected from the group consisting of replacement for meditation, quick nap, stress release, attention span, comprehension, memory, lowered blood pressure, increased libido, sports performance, academic performance, increased blood flow, lowered blood flow, increased metabolism, lowered metabolism, and any combination thereof. In some embodiments, the method is adapted to improve any of these indications.

In some embodiments, the method improves a disorder selected from the group consisting of depression, bipolar, anxiety, obsessive-compulsive, seizure, Parkinson's disease, ADHD, autism, substance abuse, head injury, Alzheimer's disease, eating disorder, sleep disorder, tinnitus, fibromyalgia, and any combination thereof. In some embodiments, the method is adapted to improve any of these disorders. In some embodiments fibromyalgia is considered a musculoskeletal disease and/or a neuropsychiatric condition. In some embodiments fibromyalgia is not a neurological disorder.

In some embodiments, the method is adapted to improve neuropathic pain, wherein the neuropathic pain comprises at least one of: occipital neuralgia, neuritis, trigeminal neuralgia, peripheral neuralgia, sciatic neuralgia, intercostal neuralgia, postherpetic neuralgia, diabetic neuropathy, and glossopharyngeal neuralgia.

In some embodiments, the method is adapted to improve a neurological disorder, wherein the neurological disorder comprises at least one of: a brain neurological disorder, a spinal cord disorder, a peripheral nervous system disorder, a cranial nerve disorder, an autonomic nervous system disorder, a seizure disorder, a movement disorder, a sleep disorder, a headache, lower back pain, neck pain, other generalized neuropathic pain, delirium, dementia, dizziness, vertigo, stupor, coma, a head injury, a stroke, multiple sclerosis, a demylenating disease, an infection of the brain or spinal cord, a prion disease, and a complex regional pain syndrome.

In some embodiments, the method is adapted to improve a symptom of brain damage, wherein the brain damage comprises at least one of: cerebral lobe damage including lower brain areas such as the basal ganglia, the cerebellum, and the brainstem; frontal lobe damage, parietal lobe damage, temporal lobe damage, and occipital lobe damage.

In some embodiments, the method is adapted to improve brain dysfunction, wherein the brain dysfunction comprises at least one of: aphasia, dysarthria, apraxia, agnosia, and amnesia.

In some embodiments, the method improves a characteristic selected from the group consisting of peripheral visual response, attention span, immediate reaction time (IRT), movement time (MT), simple perceptual reaction time (SPR), conflict perceptual reaction time (CPR), and any combination thereof. In some embodiments, the method is adapted to improve any of these characteristics.

In some embodiments, the magnetic field results from a first magnetic source and a second magnetic source. In some embodiments, the first magnetic source and the second magnetic source are out of phase relative to each other.

In some embodiments, the EEG band is the alpha band, and the mean frequency ranges from about 8 Hz to about 13 Hz.

In some embodiments, removing the DC component of the signal comprises filtering the EEG data with a 10th order 3 Hz high-pass IIR filter. In some embodiments, removing the DC component of the signal comprises filtering the EEG data twice with a 10th order 3 Hz high-pass IIR filter.

In some embodiments, the EEG data comprises about 30 seconds worth of EEG data at about 256 samples per second.

In some embodiments, the first gain is about one fourth (¼) of the peak value of a peak value of the Fast Fourier Transformation of the EEG data.

In some embodiments, a second optimization is performed having a first gain of at least about 1.5 times the peak value of the Fast Fourier Transformation of the EEG data.

In some embodiments, at least one of the intrinsic frequency and the fitted Gaussian curve is used to determine a Q factor of the intrinsic frequency within the specified EEG band of the subject.

In some embodiments, at least one of the intrinsic frequency and the fitted Gaussian curve is used to determine a coherence value of intrinsic frequencies among multiple sites in the brain of a subject within a specified EEG band.

In some embodiments, at least one of the intrinsic frequency and the fitted Gaussian curve is used to determine an EEG phase between two sites in the brain of a subject of a specified EEG frequency.

In some embodiments, shifting the standard of deviation comprises a shift from the first standard deviation of at least one of about 0.005, about 0.01, about 0.02, about 0.05, about 0.1, about 0.2, about 0.5, about 0.6, about 0.7, about 0.75, about 0.8, about 0.9, about 1.0, about 1.1, about 1.2, about 1.5, about 1.75, about 2.0, and about 2.5. As used herein, the term "about" when used in reference to standard deviation can mean variations of 1%, 10%, 20%, 25%, 50%, 1%-5%, 1%-10%, 5% to 10%, 10% to 20%, 10% to 50%, 10% to 25%, and/or 25% to 50%.

In some embodiments, shifting the gain comprises a shift from the first gain of at least one of about 0.005, about 0.01, about 0.02, about 0.05, about 0.1, about 0.2, about 0.5, about 0.6, about 0.7, about 0.75, about 0.8, about 0.9, about 1.0, about 1.1, about 1.2, about 1.5, about 1.75, about 2.0, and about 2.5. As used herein, the term "about" when used in reference to gain can mean variations of 1%, 10%, 20%, 25%, 50%, 1%-5%, 1%-10%, 5% to 10%, 10% to 20%, 10% to 50%, 10% to 25%, and/or 25% to 50%.

In some embodiments, shifting the mean frequency comprises a shift from the first mean frequency of at least one of about 0.005, about 0.01, about 0.02, about 0.05, about 0.1, about 0.2, about 0.5, about 0.6, about 0.7, about 0.75, about 0.8, about 0.9, about 1.0, about 1.1, about 1.2, about 1.5, about 1.75, about 2.0, and about 2.5. As used herein, the term "about" when used in reference to mean frequency can mean variations of 1%, 10%, 20%, 25%, 50%, 1%-5%, 1%-10%, 5% to 10%, 10% to 20%, 10% to 50%, 10% to 25%, and/or 25% to 50%.

Provided herein is a device comprising: at least one permanent magnet, a subunit coupled to the magnet, wherein the subunit enables movement of said at least one permanent magnet at a frequency between about 0.5 Hz and about 100 Hz, and logic that is operable to determine an intrinsic frequency (f) of a brain of a subject within a specified EEG band by: obtaining EEG data of the subject's brain; removing any DC component in the signal; performing a Fast Fourier Transformation, X(f), on the EEG data; achieving a fitted Gaussian curve, A(f), of the EEG data by: using the equation $A(f) = Ge^{(-f-s)^2/2d^2}$ (also depicted in FIG. 34), wherein G is gain, d is standard deviation, and s is the mean frequency based on the specified EEG band, and determining a goodness of fit measure by optimizing using the following equation $$H(X, A) = \sum_{f=s-1Hz}^{s+1Hz} |X(f) - A(f)|$$

(also depicted in FIG. 35), by: estimating a first mean frequency, a first standard of deviation, and first gain for the first optimizing loop, shifting the gain, G, up or down slightly from the first gain, determining a new gain resulting in a better fit than that of the first gain, shifting the standard of deviation, d, up or down slightly from the first standard of deviation, determining a new standard of deviation resulting in a better fit than that of the first standard of deviation, shifting the mean frequency, s, up or down slightly from the first mean frequency, determining a new mean frequency resulting in a better fit than that of the first mean frequency, and repeating steps 2), 3), and 4), in which the first gain, the first standard of deviation, and the first mean frequency are replaced with a second gain, a second standard of deviation, and a second mean frequency, respectively, until the three parameters are optimized.

In some embodiments, the device is operable to at least one of: influence the intrinsic frequency of the brain of a subject within the specified EEG band; influence a Q-factor of the intrinsic frequency; influence a coherence of intrinsic frequencies among multiple sites in the brain of a subject within a specified EEG band; and influence an EEG phase between two sites in the brain of a subject of a specified EEG frequency.

In some embodiments, a magnetic field is generated by movement of at least the permanent magnet. In some embodiments, said movement comprises at least one of rotational motion, linear motion, and swing motion.

In some embodiments, the device comprises logic that controls the frequency in increments of about 0.1 Hz.

In some embodiments, the device improves an indication selected from the group consisting of replacement for meditation, quick nap, stress release, attention span, comprehension, memory, lowered blood pressure, increased libido, sports performance, academic performance, increased blood flow, lowered blood flow, increased metabolism, lowered metabolism, and any combination thereof. In some embodiments, the device is adapted to improve any of these indications.

In some embodiments, the device improves a disorder selected from the group consisting of depression, bipolar, anxiety, obsessive-compulsive, seizure, Parkinson's disease, ADHD, autism, substance abuse, head injury, Alzheimer's disease, eating disorder, sleep disorder, tinnitus, fibromyalgia, and any combination thereof. In some embodiments, the device is adapted to improve any of these disorders. In some embodiments fibromyalgia is considered a musculoskeletal disease and/or a neuropsychiatric condition. In some embodiments fibromyalgia is not a neurological disorder.

In some embodiments, the device is adapted to improve neuropathic pain, wherein the neuropathic pain comprises at least one of: occipital neuralgia, neuritis, trigeminal neuralgia, peripheral neuralgia, sciatic neuralgia, intercostal neuralgia, postherpetic neuralgia, diabetic neuropathy, and glossopharyngeal neuralgia.

In some embodiments, the device is adapted to improve a neurologic disorder, wherein the neurologic disorder comprises at least one of: a brain neurological disorder, a spinal cord disorder, a peripheral nervous system disorder, a cranial nerve disorder, an autonomic nervous system disorder, a seizure disorder, a movement disorder, a sleep disorder, a headache, lower back pain, neck pain, other generalized neuropathic pain, delirium, dementia, dizziness, vertigo, stupor, coma, a head injury, a stroke, multiple sclerosis, a demylenating disease, an infection of the brain or spinal cord, a prion disease, and a complex regional pain syndrome.

In some embodiments, the device is adapted to improve a symptom of brain damage, wherein the brain damage comprises at least one of: cerebral lobe damage including lower brain areas such as the basal ganglia, the cerebellum, and the brainstem; frontal lobe damage, parietal lobe damage, temporal lobe damage, and occipital lobe damage.

In some embodiments, the device is adapted to improve brain dysfunction, wherein the brain dysfunction comprises at least one of: aphasia, dysarthria, apraxia, agnosia, and amnesia.

In some embodiments, the device improves a characteristic selected from the group consisting of peripheral visual response, attention span, immediate reaction time (IRT), movement time (MT), simple perceptual reaction time (SPR), conflict perceptual reaction time (CPR), and any combination thereof. In some embodiments, the device is adapted to improve any of these characteristics.

In some embodiments, shifting the standard of deviation comprises a shift from the first standard deviation of at least one of about 0.005, about 0.01, about 0.02, about 0.05, about 0.1, about 0.2, about 0.5, about 0.6, about 0.7, about 0.75, about 0.8, about 0.9, about 1.0, about 1.1, about 1.2, about 1.5, about 1.75, about 2.0, and about 2.5. As used herein, the term "about" when used in reference to standard deviation can mean variations of 1%, 10%, 20%, 25%, 50%, 1%-5%, 1%-10%, 5% to 10%, 10% to 20%, 10% to 50%, 10% to 25%, and/or 25% to 50%.

In some embodiments, shifting the gain comprises a shift from the first gain of at least one of about 0.005, about 0.01, about 0.02, about 0.05, about 0.1, about 0.2, about 0.5, about 0.6, about 0.7, about 0.75, about 0.8, about 0.9, about 1.0, about 1.1, about 1.2, about 1.5, about 1.75, about 2.0, and about 2.5. As used herein, the term "about" when used in reference to gain can mean variations of 1%, 10%, 20%, 25%, 50%, 1%-5%, 1%-10%, 5% to 10%, 10% to 20%, 10% to 50%, 10% to 25%, and/or 25% to 50%.

In some embodiments, shifting the mean frequency comprises a shift from the first mean frequency of at least one of about 0.005, about 0.01, about 0.02, about 0.05, about 0.1, about 0.2, about 0.5, about 0.6, about 0.7, about 0.75, about 0.8, about 0.9, about 1.0, about 1.1, about 1.2, about 1.5, about 1.75, about 2.0, and about 2.5. As used herein, the term "about" when used in reference to mean frequency can mean variations of 1%, 10%, 20%, 25%, 50%, 1%-5%, 1%-10%, 5% to 10%, 10% to 20%, 10% to 50%, 10% to 25%, and/or 25% to 50%.

Provided herein is a method comprising: adjusting output of a magnetic field for influencing at least one of an intrinsic frequency of a specified EEG band of a subject toward a pre-selected intrinsic frequency of the specified EEG band and a Q-factor of an intrinsic frequency within a specified EEG band of a subject toward a pre-selected Q-factor and applying said magnetic field close to a head of the subject; wherein at least one of the pre-selected intrinsic frequency and the pre-selected Q-factor is chosen in order to improve at least one of neuropathic pain in the subject, a neurological disorder in the subject, a symptom of brain damage, and brain dysfunction in the subject.

In some embodiments, the neuropathic pain comprises at least one of: occipital neuralgia, neuritis, trigeminal neuralgia, peripheral neuralgia, sciatic neuralgia, intercostal neuralgia, postherpetic neuralgia, diabetic neuropathy, and glossopharyngeal neuralgia.

In some embodiments, the neurological disorder comprises at least one of a brain neurological disorder, a spinal cord disorder, a peripheral nervous system disorder, a cranial nerve disorder, an autonomic nervous system disorder, a seizure disorder, a movement disorder, a sleep disorder, a headache, lower back pain, neck pain, other generalized neuropathic pain, delirium, dementia, dizziness, vertigo, stupor, coma, a head injury, a stroke, multiple sclerosis, a demylenating disease, an infection of the brain or spinal cord, a prion disease, and a complex regional pain syndrome.

In some embodiments, the brain damage comprises at least one of: cerebral lobe damage including lower brain areas such as the basal ganglia, the cerebellum, and the brainstem; frontal lobe damage, parietal lobe damage, temporal lobe damage, and occipital lobe damage.

In some embodiments, the brain dysfunction comprises at least one of: aphasia, dysarthria, apraxia, agnosia, and amnesia.

In some embodiments, the method comprises taking EEG measurements of the subject before the adjusting step or after the applying step, or both before the adjusting step and after the applying step. In some embodiments, the method comprises determining at least one of: the subject's intrinsic frequency of the specified EEG band and the subject's Q-factor of an intrinsic frequency within a specified EEG band. In some embodiments, the applying of the magnetic field applies the magnetic field to a diffuse area in a brain of the subject.

In some embodiments, the magnetic field is generated by movement of at least one permanent magnet. In some embodiments, the strength of the at least one permanent magnetic is from about 10 Gauss to about 4 Tesla. In some embodiments, the step of applying the magnetic field is for about 5 minutes to about two hours. In some embodiments, the method comprises repeating the applying step after an interval about 6 hours to about 14 days.

Provided herein is a device comprising: a means for adjusting output of a magnetic field for influencing at least one of: an intrinsic frequency of a specified EEG band of a subject toward a pre-selected intrinsic frequency of the specified EEG band; and a Q-factor of an intrinsic frequency within a specified EEG band of a subject toward a pre-selected Q-factor, wherein the means for adjusting the output of the magnetic field is adapted to apply said magnetic field close to a head of the subject, and wherein at least one of the pre-selected intrinsic frequency and the pre-selected Q-factor is chosen in order to improve at least one of: neuropathic pain in the subject, a neurological disorder in the subject, a symptom of brain damage, and brain dysfunction in the subject.

In some embodiments, the neuropathic pain comprises at least one of: occipital neuralgia, neuritis, trigeminal neuralgia, peripheral neuralgia, sciatic neuralgia, intercostal neuralgia, postherpetic neuralgia, diabetic neuropathy, and glossopharyngeal neuralgia.

In some embodiments, the neurological disorder comprises at least one of a brain neurological disorder, a spinal cord disorder, a peripheral nervous system disorder, a cranial nerve disorder, an autonomic nervous system disorder, a seizure disorder, a movement disorder, a sleep disorder, a headache, lower back pain, neck pain, other generalized neuropathic pain, delirium, dementia, dizziness, vertigo, stupor, coma, a head injury, a stroke, multiple sclerosis, a demylenating disease, an infection of the brain or spinal cord, a prion disease, and a complex regional pain syndrome.

In some embodiments, the brain damage comprises at least one of: cerebral lobe damage including lower brain areas such as the basal ganglia, the cerebellum, and the brainstem; frontal lobe damage, parietal lobe damage, temporal lobe damage, and occipital lobe damage.

In some embodiments, the brain dysfunction comprises at least one of: aphasia, dysarthria, apraxia, agnosia, and amnesia.

In some embodiments, the device comprises at least one permanent magnet. In some embodiments, the strength of the at least one permanent magnetic is from about 10 Gauss to about 4 Tesla.

In some embodiments, the device comprises an electromagnetic coil. In some embodiments, the electromagnetic coil emits field strengths of about 10 Gauss to about 4 Tesla.

In some embodiments, the magnetic field is generated by movement of at least one permanent magnet. In some embodiments, the movement of the at least one said magnet is at a frequency between about 0.5 Hz and about 100 Hz. In some embodiments, the movement comprises at least one of rotational motion, linear motion, and swing motion. In some embodiments, the movement generates an alternating magnetic field.

In some embodiments, the device comprises logic that controls a output of the magnetic field to be any frequency between about 0.5 Hz and about 100 Hz in increments of about 0.1 Hz.

Provided herein is a method for predicting efficacy of magnetic therapy in a subject comprising: providing EEG measurements for the subject; determining a subject's Q-factor in a specified EEG band; comparing the subject's Q-factor to a pre-selected Q-factor; if the subject's Q-factor is higher than the pre-selected Q-factor, providing a prediction that treatment with magnetic therapy that reduces the subject's Q-factor will improve at least one of: an indication in the subject, a disorder in the subject, a symptom in the subject, a dysfunction in the subject, and a characteristic in the subject. The EEG measurements are measurements of brain activity of the subject while at rest with eyes closed.

In some embodiments, the pre-selected Q-factor is at least one of: a Q-factor for a second subject who does not have the same indication, disorder, symptom, dysfunction and characteristic that the subject has; and a Q-factor for a healthy population of people not having the same indication, disorder, symptom, dysfunction and characteristic that the subject has, wherein the population comprises at least two people.

Provided herein is a method for predicting efficacy of magnetic therapy in a subject comprising: providing EEG measurements for the subject; determining a subject's alpha-frequency in a specified EEG band; comparing the subject's alpha-frequency to a pre-selected alpha-frequency; if the subject's alpha-frequency is lower than the pre-selected alpha-frequency, providing a prediction that treatment with magnetic therapy that raises the subject's alpha-frequency will improve at least one of: an indication in the subject, a disorder in the subject, a symptom in the subject, a dysfunction in the subject, and a characteristic in the subject. In some embodiments, the EEG measurements are measurements of brain activity of the subject while at rest with eyes closed.

In some embodiments, the pre-selected alpha-frequency is at least one of: an alpha-frequency for a second subject who does not have the same indication, disorder, symptom, dysfunction and characteristic that the subject has and an alpha-frequency for a healthy population of people not having the same indication, disorder, symptom, dysfunction and characteristic that the subject has, wherein the population comprises at least two people.

In some embodiments, the pre-selected alpha-frequency is about 9.0 Hz.

Provided herein is a method for predicting efficacy of magnetic therapy in a subject comprising: providing EEG measurements for the subject; determining if the subject's EEG measurements exhibit a double hump comprising a peak in the theta band and a peak in the alpha band; if the subject's theta band does not have a double hump, providing a prediction that treatment with magnetic therapy that reduces the subject's Q-factor and/or shifts the subject's alpha band frequency, will improve at least one of: an indication in the subject, a disorder in the subject, a symptom in the subject, a dysfunction in the subject, and a characteristic in the subject. In some embodiments, the EEG measurements are measurements of brain activity of the subject while at rest with eyes closed.

In some embodiments, the peak in the theta band exists when the subject's frequency domain EEG measurement has a peak that is at least about 10% higher than an affected population's theta band EEG measurement in the frequency domain, wherein the affected population comprises at least one person having the same indication, disorder, symptom, dysfunction and characteristic that the subject has.

In some embodiments, the peak in the theta band exists when the subject's frequency domain EEG measurement has a peak that is at least about 25% higher than an affected population's theta band EEG measurement in the frequency domain. In some embodiments, the peak in the theta band exists when the subject's frequency domain EEG measurement has a peak that is at least about 40% higher than an affected population's theta band EEG measurement in the frequency domain. In some embodiments, the peak in the theta band exists when the subject's frequency domain EEG measurement has a peak that is at least about 50% higher than an affected population's theta band EEG measurement in the frequency domain.

In some embodiments, the peak in the theta band exists when the subject's frequency domain EEG measurement has a peak that is at least about 10% higher than a normal population's theta band EEG measurement in the frequency domain, wherein the normal population comprises at least one person not having the same indication, disorder, symptom, dysfunction and characteristic that the subject has. In some embodiments, the peak in the theta band exists when the subject's frequency domain EEG measurement has a peak that is at least about 25% higher than a normal population's theta band EEG measurement in the frequency domain. In some embodiments, the peak in the theta band exists when the subject's frequency domain EEG measurement has a peak that is at least about 40% higher than a normal population's theta band EEG measurement in the frequency domain. In some embodiments, the peak in the theta band exists when the subject's frequency domain EEG measurement has a peak that is at least about 50% higher than a normal population's theta band EEG measurement in the frequency domain.

Provided herein is a method for predicting efficacy of magnetic therapy in a subject comprising: providing EEG measurements for the subject; determining if the subject's EEG measurements exhibit a high power beta band; if the subject's EEG measurements do not exhibit a high power beta band, providing a prediction that treatment with magnetic therapy that reduces the subject's Q-factor and/or shifts the subject's alpha band frequency, will improve at least one of: an indication in the subject, a disorder in the subject, a symptom in the subject, a dysfunction in the subject, and a characteristic in the subject. In some embodiments, the EEG measurements are measurements of brain activity of the subject while at rest with eyes closed.

In some embodiments, the subject's EEG measurements exhibit a high power beta band if the subject's beta band power is at least about 10% higher than an affected population's beta band power, wherein the affected population comprises at least one person having the same indication, disorder, symptom, dysfunction and characteristic that the subject has. In some embodiments, the subject's EEG measurements exhibit a high power beta band if the subject's beta band power is at least about 25% higher than an affected population's beta band power. In some embodiments, the subject's beta band power is at least about 40% higher than an affected population's beta band power. In some embodiments, the subject's beta band power is at least about 50% higher than an affected population's beta band power.

In some embodiments, the subject's EEG measurements exhibit a high power beta band if the subject's beta band power is at least about 10% higher than a normal population's beta band power, wherein the normal population comprises at least one person not having the same indication, disorder, symptom, dysfunction and characteristic that the subject has. In some embodiments, the subject's beta band power is at least about 25% higher than a normal population's beta band power. In some embodiments, the subject's beta band power is at least about 40% higher than a normal population's beta band power. In some embodiments, the subject's beta band power is at least about 50% higher than a normal population's beta band power.

In some embodiments, the indication comprises at least one of: replacement for meditation, quick nap, stress release, attention span, comprehension, memory, lowered blood pressure, increased libido, sports performance, academic performance, increased blood flow, lowered blood flow, increased metabolism, and a lowered metabolism.

In some embodiments, the disorder is depression.

In some embodiments, the disorder comprises at least one of: bipolar, anxiety, obsessive-compulsive, seizure, Parkinson's disease, ADHD, autism, substance abuse, head injury, Alzheimer's disease, eating disorder, sleep disorder, tinnitus, and fibromyalgia.

In some embodiments, the disorder is a neurologic disorder.

In some embodiments, the symptom is neuropathic pain.

In some embodiments, the symptom is psychogenic pain.

In some embodiments, the symptom is a brain damage symptom.

In some embodiments, the dysfunction is a brain dysfunction.

In some embodiments, the characteristic is at least one of: peripheral visual response, attention span, immediate reaction time (IRT), movement time (MT), simple perceptual reaction time (SPR), and conflict perceptual reaction time (CPR).

As used herein, providing the EEG measurements may or may not comprise generating EEG measurements, depending on the embodiment. In some embodiments, the EEG measurements may be generated at another time, and generating the EEG measurements is not part of the process claimed. In other embodiments, providing the EEG measurements comprises generating EEG measurements.

Provided herein is a device for predicting efficacy of magnetic therapy in a subject comprising: a receiving element that receives EEG measurements for the subject; logic that determines a subject's Q-factor in a specified EEG band; logic that compares the subject's Q-factor to a pre-selected Q-factor; and logic that, if the subject's Q-factor is higher than the pre-selected Q-factor, provides a prediction that treatment with magnetic therapy that reduces the subject's Q-factor will improve at least one of: an indication in the subject, a disorder in the subject, a symptom in the subject, a dysfunction in the subject, and a characteristic in the subject. In some embodiments, the EEG measurements are measurements of brain activity of the subject while at rest with eyes closed.

In some embodiments, the pre-selected Q-factor is at least one of: a Q-factor for a second subject who does not have the same indication, disorder, symptom, dysfunction and characteristic that the subject has, and a Q-factor for a healthy population of people not having the same indication, disorder, symptom, dysfunction and characteristic that the subject has, wherein the population comprises at least two people.

Provided herein is a device for predicting efficacy of magnetic therapy in a subject comprising: a receiving element that receives EEG measurements for the subject logic that determines a subject's alpha-frequency in a specified EEG band; logic that compares the subject's alpha-frequency to a pre-selected alpha-frequency; logic that, if the subject's alpha-frequency is lower than the pre-selected alpha-frequency, provides a prediction that treatment with magnetic therapy that raises the subject's alpha-frequency will improve at least one of: an indication in the subject, a disorder in the subject, a symptom in the subject, a dysfunction in the subject, and a characteristic in the subject. In some embodiments, the EEG measurements are measurements of brain activity of the subject while at rest with eyes closed.

In some embodiments, the pre-selected alpha-frequency is at least one of: an alpha-frequency for a second subject who does not have the same indication, disorder, symptom, dysfunction and characteristic that the subject has, and an alpha-frequency for a healthy population of people not having the same indication, disorder, symptom, dysfunction and characteristic that the subject has, wherein the population comprises at least two people.

In some embodiments, the pre-selected alpha-frequency is about 9.0 Hz.

Provided herein is a device for predicting efficacy of magnetic therapy in a subject comprising: a receiving element that receives EEG measurements for the subject; logic that determines if the subject's EEG measurements exhibit a double hump comprising a peak in the theta band and a peak in the alpha band; logic that, if the subject's theta band does not have a double hump, provides a prediction that treatment with magnetic therapy that reduces the subject's Q-factor and/or shifts the subject's alpha band frequency, will improve at least one of: an indication in the subject, a disorder in the subject, a symptom in the subject, a dysfunction in the subject, and a characteristic in the subject. In some embodiments, the EEG measurements are measurements of brain activity of the subject while at rest with eyes closed. In some embodiments, the peak in the theta band exists if, when the subject's frequency domain EEG measurement has a peak that is at least about 10% higher than an affected population's theta band EEG measurement in the frequency domain, wherein the affected population comprises at least one person having the same indication, disorder, symptom, dysfunction and characteristic that the subject has. In some embodiments, the peak in the theta band exists if, when the subject's frequency domain EEG measurement has a peak that is at least about 25% higher than an affected population's theta band EEG measurement in the frequency domain. In some embodiments, the peak in the theta band exists if, when the subject's frequency domain EEG measurement has a peak that is at least about 40% higher than an affected population's theta band EEG measurement in the frequency domain. In some embodiments, the peak in the theta band exists if, when the subject's frequency domain EEG measurement has a peak that is at least about 50% higher than an affected population's theta band EEG measurement in the frequency domain.

In some embodiments, the peak in the theta band exists when the subject's frequency domain EEG measurement has a peak that is at least about 10% higher than a normal population's theta band EEG measurement in the frequency domain, wherein the normal population comprises at least one person not having the same indication, disorder, symptom, dysfunction and characteristic that the subject has. In some embodiments, the peak in the theta band exists when the subject's frequency domain EEG measurement has a peak that is at least about 25% higher than a normal population's theta band EEG measurement in the frequency domain. In some embodiments, the peak in the theta band exists when the subject's frequency domain EEG measurement has a peak that is at least about 40% higher than a normal population's theta band EEG measurement in the frequency domain.

In some embodiments, the peak in the theta band exists when the subject's frequency domain EEG measurement has a peak that is at least about 50% higher than a normal population's theta band EEG measurement in the frequency domain.

Provided herein is a device for predicting efficacy of magnetic therapy in a subject comprising: a receiving element that receives EEG measurements for the subject; logic that determines if the subject's EEG measurements exhibit a high power beta band; logic that, if the subject's EEG measurements do not exhibit a high power beta band, provide a prediction that treatment with magnetic therapy that reduces the subject's Q-factor and/or shifts the subject's alpha band frequency, will improve at least one of: an indication in the subject, a disorder in the subject, a symptom in the subject, a dysfunction in the subject, and a characteristic in the subject. In some embodiments, the EEG measurements are measurements of brain activity of the subject while at rest with eyes closed. In some embodiments, the subject's EEG measurements exhibit a high power beta band if the subject's beta band power is at least about 10% higher than an affected population's beta band power, wherein the affected population comprises at least one person having the same indication, disorder, symptom, dysfunction and characteristic that the subject has. In some embodiments, the subject's beta band power is at least about 25% higher than an affected population's beta band power. In some embodiments, the subject's beta band power is at least about 40% higher than an affected population's beta band power. In some embodiments, the subject's beta band power is at least about 50% higher than an affected population's beta band power.

In some embodiments, the subject's EEG measurements exhibit a high power beta band if the subject's beta band power is at least about 10% higher than a normal population's beta band power, wherein the normal population comprises at least one person not having the same indication, disorder, symptom, dysfunction and characteristic that the subject has. In some embodiments, the subject's beta band power is at least about 25% higher than a normal population's beta band power. In some embodiments, the subject's beta band power is at least about 40% higher than a normal population's beta band power. In some embodiments, the subject's beta band power is at least about 50% higher than a normal population's beta band power.

In some embodiments, the indication comprises at least one of: replacement for meditation, quick nap, stress release, attention span, comprehension, memory, lowered blood pressure, increased libido, sports performance, academic performance, increased blood flow, lowered blood flow, increased metabolism, and a lowered metabolism.

In some embodiments, the disorder is depression.

In some embodiments, the disorder comprises at least one of: bipolar, anxiety, obsessive-compulsive, seizure, Parkinson's disease, ADHD, autism, substance abuse, head injury, Alzheimer's disease, eating disorder, sleep disorder, tinnitus, and fibromyalgia.

In some embodiments, the disorder is a neurologic disorder.

In some embodiments, the symptom is neuropathic pain.

In some embodiments, the symptom is psychogenic pain.

In some embodiments, the symptom is a brain damage symptom.

In some embodiments, the dysfunction is a brain dysfunction.

In some embodiments, the characteristic is at least one of: peripheral visual response, attention span, immediate reaction time (IRT), movement time (MT), simple perceptual reaction time (SPR), and conflict perceptual reaction time (CPR).

In some embodiments, the magnetic therapy is provided in the morning.

In some embodiments, the device for predicting efficacy of magnetic therapy is called an efficacy prediction device. In some embodiments, the efficacy prediction device is built into a magnetic therapy device, for non-limiting example, a NEST device.

As used herein, the EEG measurements may or may not be generated by a separate EEG device and downloaded from a saved format (e.g. a file saved in any manner which can be received and processed as described) or directly transferred without being otherwise saved from that separate EEG device, depending on the embodiment. In some embodiments, the EEG measurements may be generated by a separate device, an EEG device for example, and saved. In other embodiments, the EEG measurements may be generated by the efficacy prediction device itself and received by the receiving element within the efficacy prediction device.

In another aspect are methods of altering an intrinsic frequency of a brain of a subject within a specified EEG band, comprising: (a) determining the intrinsic frequency of the subject within the specified EEG band; (b) comparing the intrinsic frequency from step (a) to an average intrinsic frequency of a healthy population database; (c) if the intrinsic frequency from step (a) is higher than the average intrinsic frequency of the healthy population database, shifting down the intrinsic frequency of the subject by applying a specific magnetic field close to a head of the subject, wherein said specific magnetic field has a frequency lower than the intrinsic frequency of the subject; and (d) if the intrinsic frequency from step (a) is lower than the average intrinsic frequency of the healthy population database, shifting up the intrinsic frequency of the subject by applying a specific magnetic field close to a head of the subject, wherein said specific magnetic field has a frequency higher than the intrinsic frequency of the subject.

In another aspect are methods of treating a subject, comprising: (a) adjusting output of a magnetic field for influencing a Q-factor, a measure of frequency selectivity of a specified EEG band, of the subject toward a pre-selected or target Q-factor of the band; and (b) applying said magnetic field close to a head of the subject.

In another aspect are methods of treating a subject, comprising: determining the Q-factor of the intrinsic frequency within the specified EEG band of the subject; comparing the Q-factor of the intrinsic frequency from step (a) to an average Q-factor of the intrinsic frequency of a healthy population database; if the Q-factor of the intrinsic frequency from step (a) is higher than the average Q-factor of the intrinsic frequency of the healthy population database, tuning down the Q-factor of the intrinsic frequency of the subject by applying a magnetic field with a plurality of frequencies or with a single pre-selected frequency close to a head of the subject; and if the Q-factor of the intrinsic frequency from step (a) is lower than the average Q-factor of the intrinsic frequency of the healthy population database, tuning up the Q-factor of the intrinsic frequency of the subject by applying a magnetic field with a pre-selected frequency to a head of the subject.

In another aspect are methods of treating a subject, comprising: (a) adjusting output of a magnetic field for influencing a coherence of intrinsic frequencies among multiple sites in a brain of the subject within a specified EEG band toward a pre-selected or target coherence value; and (b) applying said magnetic field close to a head of the subject.

In another aspect are methods adjusting output of a magnetic field for influencing a coherence of intrinsic frequencies among multiple sites in a brain of the subject within a specified EEG band toward a pre-selected or target coherence value comprising: determining the coherence value of the intrinsic frequencies among multiple locations throughout a scalp of the subject; comparing the coherence value from step (a) to an average coherence value of a healthy population database; if the coherence value from step (a) is higher than the average coherence value of the healthy population database, lowering the coherence value of the subject by applying at least two asynchronous magnetic fields close to a head of the subject; if the coherence value from step (a) is lower than the average coherence value of the healthy population database, raising the coherence value of the subject by applying at least one synchronized magnetic field close to a head of the subject.

In another aspect are methods of using a Transcranial Magnetic Stimulation (TMS) device for influencing an intrinsic frequency of a subject within a specified EEG band, comprising: (a) adjusting output of said TMS device; (b) changing EEG frequency, Q-factor, or coherence by repetitive firing of a magnetic field using said TMS device; and (c) applying said magnetic field close to a head of the subject.

In another aspect are methods of treating anxiety in a subject, comprising tuning up the Q-factor of an intrinsic frequency of the subject by applying a magnetic field close to a head of the subject, wherein the magnetic field comprises at least one of (a) a single pre-selected frequency; (b) a plurality of frequencies within a specified EEG band; and (c) an intrinsic frequency of a brain of the subject within a specified EEG band. In some embodiments, any of the devices described herein may be used to treat anxiety.

In some embodiments, are method of treating depression in a subject, comprising tuning down the Q-factor of an intrinsic frequency of the subject by applying a magnetic field close to a head of the subject, wherein the magnetic field comprises at least one of (a) a single frequency; (b) a plurality of frequencies within a specified EEG band; and (c) an intrinsic frequency of a brain of the subject within a specified EEG band. In some embodiments, any of the devices described herein may be used to treat depression.

In another aspect are methods for treating a subject, comprising: (a) adjusting output of a magnetic field for influencing an EEG phase between two sites in the brain of a subject of a specified EEG frequency toward a pre-selected EEG phase of the specified EEG frequency; and (b) applying said magnetic field close to a head of the subject.

In some embodiments, the pre-selected EEG phase is lower than the EEG phase between the two sites in the brain of the subject. In some embodiments, the pre-selected EEG phase is any EEG phase lower than the EEG phase between the two sites in the brain of the subject. In some embodiments, the pre-selected EEG phase is higher than the EEG phase between the two sites in the brain of the subject. In some embodiments, the pre-selected EEG phase is any EEG phase higher than the EEG phase between the two sites in the brain of the subject. In some embodiments, the pre-selected EEG phase is an EEG phase of a population of people. The population of people may be a set of people having a particular trait, characteristic, ability, or feature. The population may be a healthy population of people. The population of people may be a set of people not having a particular disorder, such as anxiety, depression, or other disorders mentioned herein. In some embodiments, the methods comprise measuring EEG data of two sites in the brain of the subject, and calculating the EEG phase between the two sites in the brain of a subject. The specified EEG frequency may be an intrinsic frequency as described herein. The specified EEG frequency may be a pre-selected frequency as described herein. The pre-selected frequency may be an average intrinsic frequency of a healthy population database within a specified EEG band.

In another aspect are methods for influencing an EEG phase of a specified EEG frequency between multiple locations of a brain of a subject, comprising: (a) determining the EEG phase the between at least two locations measured on the head of the subject; (b) comparing the EEG phase from step (a) to an average EEG phase of a healthy population; and (c) applying a magnetic field close to a head of the subject wherein applying the magnetic field influences the determined EEG phase toward the average EEG phase of a healthy population.

In another aspect are methods for using a Transcranial Magnetic Stimulation (TMS) device for influencing an EEG phase of a subject of a specified EEG frequency, comprising: (a) adjusting output of said TMS device; (b) changing the EEG phase by repetitive firing of at least one magnetic field using said TMS device; and (c) applying said magnetic field close to a head of the subject.

In some embodiments, the magnetic field results from a first magnetic source and a second magnetic source. In some embodiments, the first magnetic source and the second magnetic source are out of phase relative to each other. In some embodiments, the amount that the first magnetic source and the second magnetic source are out of phase relative to each other is called the magnetic phase.

In some embodiments, the methods described are with the proviso that the methods are not used to treat schizophrenia.

In some embodiments of at least one aspect described above, the step of applying the magnetic field is for a pre-determined cumulative treatment time. In some embodiments of at least one aspect described above, the pre-selected or target intrinsic frequency with the specified EEG band is from about 0.5 Hz to about 100 Hz. In some embodiments of at least one aspect described above, the pre-selected or target intrinsic frequency with the specified EEG band is from about 1 Hz to about 100 Hz. In some embodiments of at least one aspect described above, the pre-selected or target intrinsic frequency with the specified EEG band is not greater than about 50 Hz. In some embodiments of at least one aspect described above, the pre-selected or target intrinsic frequency with the specified EEG band is not greater than about 30 Hz. In some embodiments of at least one aspect described above, the pre-selected or target intrinsic frequency with the specified EEG band is not greater than about 20 Hz. In some embodiments of at least one aspect described above, the pre-selected or target intrinsic frequency with the specified EEG band is not greater than about 10 Hz. In some embodiments of at least one aspect described above, the pre-selected or target intrinsic frequency with the specified EEG band is greater than about 3 Hz. In some embodiments of at least one aspect described above, the pre-selected or target intrinsic frequency with the specified EEG band is greater than about 1 Hz. In some embodiments, of at least one aspect described above, the pre-selected or target intrinsic frequency with the specified EEG band is up to about 25 Hz. As used herein, the term "about" when referring to a frequency can mean variations of 0.1 Hz to 0.2 Hz, 0.1 Hz to 0.5 Hz, 0.5 Hz to 1 Hz, or 1 Hz to 5 Hz. In some embodiments, applying of the magnetic field is to the motor cortex of the subject.

In some embodiments, the pre-selected and/or target intrinsic frequency is chosen from a plurality of intrinsic frequencies in the specified EEG band. In some embodiments the pre-selected and/or target intrinsic frequency is chosen from a plurality of intrinsic frequencies across a plurality of EEG bands. In some embodiments the specified EEG band is the Alpha band. In some embodiments the specified EEG band is the Beta band.

In some embodiments of at least one aspect described above, the methods further comprise the step of measuring EEG data of the subject before the applying step. In some embodiments of at least one aspect described above, said higher frequency is not greater than about 50 Hz. In some embodiments of at least one aspect described above, said higher frequency is not greater than about 30 Hz.

In some embodiments of at least one aspect described above, the varying frequencies (e.g. hopping frequencies) are moving average frequencies based on a pre-determined frequency around an intrinsic frequency within a predetermined frequency range. In some embodiments, the varying frequencies are randomly selected within a predetermined frequency range. In some embodiments of at least one aspect described above, the varying frequencies are moving average frequencies within a specified EEG band of a healthy population database. Those moving average frequencies can change from an initial frequency to a target frequency within a specific amount of time. In some embodiments of at least one aspect described above, the varying frequencies are frequencies hopping around within a pre-determined frequency range. In some embodiments of at least one aspect described above, the varying frequencies are frequencies hopping around an intrinsic frequency within a specified EEG band of a healthy population database. In some embodiments of at least one aspect described above, the pre-selected or target frequency is an average intrinsic frequency of a healthy population database within a specified EEG band. In some embodiments of at least one aspect described above, the pre-selected or target frequency is an intrinsic frequency of a brain of the subject within a specified EEG band.

In some embodiments of at least one aspect described above, the methods further comprise the step of measuring EEG data of the subject after the applying step. In some embodiments, further comprising the steps of:
adjusting frequency of said magnetic field based on the EEG data of the subject; and repeating the applying step with an adjusted frequency.

In some embodiments of at least one aspect described above, the applying of the magnetic field is continuous, in that it does not consist of discrete pulses separated by significant sections in which no magnetic field is applied. In some embodiments of at least one aspect described above, the magnetic field is continuously applied. A magnetic field that is continuously applied may alternate between a positive and negative field and include one or more neutral field(s), or alternate between a positive field and a neutral field, or alternate between a negative field and a neutral field, or some other combination of magnetic fields. It is continuous in the sense that it has a repetitive pattern (waveform) of charged fields (whether positive, negative, or a combination thereof) and uncharged fields. In some embodiments of at least one aspect described above, the applying of the magnetic field applies the magnetic field to a diffused area in a brain of the subject.

In some embodiments of at least one aspect described above, the magnetic field is generated by movement of at least one permanent magnet. In some embodiments, said movement comprises rotation of at least one said permanent magnet. In some embodiments, said movement comprises linear motion of at least one said permanent magnet. In some embodiments, said movement comprises curvilinear motion of at least one said permanent magnet. In some embodiments, said movement comprises at least one of rotational motion, linear motion, and swing motion. In some embodiments, the strength of the at least one permanent magnetic is from about 10 Gauss to about 4 Tesla. In some embodiments, the distance between the at least one permanent magnet and the subject is from about 0 inches to about 12 inches, from about 1/32 inches to about 12 inches, from about 1/16 inches to about 5 inches, or from about 1 inch to about 5 inches. As used herein, the term "about" when referring to distance between the at least one permanent magnet and the subject can mean variations of 1/64 inch, 1/32 inch, 1/16 inch, 1/8 inch, 1/4 inch, 1/3 inch, 1/2 inch, or 1 inch.

In some embodiments where the step of applying the magnetic field is for a pre-determined cumulative treatment time, said pre-determined cumulative treatment time is at least 5 min. In some embodiments where the step of applying the magnetic field is for a pre-determined cumulative treatment time, said pre-determined cumulative treatment time is from about 5 min to about two hours.

In some embodiments of at least one aspect described above, the methods further comprise repeating the applying step after an interval of treatment. In some embodiments, the interval of treatment is from about 6 hours to about 14 days.

In some embodiments of at least one aspect described above, the method improves an indication selected from the group consisting of replacement for meditation, quick nap, stress release, attention span, comprehension, memory, lowered blood pressure, increased libido, sports performance, academic performance, and any combination thereof. In some embodiments of at least one aspect described above, the method improves a mental disorder selected from the group consisting of depression, bipolar, anxiety, obsessive-compulsive, seizure, Parkinson's disease, ADHD, autism, substance abuse, head injury, Alzheimer's disease, eating disorder, sleep disorder, tinnitus, and any combination thereof. In some embodiments of at least one aspect described above, the method improves symptoms of fibromyalgia. In some embodiments of at least one aspect described above, the method halts the onset of a seizure. In some embodiments of at least one aspect described above, the method prevents the onset of a seizure. In some embodiments of at least one aspect described above, the method improves a characteristic selected from the group consisting of peripheral visual response, attention span, immediate reaction time (IRT), movement time (MT), simple perceptual reaction time (SPR), conflict perceptual reaction time (CPR), and any combination thereof. In some embodiments of at least one aspect described above, the method provides an improvement as measured using a rating scale selected from the group consisting of HAMA, HAMD, PANSS, MADRS, BARS, SAS, and any combination thereof. In some embodiments of at least one aspect described above, the method provides an improvement as measured using the Unified Parkinson's Rating Scale. In some embodiments of at least one aspect described above, the method provides an improvement as measured using a modified Unified Parkinson's Rating Scale. In some embodiments of at least one aspect described above, the method uses a Permanent Magneto-EEG Resonant Therapy (pMERT) device (alternatively called a Neuro-EEG Synchronization Therapy (NEST) device). In some embodiments of at least one aspect described above, the method uses a device as described herein. In some embodiments of at least one aspect described above, the method does not use a Transcranial Magnetic Stimulation (TMS) device.

In another aspect are devices comprising,
(a) at least one permanent magnet; and
(b) a subunit coupled to the magnet;
wherein the subunit enables movement of at least one said magnet at a frequency between about 0.5 Hz and about 100 Hz.

In another aspect are devices comprising,
(a) at least one permanent magnet; and
(b) a subunit coupled to the magnet;
wherein the subunit enables movement of at least one said magnet at a frequency between about 2 Hz and about 20 Hz.

In another aspect are devices comprising a means for applying a magnetic field to a head of a subject; whereby the means for applying the magnetic field is capable of influencing an intrinsic frequency of a brain of the subject within a specified EEG band.

In another aspect are devices comprising a means for applying a magnetic field to a head of a subject; whereby the means for applying the magnetic field is capable of influencing a Q-factor of an intrinsic frequency of a brain of the subject within a specified EEG band.

In another aspect are devices comprising a means for applying a magnetic field to a head of a subject; whereby the means for applying the magnetic field is capable of influencing a coherence of intrinsic frequencies among multiple sites in a brain of the subject within a specified EEG band.

In some embodiments of at least one aspect described above, the subunit comprises a rotating mechanism. In some embodiments, said rotating mechanism comprises:
(a) a motor;
(b) a power source capable of powering the motor; and
(c) a rotating element coupled to the motor and coupled to the magnet.

In some embodiments of at least one aspect described above, said device comprises at least one permanent magnet. In some embodiments of at least one aspect described above, the strength of the at least one permanent magnet is from about 10 Gauss to about 4 Tesla. In some embodiments of at least one aspect described above, the magnetic field is an alternating magnetic field.

In some embodiments of at least one aspect described above, the magnetic field is generated by movement of at least one permanent magnet. In some embodiments, the movement of the at least one said magnet is at a frequency between about 0.5 Hz and about 100 Hz. In some embodiments, the movement of the at least one said magnet is at a frequency between about 2 Hz and about 20 Hz.

In some embodiments of at least one aspect described above, said movement comprises rotation of at least one said permanent magnet. In some embodiments of at least one aspect described above, said movement comprises linear motion of at least one said permanent magnet. In some embodiments of at least one aspect described above, said movement comprises swing motion of at least one said permanent magnet. In some embodiments, said movement comprises at least one of rotational motion, linear motion, and swing motion.

In some embodiments of at least one aspect described above, said movement generates an alternating magnetic field. In some embodiments of at least one aspect described above, the magnetic field is continuously applied. In some embodiments of at least one aspect described above, the magnetic field covers a diffused area in a brain of a subject. In some embodiments of at least one aspect described above, the device is a Permanent Magneto-EEG Resonant Therapy (pMERT) device. In some embodiments of at least one aspect described above, the device is a Neuro-EEG Synchronization Therapy (NEST) device. As used herein, the terms Neuro-EEG Synchronization Therapy (NEST) device and Permanent Magneto-EEG Resonant Therapy (pMERT) device may be used interchangeably.

In some embodiments of at least one aspect described above, the devices further comprise logic that controls the frequency to be any frequency between about 2 and about 20 Hz in increments of about 0.1 Hz. In some embodiments of at least one aspect described above, the devices further comprise logic that controls the frequency to be any frequency between about 2 and about 50 Hz in increments of about 0.1 Hz. In some embodiments of at least one aspect described above, the devices further comprise logic that automatically changes the frequency in response to EEG readings of a subject before and/or during treatment. In some embodiments of at least one aspect described above, the devices further comprise logic that allows a user to set duration of a treatment before said treatment. In some embodiments, the user may be, for non-limiting example, a patient, a therapist, a psychiatrist, a psychologist, a neurologist, a family doctor, a general practitioner, a another medical professional, or a person treating a patient. In some embodiments, the user is not a patient.

In some embodiments of at least one aspect described above, the devices comprise a white noise generator.

In some embodiments, the devices further comprise a coupling to at least one of an internet line and a phone line. In some embodiments, at least a portion of the coupling to the internet line or to the phone line is wireless. The device may further comprise a smart card for storing and transferring information.

In some embodiments of at least one aspect described above, the devices further comprise logic that calculates information from EEG data collected from the subject within a specified EEG band,
wherein said information comprises at least one of items listed below:
(a) at least one intrinsic frequency;
(b) Q-factor of the at least one intrinsic frequency;
(c) a coherence value of intrinsic frequencies;
(d) an EEG phase; and
(e) any combination thereof.

In some embodiments, the devices further comprise logic that uploads said information through at least one of an internet line and a telephone line to an EEG data analysis service capable of storing said information. In some embodiments, said EEG data analysis service is capable of associating the said information with an identification associated with the subject.

In some embodiments of at least one aspect described above, the devices further comprise logic that uploads EEG data collected from the subject to an EEG data analysis service, wherein the EEG data analysis service is capable of validating information uploaded from the device, wherein said information comprises at least one of items listed below:

(a) at least one intrinsic frequency;
(b) Q-factor of the at least one intrinsic frequency;
(c) a coherence value of intrinsic frequencies;
(d) an EEG phase; and
(e) any combination thereof.

In some embodiments, said information comprises at least two of the listed items. In some embodiments of at least one aspect described above, further comprising logic that downloads a treatment dosage quota. In some embodiments, the treatment dosage quota is chosen by a user treating the subject based on a diagnosis of the subject. In some embodiments, the treatment dosage quota is chosen by a user who is charged for requesting a download of a cumulative treatment time based on a diagnosis of the subject. In some embodiments, the user is charged by a billing service before, during, or after the download of the dosage quota.

In some embodiments of at least one aspect described above, the devices further comprise logic that uploads a subject's EEG data through at least one of an internet line and a phone line to an EEG data analysis service. In some embodiments of at least one aspect described above, the devices further comprise logic that records usage information for using the device. In some embodiments, the device further comprises logic that ceases to deliver treatment after a treatment dosage quota is depleted. In some embodiments, the billing service is a vendor of the device. In some embodiments of at least one aspect described above, the devices further comprise logic that allows a user to establish a user account.

In some embodiments, the device comprises at least two permanent magnets. In some embodiments, the device comprises a helmet to be used for a subject's head. In some embodiments of at least one aspect described above, the device comprises a communication subunit for coupling to an internet line. In some embodiments of at least one aspect described above, the device comprises a communication subunit for coupling to a phone line. In some embodiments, the device comprises a memory subunit for storing information during a treatment.

In another aspect are methods for ordering a therapeutic dosage quota through internet, comprising,
(a) receiving a request from a user to access a user account through internet for ordering the therapeutic dosage quota;
(b) allowing the user to select at least one desired therapeutic dosage quota; and
(c) allowing the downloading of a therapeutic dosage quota into a device comprising a means for applying a magnetic field to a head of a subject.

The user may be allowed, in some embodiments, to download the therapeutic dosage quota. In some embodiment, the methods further comprise the step of establishing a user account based on a request from a user for ordering a therapeutic dosage quota.

In another aspect are methods for uploading EEG data associated with a subject through internet, comprising,
(a) creating a database for storing a user account associated with a user;
(b) storing the user account in the database,
(c) receiving a request from the user to access the user account;
(d) allowing said EEG data to be recorded into a device comprising a means for applying a magnetic field to a head of the subject;
(e) determining from said EEG data at least one of an intrinsic frequency within a specified EEG band, Q-factor of the intrinsic frequency, an EEG phase, and a coherence value of intrinsic frequencies; and
(f) allowing the uploading of at least one of the EEG data, the intrinsic frequency within a specified EEG band, the Q-factor of the intrinsic frequency, the EEG phase, the coherence value of intrinsic frequencies, and any combination thereof.

In some embodiments, allowing the user to upload may include allowing the user to move data from a device as described herein to a database. The method may comprise receiving a request from the user to access the user account through at least one of an internet line or a phone line for access to said database. The method may comprise allowing the user to upload at least one of an intrinsic frequency within a specified EEG band, Q-factor of the intrinsic frequency, an EEG phase, and a coherence value of intrinsic frequencies. The data may include at least one of the EEG data, an intrinsic frequency within a specified EEG band, Q-factor of the intrinsic frequency, a coherence value of intrinsic frequencies, or any combination thereof.

In some embodiments of at least one aspect described above, the device is any device as disclosed herein. In some embodiments of at least one aspect described above, the user account comprises:
(a) user information;
(b) user access information; and
(c) based on each subject and each therapeutic dosage quota administered to each subject, fields for storing at least one of
  (1) EEG data of the subject,
  (2) intrinsic frequency within a specified EEG band of the subject,
  (3) Q-factor of the intrinsic frequency of the subject
  (4) an EEG phase of a specified EEG frequency of the subject,
  (5) a coherence value of intrinsic frequencies of the subject,
  (6) treatment information of the subject, and
  (7) device usage information for the subject.

In some embodiments, the user information excludes identifying information (e.g. user names).

In some embodiments of at least one aspect described above, the methods further comprise the step of charging at least one of the user, the subject, and an insurance company associated with the subject a fee for use of the device based on the dosage quota ordered in at least one of the user account and the device.

In another aspect are methods for administration of treatment of subjects, comprising,
(a) storing data in a device of an individual subject during treatment using the device, wherein the device comprises a means for applying a magnetic field to a head of the subject;
(b) retrieving the data of said individual subject from said device; and
(c) updating a database for the subject with the data, through at least one of an internet line and a phone line.

In some embodiments, said data of said individual subject comprises at least one of EEG data of the subject, at least one intrinsic frequency within a specified EEG band of the subject, Q-factor of the intrinsic frequency of the subject, a coherence value of intrinsic frequencies of the subject, an EEG phase of a specified EEG frequency of the subject, treatment information of the subject, and device usage information for the subject. In some embodiments, the retrieving and updating steps occur upon the subject's visit to a psychiatrist, a therapist, a treatment provider, and/or another type of medical professional. In some embodiments, the retrieving and updating steps occur prior to a subject's visit to a psychiatrist, a therapist, a treatment provider, and/or another type of medical professional. In some embodiments, the retrieving and updating steps occur following a subject's visit to a psychiatrist, a therapist, a treatment provider, and/or another type of medical professional.

In some embodiments of at least one aspect described above, the methods or devices use a Transcranial Magnetic Stimulation (TMS) device.

Provided herein is a method comprising adjusting an output current of an electric alternating current source for influencing an intrinsic frequency of an EEG band of a subject toward a target frequency of the EEG band; and applying said output current across a head of the subject.

In some embodiments, the step of adjusting the output current comprises setting the output current to a frequency that is lower than the intrinsic frequency of the subject.

In some embodiments, the step of adjusting the output current comprises setting the output current to a frequency that is higher than the intrinsic frequency of the subject.

In some embodiments, the step of adjusting the output current comprises setting the output current to the target frequency.

Provided herein is a method comprising determining the intrinsic frequency of the EEG band of the subject; and comparing the intrinsic frequency to the target frequency of the EEG band, wherein the target frequency is an average intrinsic frequency of the EEG band of a healthy population of people, wherein if the intrinsic frequency is higher than the target frequency, the step of adjusting the output current comprises setting the output current to a frequency that is lower than the intrinsic frequency of the subject, and if the intrinsic frequency is lower than the target frequency, the step of adjusting the output current comprises setting the output current to a frequency that is higher than the intrinsic frequency of the subject.

Provided herein is a method comprising adjusting an output current of an electric alternating current source for influencing a Q-factor of an intrinsic frequency of an EEG band of a subject toward a target Q-factor; and applying said output current across a head of the subject.

In some embodiments, the step of adjusting the output current comprises varying a frequency of the output current.

In some embodiments, the step of adjusting the output current comprises setting the output current to a frequency that is higher than the intrinsic frequency of the subject.

In some embodiments, the step of adjusting the output current comprises setting the output current to a frequency that is lower than the intrinsic frequency of the subject.

In some embodiments, the step of adjusting the output current comprises setting the output current to the target frequency.

In some embodiments, the method further comprises determining the Q-factor of the intrinsic frequency of the EEG band of the subject; and comparing the Q-factor to the target Q-factor, wherein the target Q-factor is an average Q-factor of the intrinsic frequencies of the EEG band of a healthy population of people, wherein if the Q-factor of the intrinsic frequency is higher than the target Q-factor, the step of adjusting the output current comprises varying a frequency of the output current, and if the Q-factor of the intrinsic frequency is lower than the target Q-factor, the step of adjusting the output current comprises setting the output current to a frequency that is the intrinsic frequency of the subject.

In some embodiments, influencing an intrinsic frequency may include influencing harmonics of the pre-selected intrinsic frequency of the specified EEG band. In some embodiments, the pre-selected intrinsic frequency is a harmonic of the peak intrinsic frequency of a specified EEG band. In some embodiments, influencing the pre-selected intrinsic frequency includes applying harmonic frequencies of the pre-selected intrinsic frequency. In some embodiments, the varying frequencies comprise harmonic frequencies of a single frequency. The single frequency may comprise the pre-selected intrinsic frequency.

In some embodiments, a device as described herein is operable to influence an intrinsic frequency of the brain of a subject within a specified EEG band. A device as described herein may be operable to influence a Q-factor of an intrinsic frequency of the brain of a subject within a specified EEG band. A device as described herein may be operable to influence a coherence of intrinsic frequencies among multiple sites in the brain of a subject within a specified EEG band.

In some embodiments, a device as described herein further comprises a first electrode operable to detect electrical brain activity; and a second electrode operable to detect a reference signal, wherein the first electrode is located on the subject in at least one of: an area of low electrical resistivity on a subject, and an area with substantially no electrical impulse interference on a subject, and wherein the second electrode is located on the subject. In some embodiments, a device as described herein further comprises a first electrode operable to detect electrical brain activity; and a second electrode operable to detect a reference signal, wherein the first electrode is located on the subject in at least a portion of the ear canal of the subject, and wherein the second electrode is located on the subject.

In some embodiments of the methods described herein, the method or methods may comprise locating a first electrode operable to detect electrical brain activity on the subject in at least one of an area of low electrical resistivity on a subject and an area with substantially no electrical impulse interference on a subject. The method or methods may further comprise locating a second electrode operable to detect a reference signal on the subject. The method or methods may further comprise determining the intrinsic frequency from the electrical brain activity detected by the first electrode and the reference signal detected by the second electrode. In some embodiments, determining the intrinsic frequency may comprise removing the reference signal detected by the second electrode from the electrical brain activity detected by the first electrode. The method or methods may further comprise determining the Q-factor of an intrinsic frequency of the specified EEG band from the electrical brain activity detected by the first electrode and the reference signal detected by the second electrode. In some embodiments, determining the Q-factor of an intrinsic frequency of the specified EEG band comprises ascertaining the Q-factor from the electrical brain activity detected by the first electrode and the reference signal detected by the second electrode.

In some embodiments of the methods described herein, the method or methods may comprise locating a first electrode operable to detect electrical brain activity on the subject in at least a portion of the ear canal of the subject. The method or methods may further comprise locating a second electrode operable to detect a reference signal on the subject. The method or methods may further comprise determining the intrinsic frequency from the electrical brain activity detected by the first electrode and the reference signal detected by the second electrode.

In some embodiments, a device as described herein is operable to influence an EEG phase between two sites in the brain of a subject of a specified EEG frequency. The device may comprise a second permanent magnet, wherein the subunit is coupled to the second magnet, and wherein the subunit enables movement of the second magnet at a frequency between about 0.5 Hz and about 100 Hz. The subunit may enable movement of the second magnet at a frequency between about 2 Hz and about 20 Hz. The first permanent magnet may have a first rotational orientation relative to a treatment surface of the device and the second permanent magnet may have a second rotational orientation relative to the treatment surface of the device. The device may be operable to move the first permanent magnet at the same frequency as the second permanent magnet. The first rotational orientation relative to a first portion of a treatment surface of the device may be between at least about 0 degrees and about 360 degrees different from the second rotational orientation relative to a second portion of the treatment surface of the device. The first rotational orientation relative to a first portion of a treatment surface of the device may be at least one of: between at least about 0 degrees and about 180 degrees, between at least about 0 degrees and about 90 degrees, between at least about 0 degrees and about 45 degrees, between at least about 0 degrees and about 30 degrees, between at least about 0 degrees and about 15 degrees, between at least about 0 degrees and about 10 degrees, at least about 5 degrees, at least about 10 degrees, at least about 15 degrees, at least about 30 degrees, at least about 45 degrees, at least about 60 degrees, at least about 90 degrees, at least about 120 degrees, at least about 180 degrees, at least about 240 degrees, and at least about 270 degrees different from the second rotational orientation relative to a second portion of the treatment surface of the device. The specified EEG frequency may be an intrinsic frequency as described herein. The specified EEG frequency may be a pre-selected frequency as described herein. The pre-selected frequency may be an average intrinsic frequency of a healthy population database within a specified EEG band.

In some embodiments, a magnetic field results from a first magnetic source and a second magnetic source. In some embodiments, the first magnetic source and the second magnetic source are out of phase relative to each other. In some embodiments, the amount that the first magnetic source and the second magnetic source are out of phase relative to each other is called the magnetic phase.

In some embodiments, the first portion of the treatment surface is the portion of the treatment surface approximately closest to the first permanent magnet, and wherein the second portion of the treatment surface is the portion of the treatment surface approximately closest to the second permanent magnet. In some embodiments, the first portion of the treatment surface is the portion of the treatment surface closest to the first permanent magnet that is intended to be approximately tangential to the head of the subject nearest that treatment surface, and wherein the second portion of the treatment surface is the portion of the treatment surface approximately closest to the second permanent magnet that is intended to be approximately tangential to the head of the subject nearest that treatment surface.

In some embodiments of the devices disclosed herein, the difference between the first rotational orientation and the second rotational orientation results in a magnetic phase when the first permanent magnet is moved at the same frequency as the second permanent magnet. The magnetic phase of the device may be operable to influence an EEG phase between a first site and a second site in the brain of a subject within a specified EEG band. The first site generally aligns with the first permanent magnet, and the second site generally aligns with the second permanent magnet of the device.

Provided herein is a device comprising,
(a) a means for applying a first magnetic field to a head of a subject; and
(b) a means for applying a second magnetic field to a head of a subject;

whereby the means for applying the first magnetic field and the means for applying the second magnetic field are capable of influencing an EEG phase between at least two sites in a brain of the subject of a specified EEG frequency.

The magnetic fields (first magnetic field, and second magnetic field) may be of the same frequency, but out of phase with each other. Additional magnetic fields may be provided by additional means for applying such magnetic fields. These too may be out of phase with each other, or with any of the magnetic fields. Nevertheless, the magnetic fields in some embodiments may have the same frequencies. The devices may be a Permanent Magneto-EEG Resonant Therapy (pMERT) (i.e. a Neuro-EEG Synchronization Therapy NEST device) as described herein. The specified EEG frequency may be an intrinsic frequency as described herein. The specified EEG frequency may be a pre-selected frequency as described herein. The pre-selected frequency may be an average intrinsic frequency of a healthy population database within a specified EEG band.

In some aspects, is a device for use in treating a subject, comprising: a Transcranial Magnetic Stimulation (TMS) device; whereby the means for applying the magnetic field is capable of influencing (a) an intrinsic frequency of a brain of the subject within a specified EEG band; (b) a Q-factor of an intrinsic frequency of a brain of the subject within a specified EEG band; (c) a coherence of intrinsic frequencies among multiple sites in a brain of the subject within a specified EEG band; or (d) a combination thereof.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

A better understanding of the features and advantages of the systems and methods provided will be obtained by reference to the following detailed description that sets forth illustrative embodiments and the accompanying drawings of which:

FIG. 40 shows a general relationship between the measures of neural activity in the cortex and a possible indication for major Depressive Disorder (MDD).

DETAILED DESCRIPTION OF THE INVENTION

Figure 1:
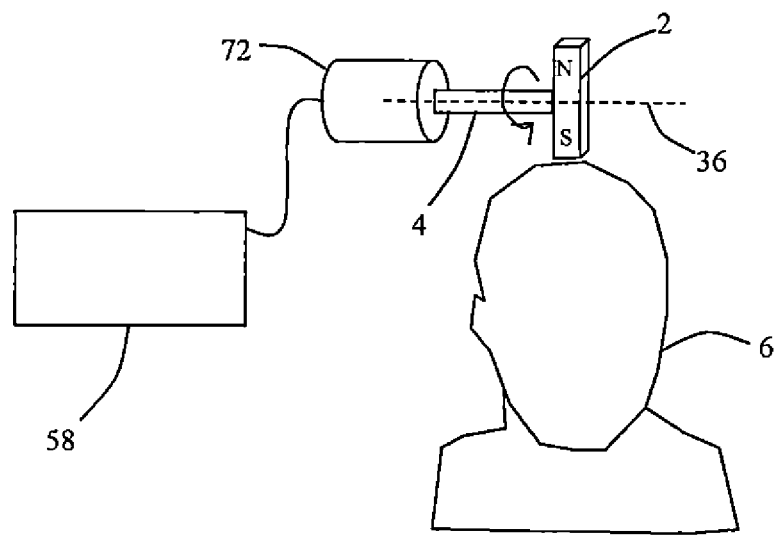
FIG. 1 shows an exemplary device in which the magnet rotates so that the plane of rotation is perpendicular to the surface of the scalp.

While certain embodiments have been provided and described herein, it will be readily apparent to those skilled in the art that such embodiments are provided by way of example only. It should be understood that various alternatives to the embodiments described herein may be employed, and are part of the invention described herein.

Since brain activity is a distributed phenomenon, conventional high-energy pulses used by rTMS that focus on a specific area of the brain may not be optimal for influencing the overall frequency of the brain. Instead of using short high-energy pulses at the desired frequency, it is possible instead use a sinusoidal or near-sinusoidal magnetic field (likely with lower energy) to generate a similar effect. To affect the brain with a lower energy magnetic field, the stimulation may need to be applied for a longer period.

In some embodiments, described are methods and devices that provide low frequency sinusoidal or near-sinusoidal transcranial magnetic stimulation therapy by rotating one or more permanent magnets in close proximity to the subject's head.

Described are methods and systems for novel, inexpensive, easy to use therapy for a number of mental disorders. Described are methods and devices to treat mental disorders that involve no medication. Methods and devices described herein gently "tune" the brain and affect mood, focus, and cognition of subjects.

In one aspect are methods of treating a subject, comprising: (a) adjusting output of a magnetic field for influencing an intrinsic frequency of a specified EEG band of the subject toward a pre-selected or target intrinsic frequency of the specified EEG band; and (b) applying said magnetic field close to a head of the subject.

In another aspect are methods of altering an intrinsic frequency of a brain of a subject within a specified EEG band, comprising: (a) determining the intrinsic frequency of the subject within the specified EEG band; (b) comparing the intrinsic frequency from step (a) to an average intrinsic frequency of a healthy population database; (c) if the intrinsic frequency from step (a) is higher than the average intrinsic frequency of the healthy population database, shifting down the intrinsic frequency of the subject by applying a specific magnetic field close to a head of the subject, wherein said specific magnetic field has a frequency lower than the intrinsic frequency of the subject; and (d) if the intrinsic frequency from step (a) is lower than the average intrinsic frequency of the healthy population database, shifting up the intrinsic frequency of the subject by applying a specific magnetic field close to a head of the subject, wherein said specific magnetic field has a frequency higher than the intrinsic frequency of the subject. Provided herein are methods of treating a subject, comprising determining the intrinsic frequency (f) of the subject within the specified EEG band by: obtaining EEG data of the subject's brain; removing any DC component in the signal; performing a Fast Fourier Transformation the EEG data to determine a FFT curve X(f); and achieving a fitted Gaussian curve, A(f), of a local maximum of the FFT curve X(f) by: using the equation $A(f) = Ge^{(-f-s)^2/2d^2}$ (also depicted in FIG. 34), wherein G is gain, d is standard deviation, and s is the mean frequency based on the specified EEG band, and determining a goodness of fit measure by optimizing using the following equation $$H(X, A) = \sum_{f=s-1Hz}^{s+1Hz} |X(f) - A(f)|$$

(also depicted in FIG. 35), by: estimating a first mean frequency, a first standard of deviation, and first gain for the first optimizing loop, shifting the gain, G, up or down slightly from the first gain, determining a new gain resulting in a better fit than that of the first gain, shifting the standard of deviation, d, up or down slightly from the first standard of deviation, determining a new standard of deviation resulting in a better fit than that of the first standard of deviation, shifting the mean frequency, s, up or down slightly from the first mean frequency, determining a new mean frequency resulting in a better fit than that of the first mean frequency, and repeating steps 2), 3), and 4), in which the first gain, the first standard of deviation, and the first mean frequency are replaced with a second gain, a second standard of deviation, and a second mean frequency, respectively, until the three parameters are optimized, comparing the intrinsic frequency from step (a) to an average intrinsic frequency of a healthy population database; if the intrinsic frequency from step (a) is higher than the average intrinsic frequency of the healthy population database, shifting down the intrinsic frequency of the subject by applying a magnetic field close to a head of the subject, wherein said magnetic field has a frequency lower than the intrinsic frequency of the subject; and if the intrinsic frequency from step (a) is lower than the average intrinsic frequency of the healthy population database, shifting up the intrinsic frequency of the subject by applying a magnetic field close to a head of the subject, wherein said magnetic field has a frequency higher than the intrinsic frequency of the subject.

In another aspect are methods of altering an intrinsic frequency of a brain of a subject within a specified EEG band, comprising: (a) determining the intrinsic frequency of the subject within the specified EEG band; (b) comparing the intrinsic frequency from step (a) to an average intrinsic frequency of a healthy population database; (c) if the intrinsic frequency from step (a) is higher than the average intrinsic frequency of the healthy population database, shifting down the intrinsic frequency of the subject by applying a specific magnetic field close to a head of the subject, wherein said specific magnetic field has a frequency lower than the intrinsic frequency of the subject; and (d) if the intrinsic frequency from step (a) is lower than the average intrinsic frequency of the healthy population database, shifting up the intrinsic frequency of the subject by applying a specific magnetic field close to a head of the subject, wherein said specific magnetic field has a frequency higher than the intrinsic frequency of the subject.

Provided herein are methods of treating a subject, comprising determining the intrinsic frequency (f) of the subject within the specified EEG band by: obtaining EEG data of the subject's brain; performing a Fourier Transformation (which may or may not be a fast fourier transformation) of the EEG data to determine a curve X(f); and achieving a fitted curve around a local maximum of the curve X(f).

In some embodiments, the fitted curve is a Gaussian curve. In some embodiments, the fitted curve is a second degree polynomial curve. In some embodiments, the fitted curve is a third degree polynomial curve. In some embodiments, the fitted curve is a complex curve. In some embodiments, the fitted curve is used to determine the Q factor. In some embodiments, the fitted curve is used in determining a coherence value. In some embodiments the goodness of fit is determined by a least squares method. In some embodiments the goodness of fit is determined by a ordinary least squares method. In some embodiments the goodness of fit is determined by a total least squares method. In some embodiments the goodness of fit is determined by a non-linear least squares method. In some embodiments the goodness of fit is determined by a weighted least squares method. In some embodiments the fitted curve is determined by nonlinear regression. In some embodiments the fitted curve is determined by regression analysis. In some embodiments the fitted curve is determined by at least one of an exponential function, a logarithmic function, a trigometirc function, a power function, a Gaussian function, and a Loerntzian curve function. In some embodiments, the fitted curve is determined by polynomial interpolation.

In some embodiments, the method comprises comparing the intrinsic frequency to an average intrinsic frequency of a healthy population database; if the intrinsic frequency is higher than the average intrinsic frequency of the healthy population database, shifting down the intrinsic frequency of the subject by applying a magnetic field close to a head of the subject, wherein said magnetic field has a frequency lower than the intrinsic frequency of the subject; and if the intrinsic frequency is lower than the average intrinsic frequency of the healthy population database, shifting up the intrinsic frequency of the subject by applying a magnetic field close to a head of the subject, wherein said magnetic field has a frequency higher than the intrinsic frequency of the subject.

Provided herein is a method of using a Transcranial Magnetic Stimulation (TMS) device for influencing an intrinsic frequency of a subject within a specified EEG band, comprising: adjusting output of said TMS device; changing EEG frequency, Q-factor, or coherence by repetitive firing of a magnetic field using said TMS device; and applying said magnetic field close to a head of the subject, wherein the intrinsic frequency of the subject within the specified EEG band is determined by: obtaining EEG data of the subject's brain; removing any DC component in the signal; performing a Fast Fourier Transformation the EEG data to determine a FFT curve X(f); and achieving a fitted Gaussian curve, A(f), of a local maximum of the FFT curve X(f) by: using the equation $A(f)=Ge^{(-f-s)^2/2d^2}$ (also depicted in FIG. 34), wherein G is gain, d is standard deviation, and s is the mean frequency based on the specified EEG band, and determining a goodness of fit measure by optimizing using the following equation $$H(X, A) = \sum_{f=s-1Hz}^{s+1Hz} |X(f) - A(f)|$$

(also depicted in FIG. 35), by: estimating a first mean frequency, a first standard of deviation, and first gain for the first optimizing loop, shifting the gain, G, up or down slightly from the first gain, determining a new gain resulting in a better fit than that of the first gain, shifting the standard of deviation, d, up or down slightly from the first standard of deviation, determining a new standard of deviation resulting in a better fit than that of the first standard of deviation, shifting the mean frequency, s, up or down slightly from the first mean frequency, determining a new mean frequency resulting in a better fit than that of the first mean frequency, and repeating steps 2), 3), and 4), in which the first gain, the first standard of deviation, and the first mean frequency are replaced with a second gain, a second standard of deviation, and a second mean frequency, respectively, until the three parameters are optimized.

In some embodiments, the local maximum of the FFT X(f) curve is based on the EEG band of interest (the specified EEG band). In some embodiments, the local maximum is between 8 Hz and 13 Hz within the alpha band.

As used herein the terms "FFT", "Fast Fourier Transform", and "Fast Fourier Transformation" may be used interchangeably.

In some embodiments, the intrinsic frequency of a brain of a subject, for example, in the alpha band, may be determined as follows: Capture 30 sec worth of EEG data at 256 samples/sec. Filter the data twice with a 10th order 3 Hz high-pass IIR filter. Note that this removes any DC component in the signal. Perform a Fast Fourier Transform (FFT) on the EEG data to determine X(f). The size of the FFT is twice the number of EEG samples. Achieve the best fit of a Gaussian curve to the FFT in the band from 8 Hz-13 Hz over the following parameters (depicted in FIG. 34 and below), where mean frequency is "s", gain is "G" and standard deviation is "d".

$$A(f) = Ge^{(-(f-s)^2/2d^2)}$$

To determine a goodness of fit measure, subtract one waveform from the other, take the absolute value, and sum. Use a window around the Gaussian curve that goes +/−1 Hz on either side of the Gaussian peak. Although the Mean frequency is limited to a value between 8 Hz and 13 Hz, the window is allowed to go outside this region if necessary. The formula for goodness of fit of the FFT of the EEG data X(f) and the fitted Gaussian curve A(f) is given below (and depicted in FIG. 35).

$$H(X, A) = \sum_{f=s-1Hz}^{s+1Hz} |X(f) - A(f)|$$

Before the optimization loop, choose estimates for s, d, and G. For each cycle of the loop, perform the following:
1. Shift the gain up or down slightly:
   a. Calculate the fit for the current G.
   b. Calculate the fit for G+0.01
   c. Calculate the fit for G−0.01
   d. Set the new G to the value that has the best fit.
2. Shift the standard deviation up or down slightly:
   a. Calculate the fit for the current d.
   b. Calculate the fit for d+0.001
   c. Calculate the fit for d−0.001
   d. Set the new d to the value that has the best fit.
3. Shift the mean frequency up or down slightly:
   a. Calculate the fit for the current s.
   b. Calculate the fit for s+1 FFT sample
   c. Calculate the fit for s−1 FFT sample
   d. Set the new s to the value that has the best fit for which the new s is in the range from 8 Hz to 13 Hz.

Figures 35, 36:
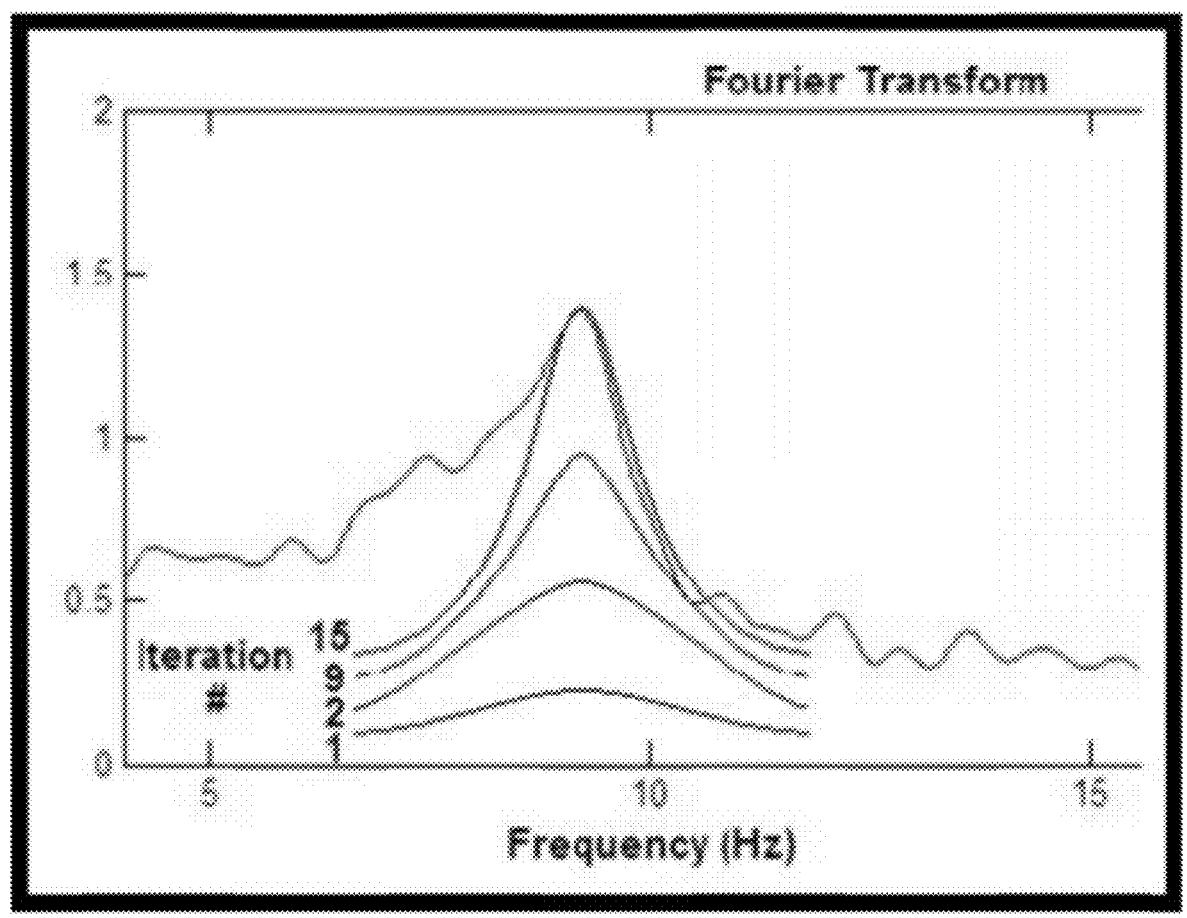
FIG. 35 shows an equation for the goodness of fit of the FFT (Fast Fourier Transformation) X(f) and the fitted Gaussian curve A(f) of the EEG data from a subject.
FIG. 36 shows the Fast Fourier Transformation of EEG data of a subject in the alpha band, and shows one, two, nine and fifteen optimization iteration(s) of the fitted Gaussian curve A(f) where the gain G is chosen as a low value (one fourth of the peak value of the FFT curve in the alpha band) such that with subsequent iterations, the fitted curve rises up from the x-axis to determine the optimal fit of A(f).
Figure 37:
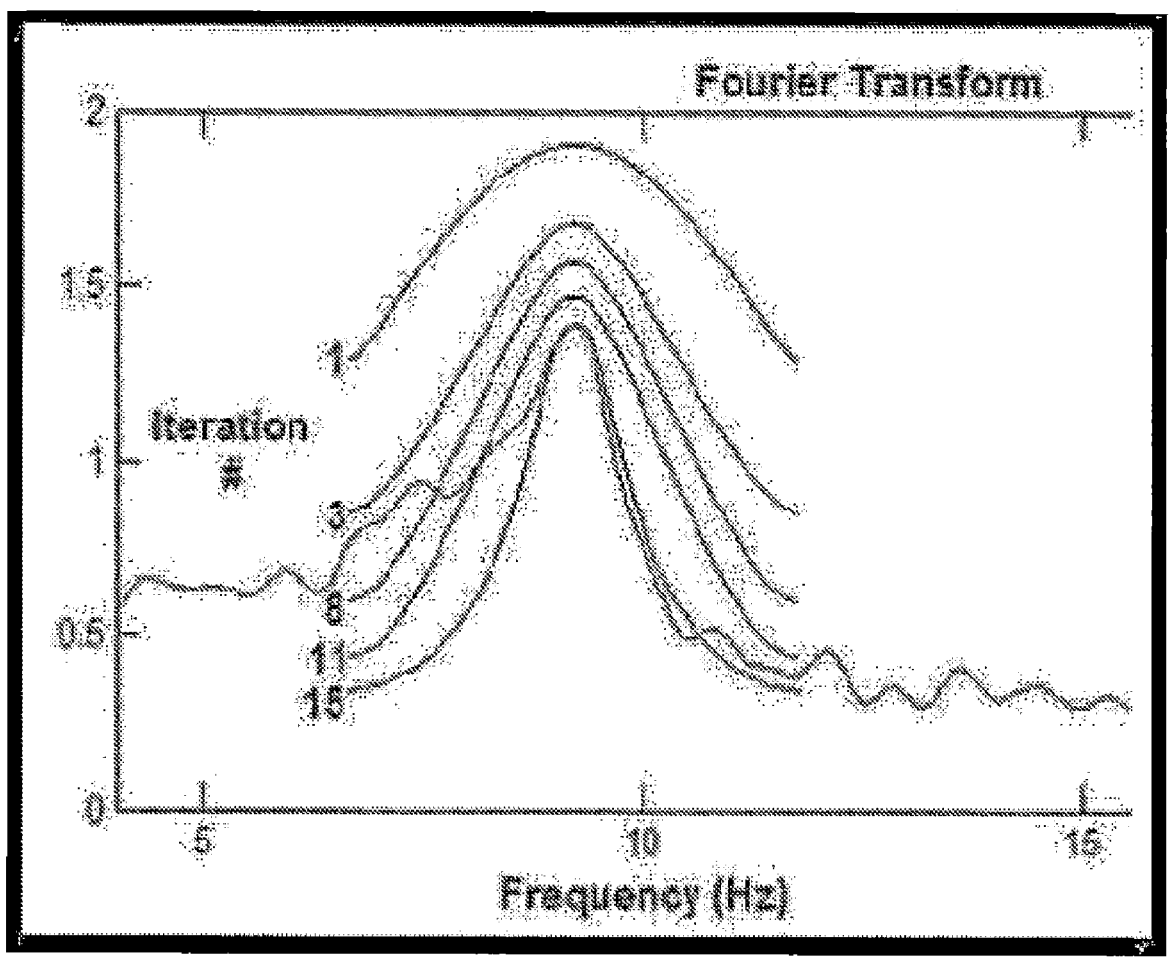
FIG. 37 shows the Fast Fourier Transformation of EEG data of a subject in the alpha band, and shows one, three, eight, eleven, and fifteen optimization iteration(s) of the fitted Gaussian curve A(f) where the gain G is chosen as a high value (1.5 times the peak value of the FFT curve in the alpha band) such that with subsequent iterations, the fitted curve moved down toward the x-axis to determine the optimal fit of A(f).

The loop continues until all three parameters are optimized and none of them changes. The optimization method goes through two complete optimizations in order to avoid local optima. It first picks a starting point that with a very low value for G (¼ the peak value of the FFT in the alpha band) so that the fitted curve will rise up from the bottom to determine the optimal fit (as depicted in FIG. 36). Then the algorithm goes through a second optimization with a high G (1.5× the peak value of the FFT in the alpha band) that will result in an initial curve that is guaranteed to be above the FFT and move down to determine the optimal fit (as depicted in FIG. 37). The value for the alpha frequency is the mean frequency s for the curve that results in the best match. FIGS. 36 and 37 show sample fitted curves to the Fourier transform of the EEG data. FIG. 36 shows the curve as iterations progress moving up from a low G. FIG. 37 shows the same optimization moving down from an initial high G. In this example, both methods converge to the same fitted curve. However, one method may give a better fit if the Fourier transform contains spurious peaks or is noisy. In some embodiments, the method comprises the step of measuring EEG data of the subject after the applying step.

In some embodiments, the method comprises the steps of: adjusting frequency of said magnetic field based on the EEG data of the subject; and repeating the applying step with an adjusted frequency. In some embodiments, applying of the magnetic field applies the magnetic field to a diffuse area in a brain of the subject. In some embodiments, the magnetic field is generated by movement of at least one permanent magnet. In some embodiments, said movement comprises at least one of rotational motion, linear motion, and swing motion. In some embodiments, a frequency of the magnetic field with the specified EEG band is from about 0.5 Hz to about 100 Hz. In some embodiments, the strength of the at least one permanent magnet is from about 10 Gauss to about 4 Tesla. In some embodiments, the distance between the at least one permanent magnet and the subject is from about 1/32 in to about 12 in. In some embodiments, the step of applying the magnetic field is for about 5 minutes to about two hours. In some embodiments, the method comprises repeating the applying step after an interval about 6 hours to about 14 days.

In some embodiments, the magnetic field is generated by a Transcranial Magnetic Stimulation device which generates the magnetic field using an electromagnetic coil.

In some embodiments, a frequency of the magnetic field with the specified EEG band is from about 0.5 Hz to about 100 Hz.

In some embodiments, the method comprises: (a) locating a first electrode operable to detect electrical brain activity on the subject in at least one of an area of low electrical resistivity on a subject, and an area with substantially no electrical impulse interference on a subject; (b) locating a second electrode operable to detect a reference signal on the subject; and (c) determining the intrinsic frequency from the electrical brain activity detected by the first electrode and the reference signal detected by the second electrode.

In some embodiments, the method improves an indication selected from the group consisting of replacement for meditation, quick nap, stress release, attention span, comprehension, memory, lowered blood pressure, increased libido, sports performance, academic performance, increased blood flow, lowered blood flow, increased metabolism, lowered metabolism, and any combination thereof. In some embodiments, the method is adapted to improve any of these indications.

In some embodiments, the method improves a disorder selected from the group consisting of depression, bipolar, anxiety, obsessive-compulsive, seizure, Parkinson's disease, ADHD, autism, substance abuse, head injury, Alzheimer's disease, eating disorder, sleep disorder, tinnitus, fibromyalgia, and any combination thereof. In some embodiments, the method is adapted to improve any of these disorders. In some embodiments fibromyalgia is considered a musculoskeletal disease and/or a neuropsychiatric condition. In some embodiments fibromyalgia is not a neurological disorder.

Certain types of neuropathic pain may also be treated with the devices and methods provided herein. This may include, for nonlimiting example occipital neuralgia (affecting the head), neuritis (inflammation of a nerve), trigeminal neuralgia (affecting the facial areas), peripheral neuralgia, sciatic neuralgia (sciatica), intercostal neuralgia (affecting the ribs), postherpetic neuralgia (related to shingles), diabetic neuropathy, and glossopharyngeal neuralgia (affecting the tongue and throat). In some embodiments, the devices and methods provided herein are adapted to treat Psychalgia (psychogenic pain).

Likewise, certain types of neurologic disorders may be treated with the devices and methods provided herein. Neurological disorders can be categorized according to the primary location affected, the primary type of dysfunction involved, or the primary type of cause. The broadest division is between central nervous system (CNS) disorders and peripheral nervous system (PNS) disorders. Brain, spinal cord and nerve disorders may be described in several overlapping categories. These categories include brain neurological disorders, spinal cord disorders, peripheral nervous system disorders, cranial nerve disorders, autonomic nervous system disorders, seizure disorders such as epilepsy, movement disorders such as Parkinson's disease, sleep disorders, headaches such as migraine, lower back and neck pain, other generalized neuropathic pain, delirium and dementia such as Alzheimer's disease, dizziness and vertigo, stupor and coma, head injury, stroke including CVA and cerebrovascular attack, multiple sclerosis and other demylenating diseases, infections of the brain or spinal cord including meningitis, prion diseases, and complex regional pain syndrome (CRPS) which is a chronic pain condition.

Brain neurological disorders may be further categorized into brain damage and brain dysfunction. Brain damage includes damage according to cerebral lobe (including lower brain areas such as basal ganglia, cerebellum, brainstem), and may include Frontal lobe damage, Parietal lobe damage, Temporal lobe damage, and Occipital lobe damage. Brain dysfunction includes aphasia (affecting language), dysarthria (affecting speech), apraxia (affecting patterns or sequences of movements), agnosia (affecting identification of things or people), and amnesia (affecting memory).

In some embodiments, the method is adapted to improve neuropathic pain, wherein the neuropathic pain comprises at least one of: occipital neuralgia, neuritis, trigeminal neuralgia, peripheral neuralgia, sciatic neuralgia, intercostal neuralgia, postherpetic neuralgia, diabetic neuropathy, and glossopharyngeal neuralgia.

In some embodiments, the method is adapted to improve a neurological disorder, wherein the neurological disorder comprises at least one of: a brain neurological disorder, a spinal cord disorder, a peripheral nervous system disorder, a cranial nerve disorder, an autonomic nervous system disorder, a seizure disorder, a movement disorder, a sleep disorder, a headache, lower back pain, neck pain, other generalized neuropathic pain, delirium, dementia, dizziness, vertigo, stupor, coma, a head injury, a stroke, multiple sclerosis, a demylenating disease, an infection of the brain or spinal cord, a prion disease, and a complex regional pain syndrome.

In some embodiments, the method is adapted to improve a symptom of brain damage, wherein the brain damage comprises at least one of: cerebral lobe damage including lower brain areas such as the basal ganglia, the cerebellum, and the brainstem; frontal lobe damage, parietal lobe damage, temporal lobe damage, and occipital lobe damage.

In some embodiments, the method is adapted to improve brain dysfunction, wherein the brain dysfunction comprises at least one of: aphasia, dysarthria, apraxia, agnosia, and amnesia.

In some embodiments, the method improves a characteristic selected from the group consisting of peripheral visual response, attention span, immediate reaction time (IRT), movement time (MT), simple perceptual reaction time (SPR), conflict perceptual reaction time (CPR), and any combination thereof. In some embodiments, the method is adapted to improve any of these characteristics.

In some embodiments, the magnetic field results from a first magnetic source and a second magnetic source. In some embodiments, the first magnetic source and the second magnetic source are out of phase relative to each other.

In some embodiments, the EEG band is the alpha band, and the mean frequency ranges from about 8 Hz to about 13 Hz.

In some embodiments, removing the DC component of the signal comprises filtering the EEG data with a 10th order 3 Hz high-pass IIR filter. In some embodiments, removing the DC component of the signal comprises filtering the EEG data twice with a 10th order 3 Hz high-pass IIR filter.

In some embodiments, the EEG data comprises about 30 seconds worth of EEG data at about 256 samples per second.

In some embodiments, the first gain is about one fourth (¼) of the peak value of a peak value of the Fast Fourier Transformation of the EEG data.

In some embodiments, a second optimization is performed having a first gain of at least about 1.5 times the peak value of the Fast Fourier Transformation of the EEG data.

In some embodiments, at least one of the intrinsic frequency and the fitted Gaussian curve is used to determine a Q factor of the intrinsic frequency within the specified EEG band of the subject.

In some embodiments, at least one of the intrinsic frequency and the fitted Gaussian curve is used to determine a coherence value of intrinsic frequencies among multiple sites in the brain of a subject within a specified EEG band.

In some embodiments, at least one of the intrinsic frequency and the fitted Gaussian curve is used to determine an EEG phase between two sites in the brain of a subject of a specified EEG frequency.

In some embodiments, shifting the standard of deviation comprises a shift from the first standard deviation of at least one of about 0.005, about 0.01, about 0.02, about 0.05, about 0.1, about 0.2, about 0.5, about 0.6, about 0.7, about 0.75, about 0.8, about 0.9, about 1.0, about 1.1, about 1.2, about 1.5, about 1.75, about 2 and about 2.5. As used herein, the term "about" when used in reference to standard deviation can mean variations of 1%, 10%, 20%, 25%, 50%, 1%-5%, 1%-10%, 5% to 10%, 10% to 20%, 10% to 50%, 10% to 25%, and/or 25% to 50%.

In some embodiments, shifting the gain comprises a shift from the first gain of at least one of about 0.005, about 0.01, about 0.02, about 0.05, about 0.1, about 0.2, about 0.5, about 0.6, about 0.7, about 0.75, about 0.8, about 0.9, about 1.0, about 1.1, about 1.2, about 1.5, about 1.75, about 2 and about 2.5. As used herein, the term "about" when used in reference to gain can mean variations of 1%, 10%, 20%, 25%, 50%, 1%-5%, 1%-10%, 5% to 10%, 10% to 20%, 10% to 50%, 10% to 25%, and/or 25% to 50%.

In some embodiments, shifting the mean frequency comprises a shift from the first mean frequency of at least one of about 0.005, about 0.01, about 0.02, about 0.05, about 0.1, about 0.2, about 0.5, about 0.6, about 0.7, about 0.75, about 0.8, about 0.9, about 1.0, about 1.1, about 1.2, about 1.5, about 1.75, about 2 and about 2.5. As used herein, the term "about" when used in reference to mean frequency can mean variations of 1%, 10%, 20%, 25%, 50%, 1%-5%, 1%-10%, 5% to 10%, 10% to 20%, 10% to 50%, 10% to 25%, and/or 25% to 50%.

Provided herein is a device comprising: at least one permanent magnet, a subunit coupled to the magnet, wherein the subunit enables movement of said at least one permanent magnet at a frequency between about 0.5 Hz and about 100 Hz, and logic that is operable to determine an intrinsic frequency (f) of a brain of a subject within a specified EEG band by: obtaining EEG data of the subject's brain; removing any DC component in the signal; performing a Fast Fourier Transformation the EEG data to determine a FFT curve X(f); and achieving a fitted Gaussian curve, A(f), of a local maximum of the FFT curve X(f) by: using the equation $A(f) = Ge^{(-f-s)^2/2d^2}$ (also depicted in FIG. 34), wherein G is gain, d is standard deviation, and s is the mean frequency based on the specified EEG band, and determining a goodness of fit measure by optimizing using the following equation $$H(X, A) = \sum_{f=s-1Hz}^{s+1Hz} |X(f) - A(f)|$$

(also depicted in FIG. 35), by: estimating a first mean frequency, a first standard of deviation, and first gain for the first optimizing loop, shifting the gain, G, up or down slightly from the first gain, determining a new gain resulting in a better fit than that of the first gain, shifting the standard of deviation, d, up or down slightly from the first standard of deviation, determining a new standard of deviation resulting in a better fit than that of the first standard of deviation, shifting the mean frequency, s, up or down slightly from the first mean frequency, determining a new mean frequency resulting in a better fit than that of the first mean frequency, and repeating steps 2), 3), and 4), in which the first gain, the first standard of deviation, and the first mean frequency are replaced with a second gain, a second standard of deviation, and a second mean frequency, respectively, until the three parameters are optimized.

In some embodiments, the device is operable to at least one of: influence the intrinsic frequency of the brain of a subject within the specified EEG band; influence a Q-factor of the intrinsic frequency; influence a coherence of intrinsic frequencies among multiple sites in the brain of a subject within a specified EEG band; and influence an EEG phase between two sites in the brain of a subject of a specified EEG frequency.

In some embodiments, a magnetic field is generated by movement of at least the permanent magnet. In some embodiments, said movement comprises at least one of rotational motion, linear motion, and swing motion.

In some embodiments, the device comprises logic that controls the frequency in increments of about 0.1 Hz.

In some embodiments, the device improves an indication selected from the group consisting of replacement for meditation, quick nap, stress release, attention span, comprehension, memory, lowered blood pressure, increased libido, sports performance, academic performance, increased blood flow, lowered blood flow, increased metabolism, lowered metabolism, and any combination thereof. In some embodiments, the device is adapted to improve any of these indications.

In some embodiments, the device improves a disorder selected from the group consisting of depression, bipolar, anxiety, obsessive-compulsive, seizure, Parkinson's disease, ADHD, autism, substance abuse, head injury, Alzheimer's disease, eating disorder, sleep disorder, tinnitus, fibromyalgia, and any combination thereof. In some embodiments, the device is adapted to improve any of these disorders. In some embodiments fibromyalgia is considered a musculoskeletal disease and/or a neuropsychiatric condition. In some embodiments fibromyalgia is not a neurological disorder.

Certain types of neuropathic pain may also be treated with the devices and methods provided herein. This may include, for nonlimiting example occipital neuralgia (affecting the head), neuritis (inflammation of a nerve), trigeminal neuralgia (affecting the facial areas), peripheral neuralgia, sciatic neuralgia (sciatica), intercostal neuralgia (affecting the ribs), postherpetic neuralgia (related to shingles), diabetic neuropathy, and glossopharyngeal neuralgia (affecting the tongue and throat). In some embodiments, the devices and methods provided herein are adapted to treat Psychalgia (psychogenic pain).

Likewise, certain types of neurologic disorders may be treated with the devices and methods provided herein. Neurological disorders can be categorized according to the primary location affected, the primary type of dysfunction involved, or the primary type of cause. The broadest division is between central nervous system (CNS) disorders and peripheral nervous system (PNS) disorders. Brain, spinal cord and nerve disorders may be described in several overlapping categories. These categories include brain neurological disorders, spinal cord disorders, peripheral nervous system disorders, cranial nerve disorders, autonomic nervous system disorders, seizure disorders such as epilepsy, movement disorders such as Parkinson's disease, sleep disorders, headaches such as migraine, lower back and neck pain, other generalized neuropathic pain, delirium and dementia such as Alzheimer's disease, dizziness and vertigo, stupor and coma, head injury, stroke including CVA and cerebrovascular attack, multiple sclerosis and other demylenating diseases, infections of the brain or spinal cord including meningitis, prion diseases, and complex regional pain syndrome (CRPS) which is a chronic pain condition.

Brain neurological disorders may be further categorized into brain damage and brain dysfunction. Brain damage includes damage according to cerebral lobe (including lower brain areas such as basal ganglia, cerebellum, brainstem), and may include Frontal lobe damage, Parietal lobe damage, Temporal lobe damage, and Occipital lobe damage. Brain dysfunction includes aphasia (affecting language), dysarthria (affecting speech), apraxia (affecting patterns or sequences of movements), agnosia (affecting identification of things or people), and amnesia (affecting memory).

In some embodiments, the device is adapted to improve neuropathic pain, wherein the neuropathic pain comprises at least one of: occipital neuralgia, neuritis, trigeminal neuralgia, peripheral neuralgia, sciatic neuralgia, intercostal neuralgia, postherpetic neuralgia, diabetic neuropathy, and glossopharyngeal neuralgia.

In some embodiments, the device is adapted to improve a neurologic disorder, wherein the neurologic disorder comprises at least one of: a brain neurological disorder, a spinal cord disorder, a peripheral nervous system disorder, a cranial nerve disorder, an autonomic nervous system disorder, a seizure disorder, a movement disorder, a sleep disorder, a headache, lower back pain, neck pain, other generalized neuropathic pain, delirium, dementia, dizziness, vertigo, stupor, coma, a head injury, a stroke, multiple sclerosis, a demylenating disease, an infection of the brain or spinal cord, a prion disease, and a complex regional pain syndrome.

In some embodiments, the device is adapted to improve a symptom of brain damage, wherein the brain damage comprises at least one of: cerebral lobe damage including lower brain areas such as the basal ganglia, the cerebellum, and the brainstem; frontal lobe damage, parietal lobe damage, temporal lobe damage, and occipital lobe damage.

In some embodiments, the device is adapted to improve brain dysfunction, wherein the brain dysfunction comprises at least one of: aphasia, dysarthria, apraxia, agnosia, and amnesia.

In some embodiments, the device improves a characteristic selected from the group consisting of peripheral visual response, attention span, immediate reaction time (IRT), movement time (MT), simple perceptual reaction time (SPR), conflict perceptual reaction time (CPR), and any combination thereof. In some embodiments, the device is adapted to improve any of these characteristics.

In some embodiments, shifting the standard of deviation comprises a shift from the first standard deviation of at least one of about 0.005, about 0.01, about 0.02, about 0.05, about 0.1, about 0.2, about 0.5, about 0.6, about 0.7, about 0.75, about 0.8, about 0.9, about 1.0, about 1.1, about 1.2, about 1.5, about 1.75, about 2 and about 2.5. As used herein, the term "about" when used in reference to standard deviation can mean variations of 1%, 10%, 20%, 25%, 50%, 1%-5%, 1%-10%, 5% to 10%, 10% to 20%, 10% to 50%, 10% to 25%, and/or 25% to 50%.

In some embodiments, shifting the gain comprises a shift from the first gain of at least one of about 0.005, about 0.01, about 0.02, about 0.05, about 0.1, about 0.2, about 0.5, about 0.6, about 0.7, about 0.75, about 0.8, about 0.9, about 1.0, about 1.1, about 1.2, about 1.5, about 1.75, about 2 and about 2.5. As used herein, the term "about" when used in reference to gain can mean variations of 1%, 10%, 20%, 25%, 50%, 1%-5%, 1%-10%, 5% to 10%, 10% to 20%, 10% to 50%, 10% to 25%, and/or 25% to 50%.

In some embodiments, shifting the mean frequency comprises a shift from the first mean frequency of at least one of about 0.005, about 0.01, about 0.02, about 0.05, about 0.1, about 0.2, about 0.5, about 0.6, about 0.7, about 0.75, about 0.8, about 0.9, about 1.0, about 1.1, about 1.2, about 1.5, about 1.75, about 2 and about 2.5. As used herein, the term "about" when used in reference to mean frequency can mean variations of 1%, 10%, 20%, 25%, 50%, 1%-5%, 1%-10%, 5% to 10%, 10% to 20%, 10% to 50%, 10% to 25%, and/or 25% to 50%.

Certain types of neuropathic pain may also be treated with the devices and methods provided herein. This may include, for nonlimiting example occipital neuralgia (affecting the head), neuritis (inflammation of a nerve), trigeminal neuralgia (affecting the facial areas), peripheral neuralgia, sciatic neuralgia (sciatica), intercostal neuralgia (affecting the ribs), postherpetic neuralgia (related to shingles), diabetic neuropathy, and glossopharyngeal neuralgia (affecting the tongue and throat). In some embodiments, the devices and methods provided herein are adapted to treat Psychalgia (psychogenic pain).

Likewise, certain types of neurologic disorders may be treated with the devices and methods provided herein. Neurological disorders can be categorized according to the primary location affected, the primary type of dysfunction involved, or the primary type of cause. The broadest division is between central nervous system (CNS) disorders and peripheral nervous system (PNS) disorders. Brain, spinal cord and nerve disorders may be described in several overlapping categories. These categories include brain neurological disorders, spinal cord disorders, peripheral nervous system disorders, cranial nerve disorders, autonomic nervous system disorders, seizure disorders such as epilepsy, movement disorders such as Parkinson's disease, sleep disorders, headaches such as migraine, lower back and neck pain, other generalized neuropathic pain, delirium and dementia such as Alzheimer's disease, dizziness and vertigo, stupor and coma, head injury, stroke including CVA and cerebrovascular attack, multiple sclerosis and other demylenating diseases, infections of the brain or spinal cord including meningitis, prion diseases, and complex regional pain syndrome (CRPS) which is a chronic pain condition.

Brain neurological disorders may be further categorized into brain damage and brain dysfunction. Brain damage includes damage according to cerebral lobe (including lower brain areas such as basal ganglia, cerebellum, brainstem), and may include Frontal lobe damage, Parietal lobe damage, Temporal lobe damage, and Occipital lobe damage. Brain dysfunction includes aphasia (affecting language), dysarthria (affecting speech), apraxia (affecting patterns or sequences of movements), agnosia (affecting identification of things or people), and amnesia (affecting memory).

Provided herein is a method comprising: adjusting output of a magnetic field for influencing at least one of an intrinsic frequency of a specified EEG band of a subject toward a pre-selected intrinsic frequency of the specified EEG band and a Q-factor of an intrinsic frequency within a specified EEG band of a subject toward a pre-selected Q-factor and applying said magnetic field close to a head of the subject; wherein at least one of the pre-selected intrinsic frequency and the pre-selected Q-factor is chosen in order to improve at least one of neuropathic pain in the subject, a neurological disorder in the subject, a symptom of brain damage, and brain dysfunction in the subject.

In some embodiments, the neuropathic pain comprises at least one of: occipital neuralgia, neuritis, trigeminal neuralgia, peripheral neuralgia, sciatic neuralgia, intercostal neuralgia, postherpetic neuralgia, diabetic neuropathy, and glossopharyngeal neuralgia.

In some embodiments, the neurological disorder comprises at least one of a brain neurological disorder, a spinal cord disorder, a peripheral nervous system disorder, a cranial nerve disorder, an autonomic nervous system disorder, a seizure disorder, a movement disorder, a sleep disorder, a headache, lower back pain, neck pain, other generalized neuropathic pain, delirium, dementia, dizziness, vertigo, stupor, coma, a head injury, a stroke, multiple sclerosis, a demylenating disease, an infection of the brain or spinal cord, a prion disease, and a complex regional pain syndrome.

In some embodiments, the brain damage comprises at least one of: cerebral lobe damage including lower brain areas such as the basal ganglia, the cerebellum, and the brainstem; frontal lobe damage, parietal lobe damage, temporal lobe damage, and occipital lobe damage.

In some embodiments, the brain dysfunction comprises at least one of: aphasia, dysarthria, apraxia, agnosia, and amnesia.

In some embodiments, the method comprises taking EEG measurements of the subject before the adjusting step or after the applying step, or both before the adjusting step and after the applying step. In some embodiments, the method comprises determining at least one of: the subject's intrinsic frequency of the specified EEG band and the subject's Q-factor of an intrinsic frequency within a specified EEG band. In some embodiments, the applying of the magnetic field applies the magnetic field to a diffuse area in a brain of the subject.

In some embodiments, the magnetic field is generated by movement of at least one permanent magnet. In some embodiments, the strength of the at least one permanent magnetic is from about 10 Gauss to about 4 Tesla. In some embodiments, the step of applying the magnetic field is for about 5 minutes to about two hours. In some embodiments, the method comprises repeating the applying step after an interval about 6 hours to about 14 days.

Provided herein is a device comprising: a means for adjusting output of a magnetic field for influencing at least one of: an intrinsic frequency of a specified EEG band of a subject toward a pre-selected intrinsic frequency of the specified EEG band; and a Q-factor of an intrinsic frequency within a specified EEG band of a subject toward a pre-selected Q-factor, wherein the means for adjusting the output of the magnetic field is adapted to apply said magnetic field close to a head of the subject, and wherein at least one of the pre-selected intrinsic frequency and the pre-selected Q-factor is chosen in order to improve at least one of: neuropathic pain in the subject, a neurological disorder in the subject, a symptom of brain damage, and brain dysfunction in the subject.

In some embodiments, the neuropathic pain comprises at least one of: occipital neuralgia, neuritis, trigeminal neuralgia, peripheral neuralgia, sciatic neuralgia, intercostal neuralgia, postherpetic neuralgia, diabetic neuropathy, and glossopharyngeal neuralgia.

In some embodiments, the neurological disorder comprises at least one of a brain neurological disorder, a spinal cord disorder, a peripheral nervous system disorder, a cranial nerve disorder, an autonomic nervous system disorder, a seizure disorder, a movement disorder, a sleep disorder, a headache, lower back pain, neck pain, other generalized neuropathic pain, delirium, dementia, dizziness, vertigo, stupor, coma, a head injury, a stroke, multiple sclerosis, a demylenating disease, an infection of the brain or spinal cord, a prion disease, and a complex regional pain syndrome.

In some embodiments, the brain damage comprises at least one of: cerebral lobe damage including lower brain areas such as the basal ganglia, the cerebellum, and the brainstem; frontal lobe damage, parietal lobe damage, temporal lobe damage, and occipital lobe damage.

In some embodiments, the brain dysfunction comprises at least one of: aphasia, dysarthria, apraxia, agnosia, and amnesia.

In some embodiments, the device comprises at least one permanent magnet. In some embodiments, the strength of the at least one permanent magnetic is from about 10 Gauss to about 4 Tesla.

In some embodiments, the device comprises an electromagnetic coil. In some embodiments, the electromagnetic coil emits field strengths of about 10 Gauss to about 4 Tesla.

In some embodiments, the magnetic field is generated by movement of at least one permanent magnet. In some embodiments, the movement of the at least one said magnet is at a frequency between about 0.5 Hz and about 100 Hz. In some embodiments, the movement comprises at least one of rotational motion, linear motion, and swing motion. In some embodiments, the movement generates an alternating magnetic field.

In some embodiments, the device comprises logic that controls a output of the magnetic field to be any frequency between about 0.5 Hz and about 100 Hz in increments of about 0.1 Hz.

In another aspect are methods of treating a subject, comprising: (a) adjusting output of a magnetic field for influencing a Q-factor, a measure of frequency selectivity of a specified EEG band, of the subject toward a pre-selected or target Q-factor of the band; and (b) applying said magnetic field close to a head of the subject.

In another aspect are methods of treating a subject, comprising: determining the Q-factor of the intrinsic frequency within the specified EEG band of the subject; comparing the Q-factor of the intrinsic frequency from step (a) to an average Q-factor of the intrinsic frequency of a healthy population database; if the Q-factor of the intrinsic frequency from step (a) is higher than the average Q-factor of the intrinsic frequency of the healthy population database, tuning down the Q-factor of the intrinsic frequency of the subject by applying a magnetic field with a plurality of frequencies or with a single pre-selected frequency close to a head of the subject; and if the Q-factor of the intrinsic frequency from step (a) is lower than the average Q-factor of the intrinsic frequency of the healthy population database, tuning up the Q-factor of the intrinsic frequency of the subject by applying a magnetic field with a pre-selected frequency to a head of the subject.

In another aspect are methods of treating a subject, comprising: (a) adjusting output of a magnetic field for influencing a coherence of intrinsic frequencies among multiple sites in a brain of the subject within a specified EEG band toward a pre-selected or target coherence value; and (b) applying said magnetic field close to a head of the subject In another aspect are methods adjusting output of a magnetic field for influencing a coherence of intrinsic frequencies among multiple sites in a brain of the subject within a specified EEG band toward a pre-selected or target coherence value comprising: determining the coherence value of the intrinsic frequencies among multiple locations throughout a scalp of the subject; comparing the coherence value from step (a) to an average coherence value of a healthy population database; if the coherence value from step (a) is higher than the average coherence value of the healthy population database, lowering the coherence value of the subject by applying at least two asynchronous magnetic fields close to a head of the subject; if the coherence value from step (a) is lower than the average coherence value of the healthy population database, raising the coherence value of the subject by applying at least one synchronized magnetic field close to a head of the subject.

In another aspect are methods of using a Transcranial Magnetic Stimulation (TMS) device for influencing an intrinsic frequency of a subject within a specified EEG band, comprising: (a) adjusting output of said TMS device; (b) changing EEG frequency, Q-factor, or coherence by repetitive firing of a magnetic field using said TMS device; and (c) applying said magnetic field close to a head of the subject;

In another aspect are methods for treating a subject, comprising: (a) adjusting output of a magnetic field for influencing an EEG phase between two sites in the brain of a subject of a specified EEG frequency toward a pre-selected EEG phase of the specified EEG frequency; and (b) applying said magnetic field close to a head of the subject.

In another aspect are methods of treating anxiety in a subject, comprising tuning up the Q-factor of an intrinsic frequency of the subject by applying a magnetic field close to a head of the subject, wherein the magnetic field comprises at least one of (a) a single pre-selected frequency; (b) a plurality of frequencies within a specified EEG band; and (c) an intrinsic frequency of a brain of the subject within a specified EEG band. In some embodiments, any of the devices described herein may be used to treat anxiety.

In some embodiments, are method of treating depression in a subject, comprising tuning down the Q-factor of an intrinsic frequency of the subject by applying a magnetic field close to a head of the subject, wherein the magnetic field comprises at least one of (a) a single frequency; (b) a plurality of frequencies within a specified EEG band; and (c) an intrinsic frequency of a brain of the subject within a specified EEG band. In some embodiments, any of the devices described herein may be used to treat depression.

Increased neuronal activity in a region of the brain is associated with an increase in blood flow, and hence a higher rate of oxygenated/deoxygenated hemoglobin as measured by Blood Oxygenation Level Detection (BOLD). In Major Depressive Disorder ("MDD" and/or shortened herein in some embodiments as "depression"), there is a significant decrease in blood flow, and therefore a decrease in metabolic activity in the cortex. In some embodiments, the blood flow increase (and or increase in metabolic activity) is in the frontal cortex. This can be shown in studies using SPECT and PET scans. The lower the blood flow to the cortex, the greater the severity of the depression. This decreased blood flow becomes more significant for subjects with increased cognitive impairment associated with their depression. The decrease in regional cerebral blood flow (rCBF) is particularly evident in the prefrontal cortex and cingulated gyms. Studies of correlations between rCBF and symptom severity in MDD show a decrease in metabolism in the amygdale, lentiform nucleus, parahippocampal gyms, and an increase in metabolism in the postero-lateral parietal cortex. Other studies have shown an increase in blood flow in the lower regions of the brain during MDD, such as the cerebellum and amygdala for depressed subjects. The metabolism of a region of the brain can be related to the energy consumed by that region. An area of high metabolism may be considered an area of high energy or high activity. Likewise, an area of low metabolism may be considered an area of low energy.

Parallel to the rCBF studies, EEG studies have shown that MDD subjects have higher alpha band activities. The alpha band is a dominant EEG component with frequency ranged between 8 Hz and 13 Hz. A negative correlation has been shown between alpha power and the rCBF in the cortex where the alpha was measured. This suggests that a high alpha power is indicative of low rCBF, and therefore a low metabolism (and energy), in the region of cortex where the EEG was recorded. A number of studies have shown this excessive EEG alpha power, which may be a result of neural activity being overly synchronous. By applying a low magnitude alternating magnetic field, activity becomes less synchronous and EEG alpha power decreases. These changes correlate with improvement in clinical symptoms.

Figure 38A:
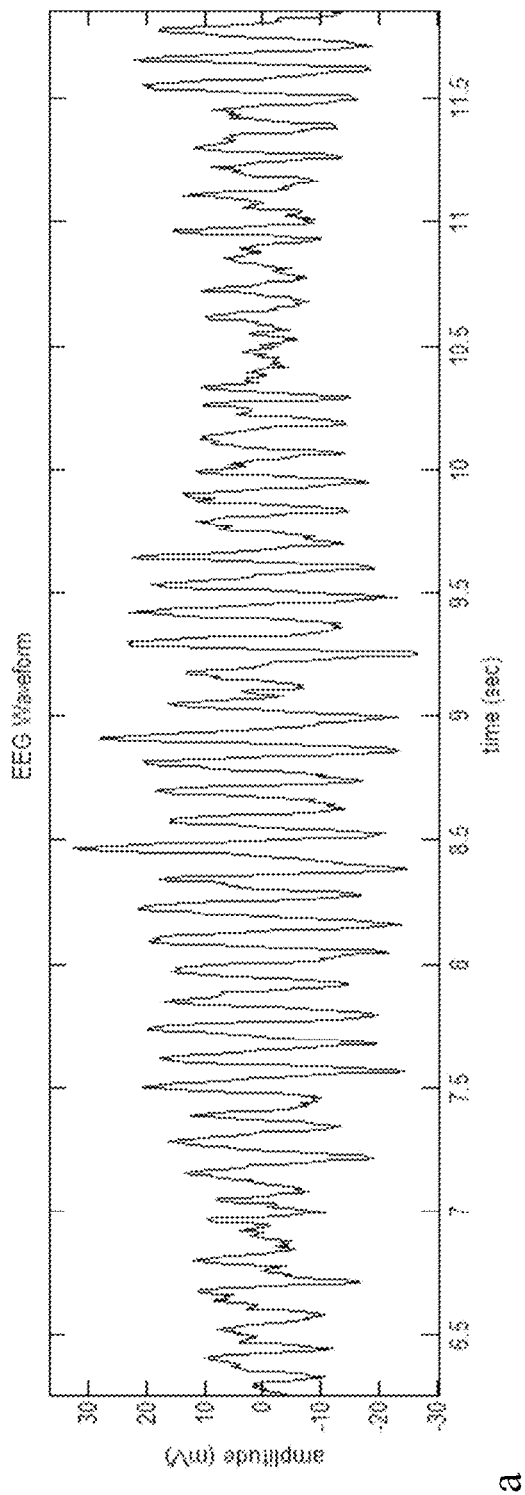
FIG. 38a shows an example EEG waveform for a subject having Major Depressive Disorder.

To understand alpha power and its relation to system energy, the frequency spectrum of the EEG was examined. FIGS. 38a-38d show the Fourier transform of two subjects, both with significantly different activity in the alpha band. Subjects were recorded during a resting period with eyes closed, which is a time when the alpha activity is most evident. However, alpha power is still present in the brain even when the eyes are open and the alpha wave is not seen on the conventional EEG. The plot of FIG. 38a shows an EEG that is significantly more synchronous than the plot of FIG. 38c. The Fourier transform (FIG. 38b) of the EEG of FIG. 38a shows an alpha frequency band that is more focused around the alpha frequency than the Fourier transform (FIG. 38d) of the EEG data of FIG. 38c).

Figure 38B:
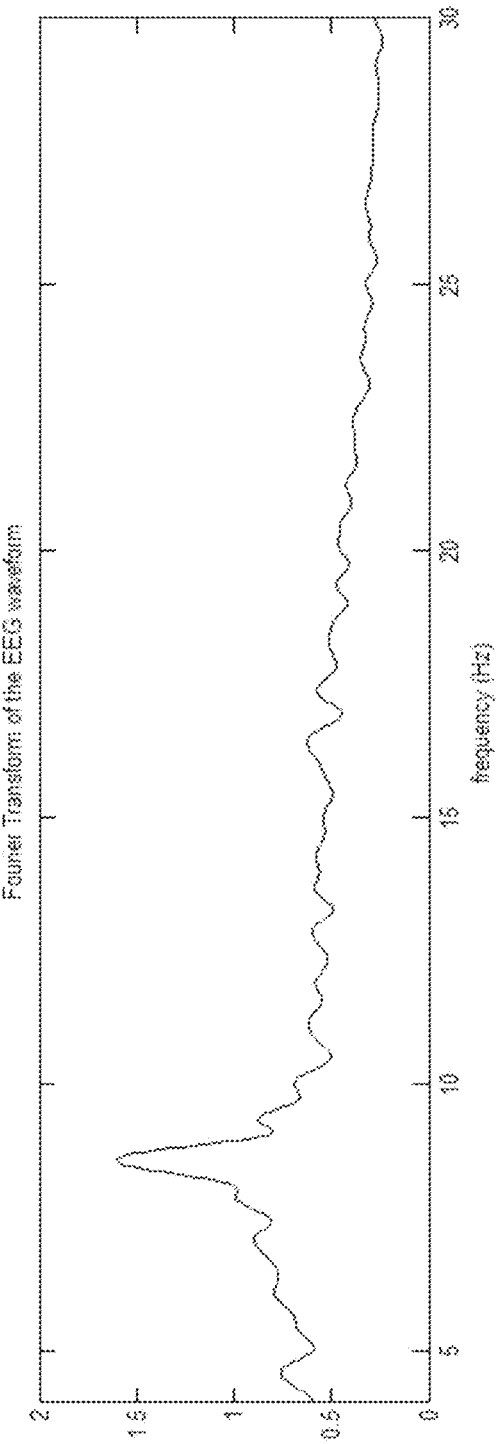
FIG. 38b shows the Fast Fourier Transformation of EEG data of FIG. 38a which is an example EEG waveform for a subject having Major Depressive Disorder.
Figure 38C:
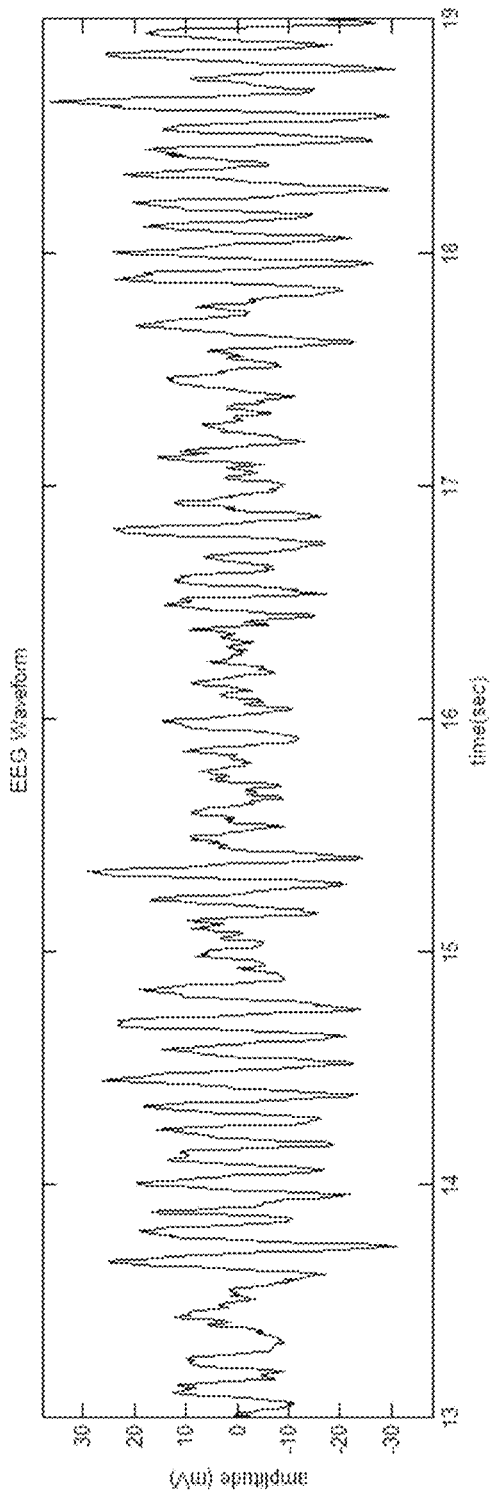
FIG. 38c shows an example EEG waveform for a subject who does not have Major Depressive Disorder.
Figure 38D:
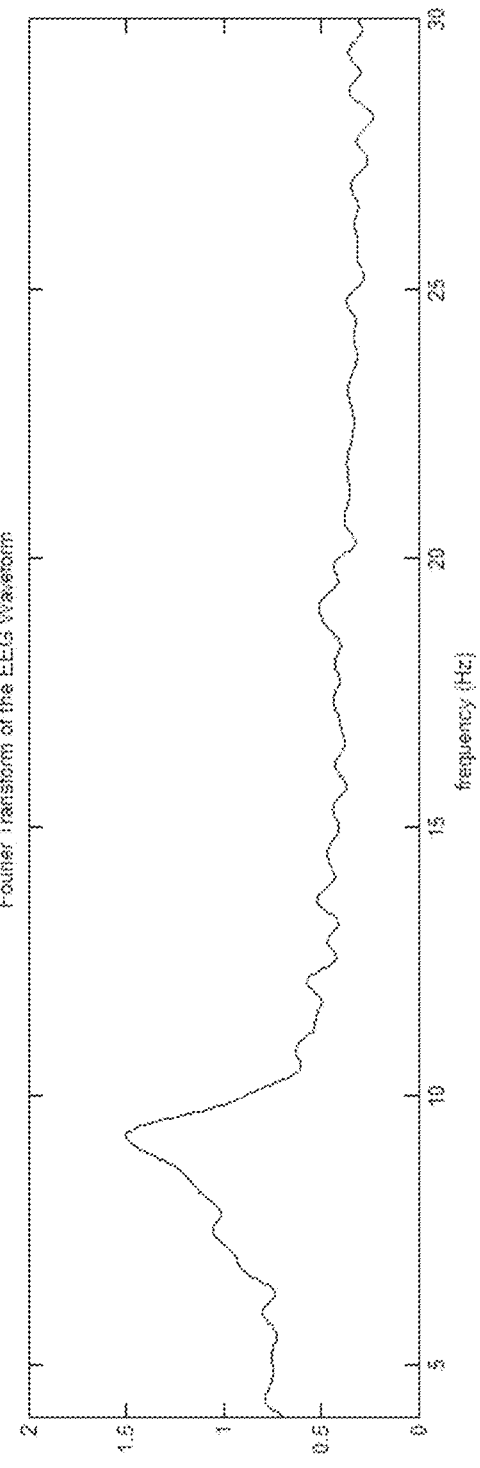
FIG. 38d shows the Fast Fourier Transformation of EEG data of FIG. 38c which is an example EEG waveform for a subject who does not have Major Depressive Disorder.

FIG. 38a-38d show EEG waveforms (CZ location) and frequency plots of two patients, which show a different focus of activity around the alpha frequency. FIG. 38a shows an example EEG waveform for a subject having Major Depressive Disorder (with time in seconds on the x-axis, and amplitude in mV on the y-axis). FIG. 38b shows the Fast Fourier Transformation of EEG data of FIG. 38a which is an example EEG waveform for a subject having Major Depressive Disorder (with a measure of energy shown on the y-axis, and frequency in Hertz shown on the x-axis). FIG. 38c shows an example EEG waveform for a subject who does not have Major Depressive Disorder (with time in seconds on the x-axis, and amplitude in mV on the y-axis). FIG. 38d shows the Fast Fourier Transformation of EEG data of FIG. 38c which is an example EEG waveform for a subject who does not have Major Depressive Disorder (with a measure of energy shown on the y-axis, and frequency in Hertz shown on the x-axis). While the plots in FIGS. 38a-38d are taken from individuals having MDD and/or not having MDD, the waveforms alone are not necessarily indicative or dispositive of having MDD, although they may be. Each individual should be diagnosed according to diagnostic norms, and not necessarily diagnosed based on the waveforms of their brain EEG data. A subject who does not have MDD may have a EEG waveform such as shown in FIG. 38a. Likewise, a subject who has MDD may have an EEG waveform such as shown in FIG. 38c, and treating such a subject with a device and or by a method provided herein may still provide the improvement in their depression noted herein by shifting their intrinsic frequency, changing their Q factor, and/or changing their coherence, etc. Each subject should be treated as an individual, and changes to their EEG waveforms are relative to their own starting EEG waveforms. Nevertheless, generally speaking, a population of subjects having MDD might have waveforms more rhythmic than that of a population of subjects not having MDD.

Figure 12:
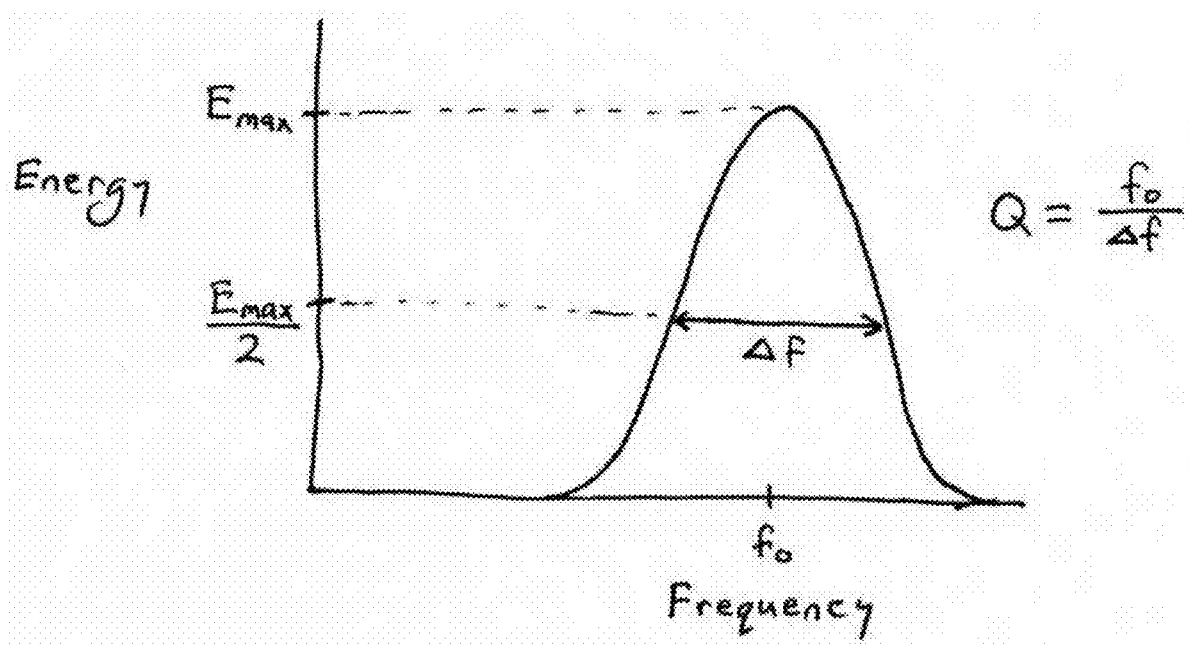
FIG. 12 shows an example of the Q-factor as used in this invention. The figure shows a sample graph of the frequency distribution of the energy of an EEG signal. It can be seen that a frequency range, $\Delta f$ can be defined as the frequency bandwidth for which the energy is above one-half the peak energy. The frequency $f_0$ is defined as the intrinsic frequency in the specified band. The Q-factor is defined as the ratio of $f_0/\Delta f$. As can be seen, when $\Delta F$ decreases for a given $f_0$, the Q-factor will increase. This can occur when the peak energy $E_{max}$ of the signal increases or when the bandwidth of the EEG signal decreases.

This focusing of the energy in the band can be quantified by the Q factor of the Fourier transform. Q factor represents the ratio of the total energy of a system stored divided by the energy lost in a single oscillation of the system. It can be characterized by the equation for Q depicted in FIG. 12, where f0 is the alpha frequency and $\Delta f$ is the bandwidth, the width of the range of frequencies for which the system energy is at least half its peak value. FIG. 12 also shows a pictorial example of the elements of Q factor. In the plot shown in FIG. 12, f0 is the alpha frequency and $\Delta f$ is the bandwidth at half energy Emax.

Q factor gives a representation of the resonance of an oscillatory system. If the system has a high Q, then it has high resonance, and tends to oscillate with very little loss in energy. A physical example for this type of system would be a pendulum, which can oscillate for a long time with no external energy input. A system with a low Q, however, has much less resonance, and may be considered to be damped.

Figure 39A:
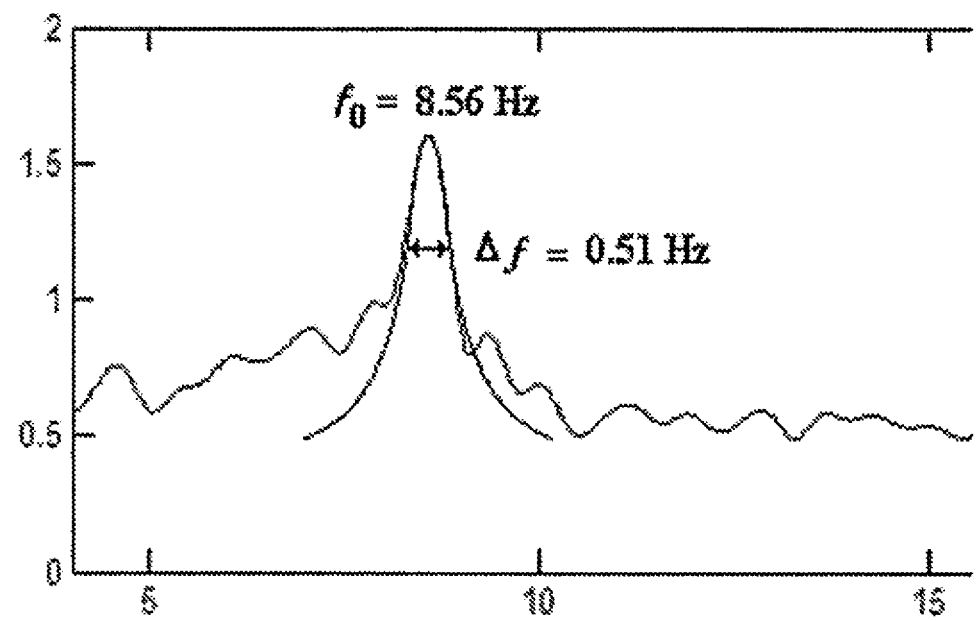
FIG. 39a shows the Fast Fourier Transformation curve of EEG data of an example EEG waveform for a subject having Major Depressive Disorder, also depicted in FIG. 38b, and shows the fitted Gaussian curve of the Fast Fourier Transformation curve having an intrinsic frequency of 8.56 Hz, and having a delta f (Δf) of 0.51 Hz.
Figure 39B:
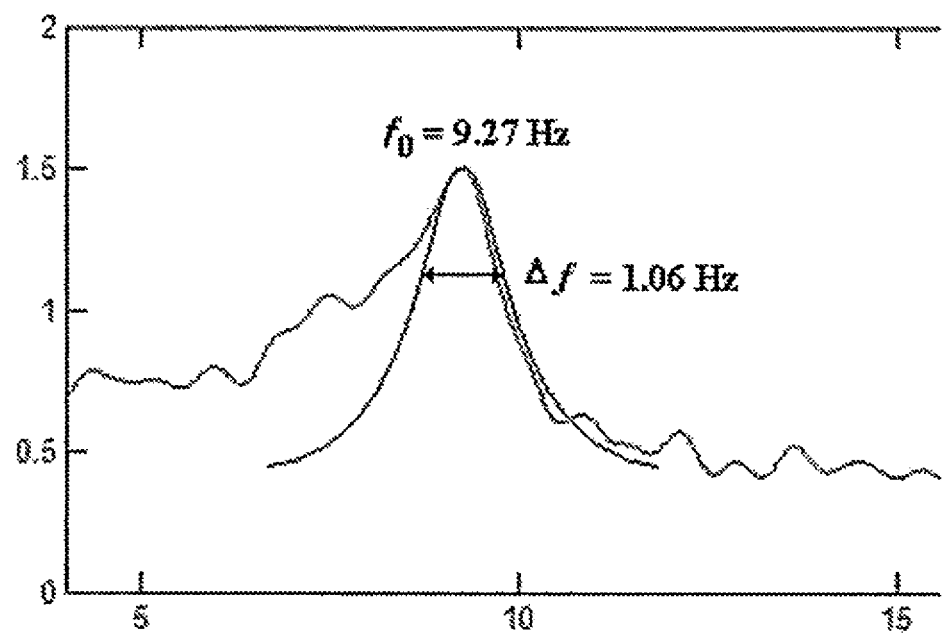
FIG. 39b shows the Fast Fourier Transformation curve of EEG data of an example EEG waveform for a subject who does not have Major Depressive Disorder, also depicted in FIG. 38d, and shows the fitted Gaussian curve of the Fast Fourier Transformation curve having an intrinsic frequency of 9.27 Hz, and having a delta f (Δf) of 1.06 Hz.

The Q factor of the EEG waveform can be represented by fitting a Gaussian-shaped curve to the frequency plot, as shown in FIG. 39a, and FIG. 39b (having a measure of energy shown on the y-axes of these plots, and frequency in Hertz shown on the x-axis of these plots). In this, $\Delta f$ is defined as the bandwidth at 0.7071 of the maximum amplitude, because the energy of a system is proportional to the square of the Fourier transform. The high-Q EEG has significantly more resonance, and therefore less energy consumption, than the low-Q EEG. It can be stated, therefore, that the region of cortex underneath the electrode requires less energy, and therefore has a lower metabolism, for the high-Q patient than the low-Q patient.

FIG. 39a, and FIG. 39b depict the frequency plots from FIG. 38b, and FIG. 38d, respectively, with a fitted Gaussian waveforms shown. FIG. 39a shows the fitted Gaussian curve of the Fast Fourier Transformation curve having an intrinsic frequency of 8.56 Hz, and having a delta f ($\Delta f$) of 0.51 Hz. The Q factor of the fitted Gaussian curve peak is in FIG. 39a is 16.78.

FIG. 39b shows the Fast Fourier Transformation curve of EEG data of an example EEG waveform for a subject who does not have Major Depressive Disorder, also depicted in FIG. 38d, and shows the fitted Gaussian curve of the Fast Fourier Transformation curve having an intrinsic frequency of 9.27 Hz, and having a delta f ($\Delta f$) of 1.06 Hz. The Q factor of the fitted Gaussian curve peak is in FIG. 39a is 7.74.

The power of the alpha band relative to other bands is generally higher for patients with MDD. Since the overall metabolism of the brain is generally constant, the increase in alpha power will result in a higher alpha Q factor, which indicates a lower metabolism, and energy, of the cortex.

Patients with MDD usually have lower metabolism in the cortex, especially in the frontal regions, therefore the Q factor of alpha EEG in those regions will be high, indicative of a low-energy system. FIG. 40 shows a general relationship between the measures of neural activity in the cortex (frontal cortex) and a possible indication for Major Depressive Disorder (MDD).

Lowering the Q factor of patients with MDD may improve MDD symptoms in some patients. The methods and devices provided herein can lower the Q factor of a subject.

The brain is a non-linear resonant system. To increase the resonance, and thereby the Q factor of the system, an alternating magnetic field may be applied that matches the alpha frequency. To decrease the resonance and lower the Q factor, an alternating magnetic field is applied that is slightly off the alpha frequency. Since the brain is a resonant system, the magnetic field does not need to be large. It is not necessary, in some embodiments, to actively cause current to flow in the brain.

The low energy sinusoidal alternating magnetic field creates a low voltage alternating electric field in the tissue, but any current created directly is negligible. The methods and devices provided herein, in some embodiments, "encourage" firing at the magnetic field frequency by causing the baseline potential across the neuron to vary slightly in time with the electric field. The variation of the potential can be subthreshold, which will not induce any neuronal firing. In some embodiments, if the magnetic field frequency matches the alpha frequency of a region of cortex, the Q factor of that region will increase. If it does not match, in some embodiments, the Q factor will decrease.

Alpha frequency in the brain is not constant, however, and can change from one moment to the next, and can vary spatially throughout the brain. Therefore, applying an alternating magnetic field at a single frequency will increase resonant behavior at some times and locations, and decrease it at others. As noted in examples described herein, single alternating magnetic field at a single calculated average frequency may reduce the overall Q factor of the cortex if the Q factor was high before treatment began, and may increase the Q factor if the Q factor was low before treatment began.

If the brain was a linear resonator, one would be unable to change the Q factor simply by applying an external magnetic field. Once the magnetic field was turned off, it might be expected that the brain to return to its original state. Instead, however, as shown in examples mentioned herein using the methods and devices provided herein, the brain adjusts its Q factor a small amount due to the applied magnetic field, and that adjustment is additive as therapy progresses.

Application of a low energy alternating magnetic field near the head of a patient suffering from MDD (i.e., the patient has a high Q factor) with the magnetic field frequency equal to the average alpha frequency should result in a decrease in the patient's Q factor. The decrease in Q factor causes the cortex to be higher energy, which causes a decrease in the symptoms of MDD.

In some embodiments, treatment of MDD with devices and methods provided herein are designed to create low energy alternating magnetic fields at a specific frequency in the alpha band.

In some embodiments, the pre-selected EEG phase is lower than the EEG phase between the two sites in the brain of the subject. In some embodiments, the pre-selected EEG phase is any EEG phase lower than the EEG phase between the two sites in the brain of the subject. In some embodiments, the pre-selected EEG phase is higher than the EEG phase between the two sites in the brain of the subject. In some embodiments, the pre-selected EEG phase is any EEG phase higher than the EEG phase between the two sites in the brain of the subject. In some embodiments, the pre-selected EEG phase is an EEG phase of a population of people. The population of people may be a set of people having a particular trait, characteristic, ability, or feature. The population may be a healthy population of people. The population of people may be a set of people not having a particular disorder, such as anxiety, depression, or other disorders mentioned herein. In some embodiments, the methods comprise measuring EEG data of two sites in the brain of the subject, and calculating the EEG phase between the two sites in the brain of a subject. The specified EEG frequency may be an intrinsic frequency as described herein. The specified EEG frequency may be a pre-selected frequency as described herein. The pre-selected frequency may be an average intrinsic frequency of a healthy population database within a specified EEG band.

In another aspect are methods for influencing an EEG phase of a specified EEG frequency between multiple locations of a brain of a subject, comprising: (a) determining the EEG phase the between at least two locations measured on the head of the subject; (b) comparing the EEG phase from step (a) to an average EEG phase of a healthy population; and (c) applying a magnetic field close to a head of the subject wherein applying the magnetic field influences the determined EEG phase toward the average EEG phase of a healthy population.

In another aspect are methods for using a Transcranial Magnetic Stimulation (TMS) device for influencing an EEG phase of a subject of a specified EEG frequency, comprising: (a) adjusting output of said TMS device; (b) changing the EEG phase by repetitive firing of at least one magnetic field using said TMS device; and (c) applying said magnetic field close to a head of the subject.

FIG. 1 shows an exemplary device having a magnet 2 coupled to and rotated by a motor 72 in which the magnet 2 rotates so that the plane of rotation is generally perpendicular to the surface of the scalp of the subject 6, and the rotation axis 36 is generally parallel to at least a portion of the surface of the scalp of the subject 6. The motor 72 is coupled to the magnet 2 by a drive shaft 4, and the magnet rotation is controlled by a controller 58 (i.e. controller subunit) that can at least monitor and/or control the rotation of the magnet 2. Control of the rotation may include, for non-limiting example, the speed of rotation, and the acceleration and/or deceleration of rotation, the time of rotation, and the direction of rotation (e.g. clockwise, counter-clockwise).

Figure 2:
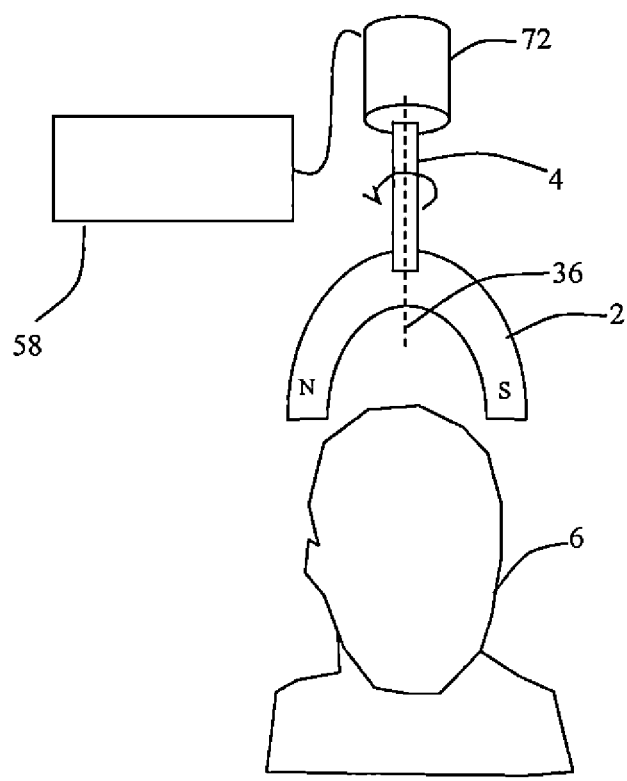
FIG. 2 shows an exemplary device in which a horseshoe magnet is positioned such that the plane of rotation is parallel to the surface of the scalp.

FIG. 2 shows an exemplary device in which a magnet 2 in the shape of a horseshoe is coupled to and rotated by a motor 72, and the magnet 2 is positioned such that the plane of rotation is generally parallel to at least a portion of the surface of the scalp of the subject 6, and the rotation axis 36 is generally perpendicular to at least a portion of the surface of the scalp of the subject 6. The motor 72 is coupled to the magnet 2 by a drive shaft 4, and the magnet rotation is controlled by a controller 58 (i.e. controller subunit) that can at least monitor and/or control the rotation of the magnet 2. Control of the rotation may include, for non-limiting example, the speed of rotation, and the acceleration and/or deceleration of rotation, the time of rotation, and the direction of rotation (e.g. clockwise, counter-clockwise).

Figure 3:
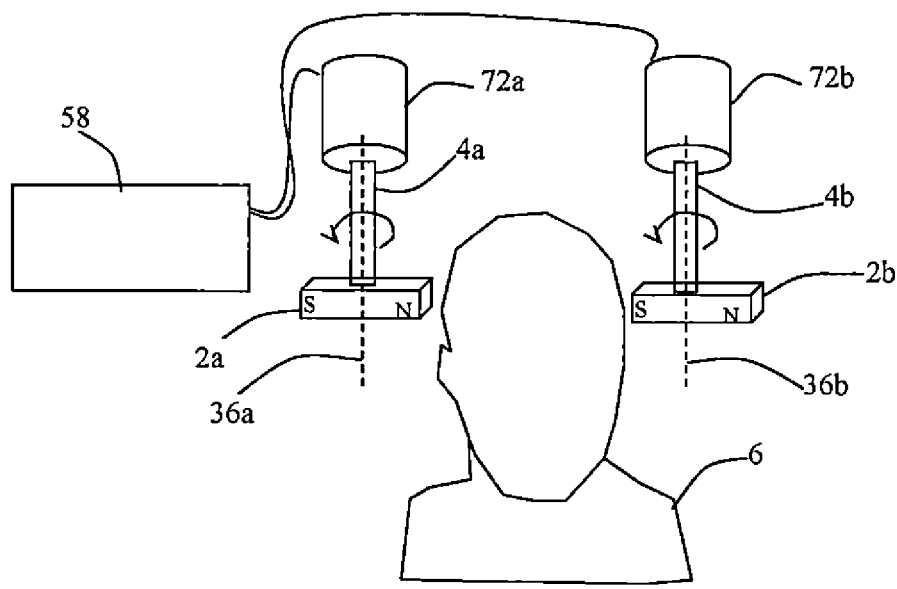
FIG. 3 shows an exemplary device which two bar magnets are rotated synchronously to provide a more uniform phase for the magnetic field in the brain.

FIG. 3 shows an exemplary device which two bar magnets 2a, 2b are coupled to and rotated by motors 72a, 72b, and the magnets 2a, 2b are rotated synchronously to provide a more uniform phase for the magnetic field in the brain of a subject 6. The motors 72a, 72b are coupled to the magnets 2a, 2b, respectively, by a drive shafts 4a, 4b, and the rotation of the magnets 2a and 2b about rotation axes 36a, 36b, respectively, is controlled by a controller 58 (i.e. controller subunit) that can at least monitor and/or control the rotation of the magnet 2a, 2b. Control of the rotation of the magnets may include, for non-limiting example, the speed of rotation, and the acceleration and/or deceleration of rotation, the time of rotation, and the direction of rotation (e.g. clockwise, counter-clockwise). The rotation of a single magnet (magnet 2a, for example), may be controlled independently from and/or simultaneously with the rotation of a second magnet (magnet 2b, for example) by the controller 58. Additional magnets may be similarly added to the device. In another embodiment, a single motor is coupled to a plurality of magnets, and each of the magnets may be controlled by the controller, independently or simultaneously.

In some embodiments, the magnetic field used by the methods or devices are not capable of exciting brain cells. In some embodiments, the magnetic field used by the methods or devices are below thresholds of exciting brain cells. In some embodiments, the devices described can have one or more permanent magnets mounted onto one or more rotating shafts in such a way that it creates an alternating magnetic field when the shaft or shafts are spun. In some embodiments, the speed of rotation can be set by the user or controlled using neurological feedback to provide optimal therapy.

Methods and devices described herein can be used to treat at least one mental disorder listed below:
(a) Major depression;
(b) Bipolar disorder;
(c) Schizophrenia;
(d) Anxiety disorder;
(e) Obsessive-Compulsive disorder;
(f) ADHD;
(g) Autism;
(h) Sleep disorder;
(j) Parkinson's disease;
(k) Drug addiction;
(l) Substance abuse;
(m) Seizure;
(n) Head Injury;
(o) Alzheimer's disease;
(p) Eating disorder;
(q) Tinnitus; and
(r) Fibromyalgia.

Certain types of neuropathic pain may also be treated with the devices and methods provided herein. This may include, for nonlimiting example occipital neuralgia (affecting the head), neuritis (inflammation of a nerve), trigeminal neuralgia (affecting the facial areas), peripheral neuralgia, sciatic neuralgia (sciatica), intercostal neuralgia (affecting the ribs), postherpetic neuralgia (related to shingles), diabetic neuropathy, and glossopharyngeal neuralgia (affecting the tongue and throat). In some embodiments, the devices and methods provided herein are adapted to treat Psychalgia (psychogenic pain).

Likewise, certain types of neurologic disorders may be treated with the devices and methods provided herein. Neurological disorders can be categorized according to the primary location affected, the primary type of dysfunction involved, or the primary type of cause. The broadest division is between central nervous system (CNS) disorders and peripheral nervous system (PNS) disorders. Brain, spinal cord and nerve disorders may be described in several overlapping categories. These categories include brain neurological disorders, spinal cord disorders, peripheral nervous system disorders, cranial nerve disorders, autonomic nervous system disorders, seizure disorders such as epilepsy, movement disorders such as Parkinson's disease, sleep disorders, headaches such as migraine, lower back and neck pain, other generalized neuropathic pain, delirium and dementia such as Alzheimer's disease, dizziness and vertigo, stupor and coma, head injury, stroke including CVA and cerebrovascular attack, multiple sclerosis and other demyelinating diseases, infections of the brain or spinal cord including meningitis, prion diseases, and complex regional pain syndrome (CRPS) which is a chronic pain condition.

Brain neurological disorders may be further categorized into brain damage and brain dysfunction. Brain damage includes damage according to cerebral lobe (including lower brain areas such as basal ganglia, cerebellum, brainstem), and may include Frontal lobe damage, Parietal lobe damage, Temporal lobe damage, and Occipital lobe damage. Brain dysfunction includes aphasia (affecting language), dysarthria (affecting speech), apraxia (affecting patterns or sequences of movements), agnosia (affecting identification of things or people), and amnesia (affecting memory).

In some embodiments, methods and devices described herein can be used to treat at least two mental disorders listed above. In some embodiments, methods and devices described herein can be used to treat at least three mental disorders listed above. In some embodiments, methods and devices described herein can be used to treat at least four mental disorders listed above. In some embodiments, methods and devices described herein can be used to treat at least five mental disorders listed above. In some embodiments, methods and devices described herein can be used to treat at least six mental disorders listed above. In some embodiments, methods and devices described herein are not used to treat schizophrenia.

In another aspect are methods of treating anxiety in a subject, comprising tuning up the Q-factor of an intrinsic frequency of the subject by applying a magnetic field close to a head of the subject, wherein the magnetic field comprises at least one of (a) a single pre-selected frequency; (b) a plurality of frequencies within a specified EEG band; and (c) an intrinsic frequency of a brain of the subject within a specified EEG band. In some embodiments, any of the devices described herein may be used to treat anxiety.

In some embodiments, are method of treating depression in a subject, comprising tuning down the Q-factor of an intrinsic frequency of the subject by applying a magnetic field close to a head of the subject, wherein the magnetic field comprises at least one of (a) a single frequency; (b) a plurality of frequencies within a specified EEG band; and (c) an intrinsic frequency of a brain of the subject within a specified EEG band. In some embodiments, any of the devices described herein may be used to treat depression.

In some embodiments, methods and/or devices as described herein can be used to treat symptoms of fibromyalgia. In some embodiments, methods and/or devices as described herein can be used to improve symptoms of fibromyalgia. For non-limiting example, some symptoms that may be improved include widespread pain, tenderness to touch, nausea dizziness, temporomandibular joint dysfunction, skin problems, depression, myofascial pain, morning stiffness, sleep issues, headaches, chemical sensitivity, dysmenorrhea, muscle twitches and weakness, fatigue, urinary and pelvic problems, fibro-fog cognitive and/or memory impairment, anxiety, memory loss, breathing problems, and vision problems.

Certain types of neuropathic pain may also be treated with the devices and methods provided herein. This may include, for nonlimiting example occipital neuralgia (affecting the head), neuritis (inflammation of a nerve), trigeminal neuralgia (affecting the facial areas), peripheral neuralgia, sciatic neuralgia (sciatica), intercostal neuralgia (affecting the ribs), postherpetic neuralgia (related to shingles), diabetic neuropathy, and glossopharyngeal neuralgia (affecting the tongue and throat). In some embodiments, the devices and methods provided herein are adapted to treat Psychalgia (psychogenic pain).

Likewise, certain types of neurologic disorders may be treated with the devices and methods provided herein. Neurological disorders can be categorized according to the primary location affected, the primary type of dysfunction involved, or the primary type of cause. The broadest division is between central nervous system (CNS) disorders and peripheral nervous system (PNS) disorders. Brain, spinal cord and nerve disorders may be described in several overlapping categories. These categories include brain neurological disorders, spinal cord disorders, peripheral nervous system disorders, cranial nerve disorders, autonomic nervous system disorders, seizure disorders such as epilepsy, movement disorders such as Parkinson's disease, sleep disorders, headaches such as migraine, lower back and neck pain, other generalized neuropathic pain, delirium and dementia such as Alzheimer's disease, dizziness and vertigo, stupor and coma, head injury, stroke including CVA and cerebrovascular attack, multiple sclerosis and other demyelenating diseases, infections of the brain or spinal cord including meningitis, prion diseases, and complex regional pain syndrome (CRPS) which is a chronic pain condition.

Brain neurological disorders may be further categorized into brain damage and brain dysfunction. Brain damage includes damage according to cerebral lobe (including lower brain areas such as basal ganglia, cerebellum, brainstem), and may include Frontal lobe damage, Parietal lobe damage, Temporal lobe damage, and Occipital lobe damage. Brain dysfunction includes aphasia (affecting language), dysarthria (affecting speech), apraxia (affecting patterns or sequences of movements), agnosia (affecting identification of things or people), and amnesia (affecting memory).

In some embodiments, methods and/or devices as described herein can be used to halt the onset of a seizure. In some embodiments, methods and/or devices as described herein can be used to prevent the onset of a seizure. In some embodiments, methods and/or devices as described herein can be used to reduce or eliminate seizures by detuning the brain near the frequency of the seizures. In some embodiments, methods and/or devices as described herein can be used to reduce or eliminate seizures by tuning up an area of the brain (i.e., an intrinsic frequency in a band, such as alpha) different than the seizure area of the brain, thereby reducing the energy in the frequency associated with the seizure. The seizure may be caused by various conditions, diseases, injuries, and/or other factors. For non-limiting example, the conditions may include abnormalities in the blood vessels of the brain, atherosclerosis, or hardening of the arteries supplying the brain, bleeding into the brain, such as a subarachnoid hemorrhage, brain tumors, chromosomal abnormalities, congenital diseases or conditions, high blood pressure, pregnancy and problems associated with pregnancy, stroke, transient ischemic attack (mini-stroke). For non-limiting example, the diseases may include liver disease, Alzheimer's disease, dementia diseases, epilepsy, nervous system diseases, hereditary diseases, infections involving the brain, encephalitis, brain abscess, bacterial meningitis, kidney failure, and chronic renal failure. For non-limiting example, the injuries may include choking, head injuries, electrical injuries, birth injuries, poisonous bites or stings.

Methods and devices described herein can be used to improve at least one indication selected from the group consisting of replacement for meditation, quick nap, stress release, attention span, comprehension, memory, lowered blood pressure, increased libido, sports performance, academic performance, and any combination thereof. In some embodiments, methods and devices described herein can be used to improve at least two indications from the group presented above. In some embodiments, methods and devices described herein can be used to improve at least three indications from the group presented above. In some embodiments, methods and devices described herein can be used to improve at least four indications from the group presented above. In some embodiments, methods and devices described herein can be used to improve at least five indications from the group presented above. In some embodiments, methods and devices described herein can be used to improve at least six indications from the group presented above.

In some embodiments, methods and devices described herein can be used to improve at least one indication from the group presented above, and at least one mental disorder listed above. In some embodiments, methods and devices described herein can be used to improve at least one indication from the group presented above, and at least two mental disorders listed above. In some embodiments, methods and devices described herein can be used to improve at least two indications from the group presented above, and at least one mental disorder listed above. In some embodiments, methods and devices described herein can be used to improve at least two indications from the group presented above, and at least two mental disorders listed above. In some embodiments, methods and devices described herein can be used to improve at least one indication from the group presented above, and at least three mental disorders listed above. In some embodiments, methods and devices described herein can be used to improve at least two indications from the group presented above, and at least three mental disorders listed above. In some embodiments, methods and devices described herein can be used to improve at least three indications from the group presented above, and at least three mental disorders listed above. In some embodiments, methods and devices described herein can be used to improve at least three indications from the group presented above, and at least two one mental disorders listed above.

Methods and devices described herein can be used to improve at least one characteristic selected from the group consisting of peripheral visual response, attention span, immediate reaction time (IRT), movement time (MT), simple perceptual reaction time (SPR), conflict perceptual reaction time (CPR), and any combination thereof. In some embodiments, methods and devices described herein can be used to improve at least two indications from the group presented above. In some embodiments, methods and devices described herein can be used to improve at least three indications from the group presented above. In some embodiments, methods and devices described herein can be used to improve at least four indications from the group presented above. In some embodiments, methods and devices described herein can be used to improve at least five indications from the group presented above. In some embodiments, methods and devices described herein can be used to improve at least six indications from the group presented above.

In some embodiments, methods and devices described herein can be used to improve at least one characteristic from the group presented above, and at least one mental disorder listed above. In some embodiments, methods and devices described herein can be used to improve at least one characteristic from the group presented above, and at least two mental disorders listed above. In some embodiments, methods and devices described herein can be used to improve at least two characteristics from the group presented above, and at least one mental disorder listed above. In some embodiments, methods and devices described herein can be used to improve at least two characteristics from the group presented above, and at least two mental disorders listed above. In some embodiments, methods and devices described herein can be used to improve at least one characteristic from the group presented above, and at least three mental disorders listed above. In some embodiments, methods and devices described herein can be used to improve at least two characteristics from the group presented above, and at least three mental disorders listed above. In some embodiments, methods and devices described herein can be used to improve at least three characteristics from the group presented above, and at least three mental disorders listed above. In some embodiments, methods and devices described herein can be used to improve at least three characteristics from the group presented above, and at least two one mental disorders listed above.

In some embodiments, methods and devices described herein can be used to improve at least one characteristic from the group presented above, and at least one indication presented above. In some embodiments, methods and devices described herein can be used to improve at least one characteristic from the group presented above, and at least two indications presented above. In some embodiments, methods and devices described herein can be used to improve at least two characteristics from the group presented above, and at least one indication presented above. In some embodiments, methods and devices described herein can be used to improve at least two characteristics from the group presented above, and at least two indications presented above. In some embodiments, methods and devices described herein can be used to improve at least one characteristic from the group presented above, and at least three indications presented above. In some embodiments, methods and devices described herein can be used to improve at least two characteristics from the group presented above, and at least three indications presented above. In some embodiments, methods and devices described herein can be used to improve at least three characteristics from the group presented above, and at least three indications presented above. In some embodiments, methods and devices described herein can be used to improve at least three characteristics from the group presented above, and at least two one indications presented above.

Methods and devices described herein can be used to provide an improvement to a mental disorder as measured using a rating scale selected from the group consisting of HAMA, HAMD, PANSS, MADRS, BARS, SAS, and any combination thereof. In some embodiments of at least one aspect described above, the method provides an improvement as measured using the Unified Parkinson's Rating Scale. In some embodiments of at least one aspect described above, the method provides an improvement as measured using a modified Unified Parkinson's Rating Scale. The modified Unified Parkinson's Rating Scale may include, for non-limiting example, measuring muscle tone and knee/arm flexibility.

In some embodiments, the pMERT (permanent Magneto-EEG Resonant Therapy) device (i.e. the NEST device) comprises one or more powerful magnets (>5000 G each) that rotate at a specific frequency or frequencies to bring about the desired therapy. A single, dual, or multi-channel EEG is incorporated in the device to acquire a sample EEG segment and determine the alpha frequency distribution. From this information, the device controls the frequency of rotation of the magnet or magnets to deliver therapy.

Figure 4:
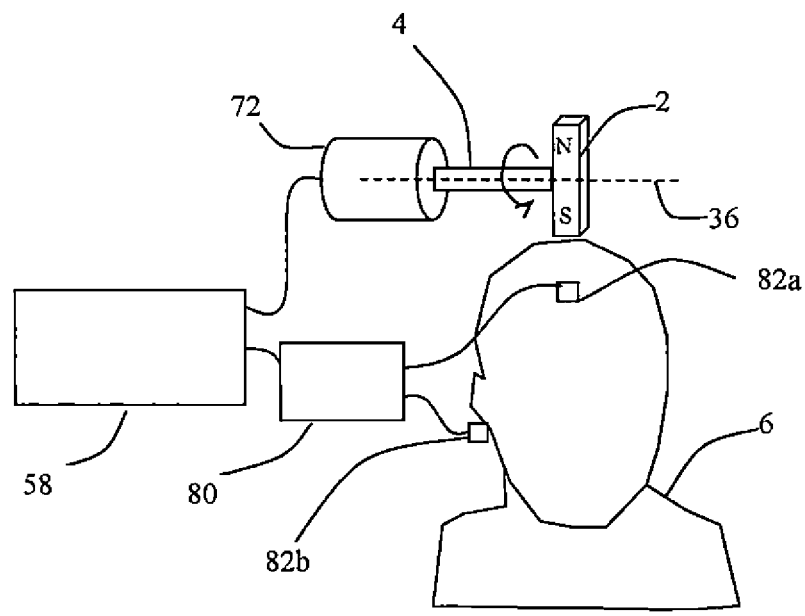
FIG. 4 shows an exemplary device in which the magnet rotates so that the plane of rotation is perpendicular to the surface of the scalp and a pair of electrodes is used to record the EEG of the patient.

FIG. 4 shows an exemplary device in which the magnet 2 rotates so that the plane of rotation is generally perpendicular to the surface of the scalp of a subject 6 and a bio-feedback sensor and/or EEG electrode 82a is used to control the speed of rotation about the rotation axis 36. The rotation of the magnet 2 is driven by a motor 72 which is coupled to a drive shaft 4, and the drive shaft 4 is coupled to the magnet 2. In some embodiments at least two EEG electrodes, 82a, 82b are used to control the speed of rotation, wherein at least one EEG electrode, for example EEG electrode 82b, is used as a reference electrode (and/or a ground electrode). The electrodes, 82a, 82b may be connected to an amplifier 80 which can amplify the signal received from the electrodes, 82a, 82b. The magnet rotation may be controlled and/or monitored by a controller subunit (controller), 58, which may also receive, record, and/or display the signal or signals received from the EEG electrodes 82a, 82b. In some embodiments, the reading from a reference EEG electrode, for example EEG electrode 82b, is subtracted and/or otherwise removed from the reading from the second EEG electrode, for example EEG electrode 82a. In some embodiments, the bio-feedback sensor/EEG electrode is used, at least in part, to determine the subsequent treatment regimen for the subject.

In some embodiments, the EEG electrodes are used to measure the brain waves of the subject at various times, for non-limiting example, prior to applying a method of treatment as provided herein using a device described herein, during application of a method of treatment as provided herein using a device described herein, and/or after applying a method of treatment as provided herein using a device described herein. In some embodiments, the EEG electrodes are used to measure the brain waves of the subject at various times, for non-limiting example, prior to using a device described herein, during use of a device described herein, and/or after using a device described herein. In some embodiments, the EEG electrodes are used to measure the brain waves of the subject continuously for a specified period of time. In some embodiments the specified period of time is for non-limiting example, at least about one hour, at least about 45 minutes, at least about 40 minutes, at least about 30 minutes, at least about 20 minutes, at least about 15 minutes, at least about 10 minutes, at least about 5 minutes, at least about 1 minute, at least 30 seconds, at least about 10 seconds, at least about 5 seconds, and at least about 1 second. The term "about" when referring to the specified period of time of use of the EEG electrodes to measure brain waves can mean variation of, for example, 1 minute to 5 minutes, 30 seconds to 1 minute, 15 seconds to 30 seconds, 5 seconds to 15 seconds, 1 second to 10 seconds, 1 second to 5 seconds, 0.5 seconds to 1 second, and 0.1 seconds to 0.5 second.

In some embodiments, the intrinsic frequency of the subject is an alpha frequency of a brain of the subject. In some embodiments, alpha EEG of a brain of a subject can be critical in normal cognitive processes and the desynchronization of alpha activity can play a pathophysiological role in the mental disorders listed above. In some embodiments, the therapy using methods or systems described lasts for about 20 minutes, is very gentle, and unnoticeable to the subject. In some embodiments, the quantifiable change in alpha frequency can be seen clearly following the therapy session, and the patient may have an immediate reduction in symptoms. The therapy using methods or systems described can be mild enough to be used every day or as needed. The therapy using methods or systems described does not have to involve any medication whatsoever.

"Patient" and "subject" are synonyms, and are used interchangeably. As used herein, they mean any animal (e.g. a mammal) on which the inventions described herein may be practiced. Neither the term "subject" nor the term "patient" is limited to an animal under the care of a physician.

Figure 5:
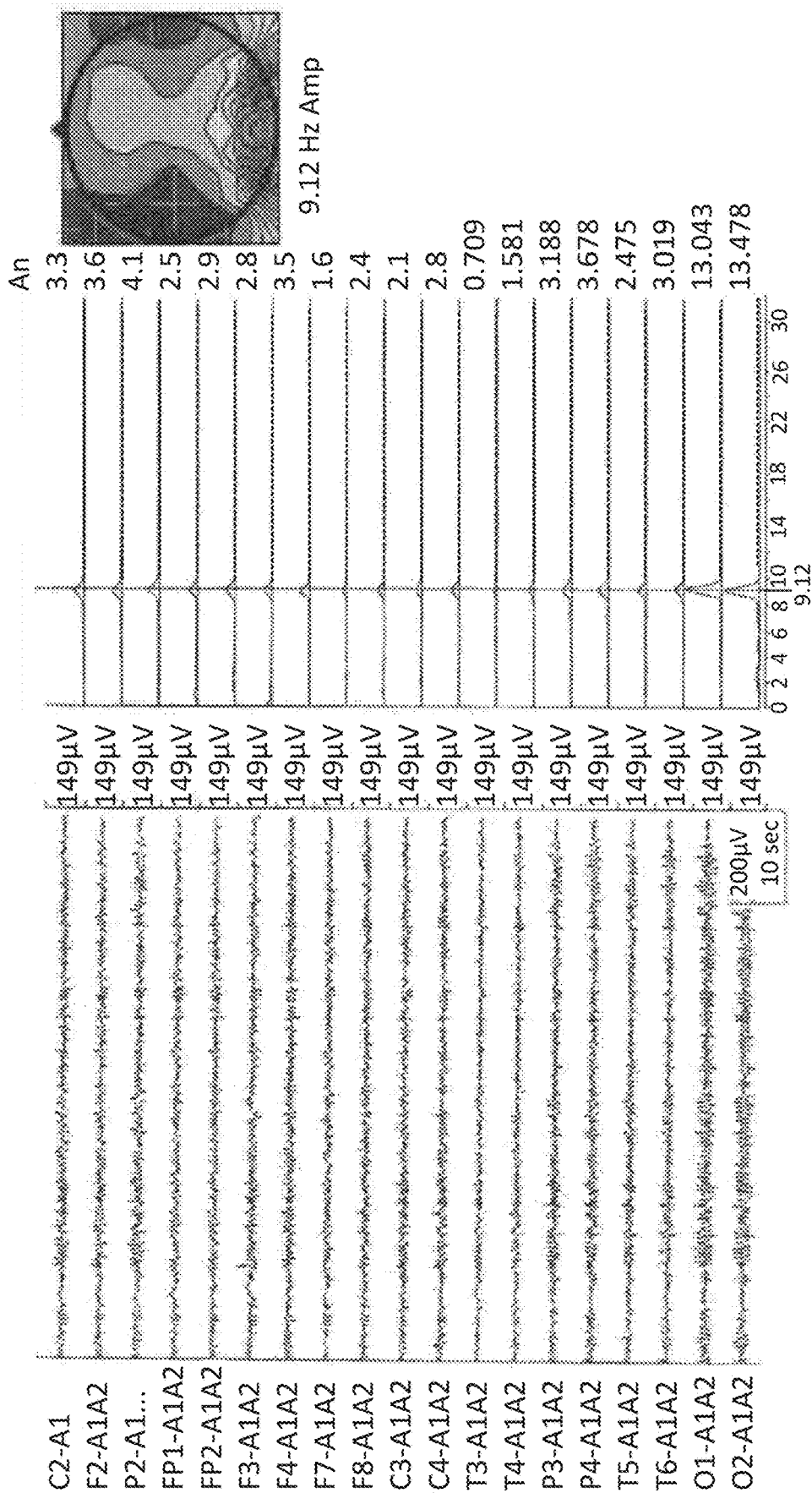
FIG. 5 shows a sample EEG segment for a subject before therapy is delivered. The block on the left shows a time series EEG while the subject is sitting at rest with eyes closed. The block in the center shows the energy across the frequency spectrum for the sampled EEG. The vertical line drawn through the peaks is at 9.1 Hz, the subject's intrinsic alpha frequency. The circle at the right shows the distribution of EEG energy at the intrinsic alpha frequency throughout the scalp, looking down on the top of the subject's head. In the circle representation, the majority of the EEG energy at the alpha frequency is concentrated at the back of the brain.

FIG. 5 shows a sample EEG segment for a subject before therapy is delivered. The block on the left shows a time series EEG while the subject is sitting at rest with eyes closed. The block in the center shows the energy across the frequency spectrum for the sampled EEG. The vertical line drawn through the peaks is at 9.1 Hz, the subject's intrinsic alpha frequency. The circle at the right shows the distribution of EEG energy at the intrinsic alpha frequency throughout the head, looking down on the top of the subject's head. In the circle representation, the majority of the EEG energy at the alpha frequency is concentrated at the back of the brain.

Figure 6:
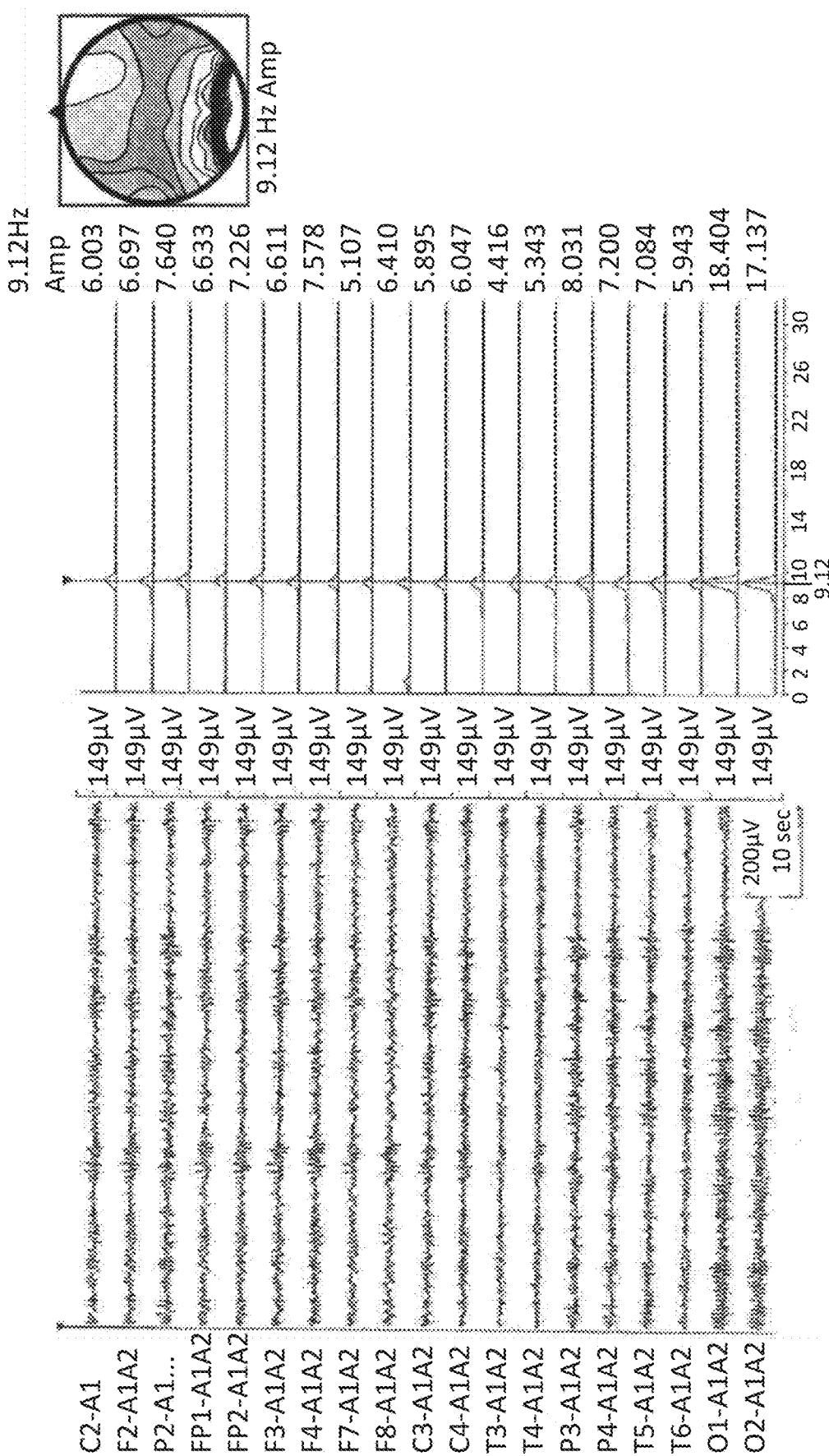
FIG. 6 is similar to FIG. 5, except the EEG was sampled immediately following therapy. In this, it can be seen that the energy associated with the intrinsic alpha frequency has increased significantly. From the circle representation on the right, it can be seen that the distribution of energy at the intrinsic alpha frequency throughout the head is more uniform, though the majority of energy is still concentrated at the back of the brain.

FIG. 6 is similar to FIG. 5, except the EEG was sampled immediately following therapy. In this, it can be seen that the energy associated with the intrinsic alpha frequency has increased significantly. From the circle representation on the right, it can be seen that the distribution of energy at the intrinsic alpha frequency throughout the head is more uniform, though the majority of energy is still concentrated at the back of the brain.

The pMERT Device (NEST Device)

Devices described may contain a plurality of magnets, and a plurality of magnets may be used to form an array to produce a desired magnetic field. Such magnetic field can be a pulsing or temporally variable unipolar magnetic field where treatments are performed with a magnetic field having a specific pole.

In some embodiments of a device or devices as described herein, the device is operable to influence an intrinsic frequency of the brain of a subject within a specified EEG band. A device as described herein may be operable to influence a Q-factor of an intrinsic frequency of the brain of a subject within a specified EEG band. A device as described herein may be operable to influence a coherence of intrinsic frequencies among multiple sites in the brain of a subject within a specified EEG band. A device as described herein may be operable to influence a EEG phase of intrinsic frequencies among multiple sites in the brain of a subject within a specified EEG band.

In some embodiments, a method of treating a subject comprises: (a) adjusting output of a magnetic field for influencing a Q-factor, a measure of frequency selectivity of a specified EEG band, of the subject toward a pre-selected or target Q-factor of the band; and (c) applying said magnetic field close to a head of the subject.

In some embodiments, devices described can comprise a substantially planar member upon which are affixed a plurality of magnets. Thus, the magnets may be oriented so as to permit application of a magnetic field having a substantially uniform polarity to a user. In some embodiments, the magnets may also be positioned on the array so that adjacent magnets have opposite polarities.

In some embodiments, the devices described may be configured so as to restrict, in one or more directions, the movement of the magnet within the devices, thereby enabling selection of the polarity of the magnetic field to which the user is subjected. For example, magnets may be placed within the devices described so that one face of the magnet is always pointing toward a head of a subject. Accordingly, the subject is subjected to a dynamic magnetic field having a specific polarity.

In some embodiments, the devices described comprise at least one rotating mechanism. In some embodiments, mechanical subunits including cams, gears and/or linkages may be utilized to move at least one magnet. These mechanical subunits may be powered through motorized means or may be connected to other devices moving in the surrounding environment which will cause the mechanical device to move the magnet. An external exciter magnet may be positioned near the devices described, where the external exciter magnet generating a sufficiently strong magnetic field to cause movement of at least one magnet contained within the devices described.

In some embodiments, magnets of the devices described can be rotated by a rotating mechanism other than a motor. In some embodiments, the devices comprise at least one orifice so that a stream of fluid such as a gas or liquid may be forced into the devices, wherein the stream of fluid being sufficiently strong so as to move at least one magnet, thus creating relative movement between the at least one magnet and a head of a subject.

While permanent magnets of any strength may be utilized for the methods and devices described herein, generally magnets having strengths within the range of about 10 Gauss to about 4 Tesla can be used. In some embodiments, the strength of at least one permanent magnet is from about 100 Gauss to about 2 Tesla. In some embodiments, the strength of at least one permanent magnet is from about 300 Gauss to about 1 Tesla.

In some embodiments, the permanent magnets for the methods and devices described comprise rare earth magnets such as neodymium, iron, boron or samarium cobalt magnets. In some embodiments, the permanent magnets for the methods and devices described are neodymium iron boron magnets. In some embodiments, ceramic magnets, electromagnets or other more powerful magnets may be utilized as they become available. In some embodiments, electromagnets may be utilized for the methods and devices described. Current can be supplied to the electromagnet by wires penetrating through the devices described and connecting to an external power source.

Described are magnetic therapeutic devices and methods for magnetic therapies where a brain of a subject is subject to at least one dynamic magnetic field having an amplitude of at least a half waveform. In certain embodiments, the treatment area is exposed to a half waveform of magnetic flux. In other embodiments, the treatment area is exposed to a full waveform of magnetic flux. Still other embodiments may permit treatment area to be exposed to either a half or full waveform. To subject the treatment area to such a dynamic magnetic field, the magnetic source may be rotated, oscillated, moved through a particular pattern, or otherwise moved relative to a head of a subject. The application area of the subject can be positioned relative to the magnetic source so that the magnetic field extends around and/or through the application area. In certain embodiments, the devices described comprise at least one magnet having a north and south magnetic pole and a pole width equal to the width of the magnet at the poles.

Three parameters of magnetic fields generated by the devices described can be manipulated:
  (a) the intensity of the magnetic field at the treatment site, which can be determined by the strength of the magnets used and the distance between the magnets and the subject's head;
  (b) the frequency of the magnetic field, i.e., the rate of change of the magnetic field, which can be determined by movements of at least one magnet, such as by varying the speed at which at least one magnet moved relative to the application area;
  (c) the amplitude of the net change in magnetic flux (or waveform) to which the application area is subjected, and
  (d) the phase of the magnetic field between two (or more) magnets (i.e. the magnetic phase) when the magnetic field frequencies of the two (or more) magnets are the same (or substantially the same).

As to the amplitude of the net change in magnetic flux, it is generally known that permanent magnets have a north pole and south pole, with north pole magnetic flux emanating from the north pole, and south pole magnetic flux emanating from the south pole. In some embodiments, the application area is subject to a "full waveform" according to the devices and methods described. For example, when a permanent magnet rotates relative to an application area, the application area may initially be subjected to a "full north pole field" where the north pole of the magnet is closest to the application area. As the north pole rotates away from the application area and the south pole rotates toward the application area, the strength of the north pole field decreases until a "neutral field" is encountered, approximately at the midpoint of the magnet. As the south pole continues to rotate toward the application area, the application area is subjected to a south pole field of increasing intensity until the south pole is closest to the application area where the application area is subjected to a "full south pole field." By rotating in this fashion, the object is subjected to a "full waveform." Likewise, the application area is also subject to a "full waveform" when the magnet rotates from the south pole to the north pole. As used herein, a south pole may also be referred to as "negative," (−), or S, and a north pole may also be referred to as "positive," (+), or N.

Figure 10A:
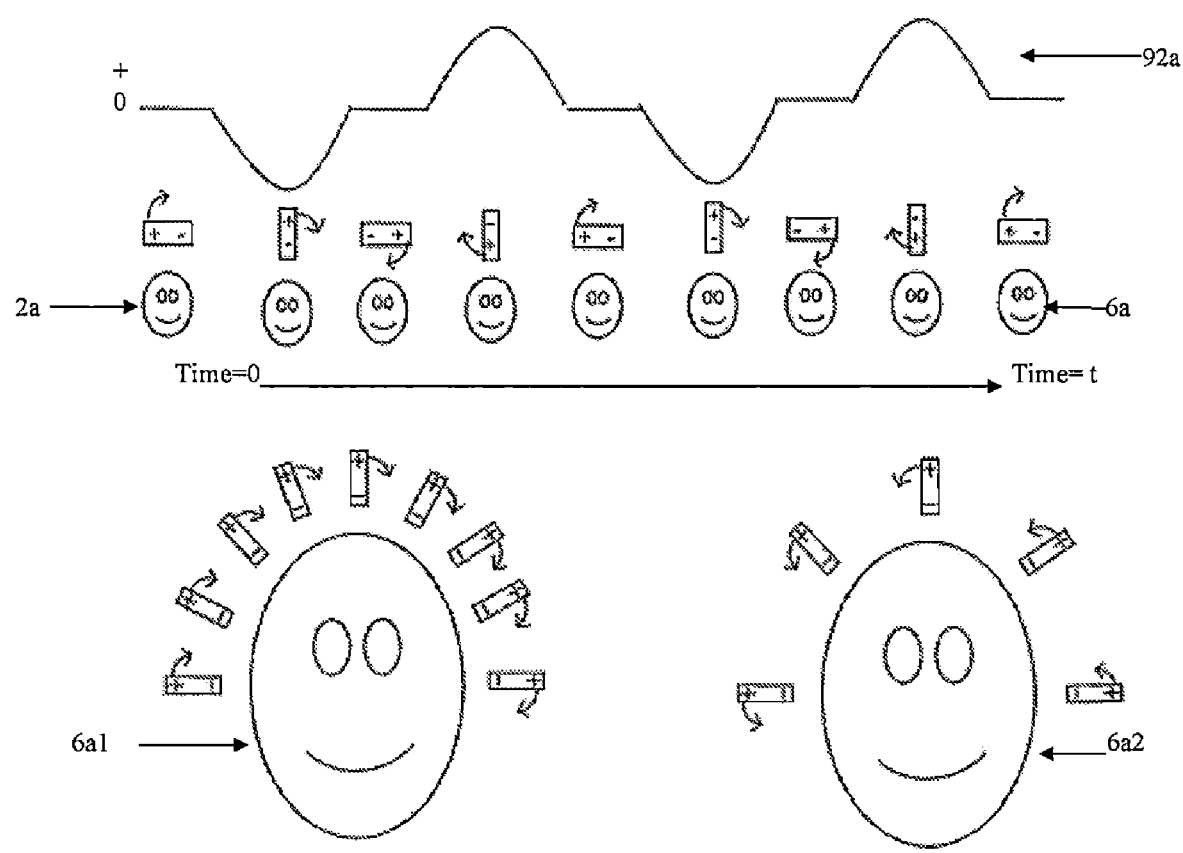
FIGS. 10A through 10G show some exemplary embodiments for various movements of at least one permanent magnet.

For example, FIG. 10A through FIG. 10G show some exemplary embodiments for various movements of at least one permanent magnet. FIG. 10A shows a graph of the magnetic field over time. That is, it shows a graph 92*a* expressing an example magnetic field experienced by a subject 6*a* as a magnet 2*a* rotation about an axis between the north pole (+) and south pole (−) of the magnet 2*a*. The position of the magnet relative to the subject 6*a* and the field strength (+ or −, amplitude can vary, depending on for example, the application, method, magnet and therapy being delivered) is shown in FIG. 10A. For example at Time=0, the subject 6*a* may experience no magnetic field (i.e. a neutral field) when the magnet's north pole is equally as far from the subject 6*a* as the magnet's south pole (assuming the north pole and south pole have equal strengths yet opposite polarities). As the magnet 2*a* spins such that the south pole of the magnet 2*a* is closest to the subject 6*a*, the subject 6*a* experiences a negative magnetic field, as shown in FIG. 10*a*, and as the magnet 2*a* spins further, the subject 6*a* is exposed to a changing magnetic field from, for example, a neutral field, to a negative field, to a neutral field, to a positive field, and so on. As further shown in FIG. 10A, an array of magnets (i.e. a plurality) may be used alternatively to a single magnet to provide a more uniform field to the subject's brain. FIG. 10A shows a subject 6*a*1 exposed to an array of nine rotating magnets, as well as a subject 6*a*2 exposed to an array of five rotating magnets. In some embodiments, any number of rotating magnets may be used to provide a more uniform field to the subject's brain.

Figure 10B:
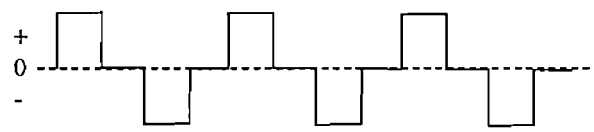
Figure 10C:
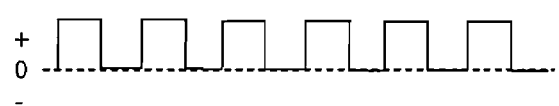
Figure 10D:
Figure 10E:
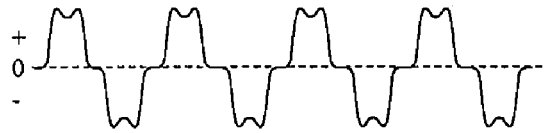
Figure 10F:
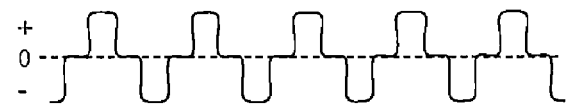
Figure 10G:
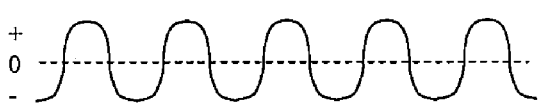

Various exemplary wave forms resulting from embodiments of the devices and methods provided herein are shown in FIG. 10B through FIG. 10G. For example, FIG. 10B shows a full waveform in the form of a step function where a magnetic field cycles through a sequence wherein the magnetic field is positive (+) then neutral, then negative (−), then neutral, and repeats. FIG. 10C shows a half waveform in the form of a step function where a magnetic field cycles through a sequence wherein the magnetic field is positive (+) then neutral, and repeating this sequence. FIG. 10D shows an alternative a half waveform in the form of a step function where a magnetic field cycles through a sequence wherein the magnetic field is positive (+) then off (or neutral), remaining off (neutral) for a longer period of time than remaining positive (+), and repeating this sequence. FIGS. 10E, 10F and 10G each show example full wave forms resulting from embodiments of a NEST device having at least one magnet wherein the magnet's, or magnets' north pole and south pole alternatively change distances from the subject in a regular pattern. By shielding a pole of the magnets of the array, half waveforms may be created using the same array of magnets, for example shielding as shown in FIG. 11C and/or FIG. 11D, discussed further below.

In some embodiments, the application area is subject to a "half waveform" according to the devices and methods described. For example, an object may be subjected to a "half waveform" where the magnet rotates relative to the application area from a full north pole field to a neutral field or from full south pole field to a neutral filed. In some embodiments, the "half waveform" treatment can be achieved by limiting rotation or movement of the magnets. In some embodiments, the "half waveform" treatment can be achieved by shielding the north pole or south pole of the magnet, leaving only the other pole exposed for the treatment of the application area.

To subject the treatment area to a dynamic magnetic field by the methods and devices described herein, the magnetic source may be rotated, oscillated, moved through a particular pattern, or otherwise moved relative to the treatment area. In some embodiments, the magnetic source is rotated about an axis. In some embodiments, the magnetic source is oscillated with respect to the application area. In some embodiments, the magnetic source has a linear movement with respect to the application area. Such linear movement can be like a piston movement. In some embodiments, the magnetic source has a swing motion with respect to the application area. Such swing motion can be like a swinging pendulum movement. In some embodiments, the magnetic source has a combination of rotation, linear, oscillated, and swing movements. In some embodiments, the magnetic source has any combination of rotation, linear, oscillated, and swing movements. In some embodiments, said movement comprises at least one of rotational motion, linear motion, and swing motion.

In some oscillatory embodiments, a plurality of magnets are fixedly mounted on a supporting plate, the magnets being spaced apart from each other so that the each magnet is spaced apart from the next nearest magnets by at least one pole width. Each magnet may be positioned so that the upwardly facing pole of each magnet is the same. For example, in one configuration, the north pole face of each magnet is mounted to a supporting plate. In an alternate configuration, the south pole face of each magnet is mounted to a supporting plate. By laterally displacing magnets so arranged proximate to an application area, such area is subjected to a repeating half waveform (full north to zero to full north). In another embodiment, by reversing the polarity of the magnets proximate to the application area, such area is subjected to a repeating half waveform (full south to zero to full south).

In some oscillatory embodiments, a plurality of elongated magnetic sources are placed adjacent to each other so that a repeating pattern of alternating magnetic poles are formed, the poles being spaced apart by a predetermined distance. The oscillation of the magnetic sources by a distance equal to or greater than the predetermined distance subjects an application area to a complete reversal of magnetic flux, i.e., a full waveform.

Figure 11A:
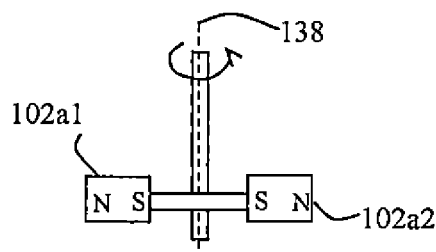
FIGS. 11A through 11K show additional exemplary embodiments for various movements of at least one permanent magnet.
Figure 11B:
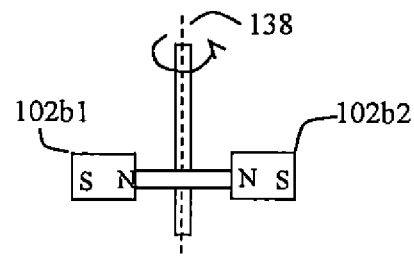
Figure 11C:
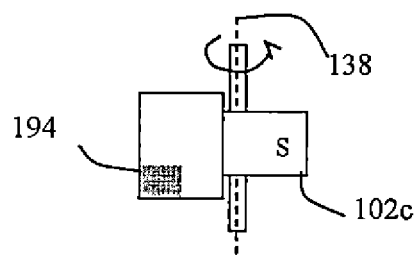

FIGS. 11A through 11K show additional exemplary embodiments for various movements of at least one permanent magnet. FIG. 11A shows two magnets 102*a*1, 102*a*2 coupled to each other and spun about a rotation axis 138*a*. In the embodiment of FIG. 11A, the subject (not shown) could be positioned, for example, such that the rotation axis 138 is generally perpendicular with the scalp of the subject, or wherein the rotation axis 138 is generally parallel to the scalp of the subject, depending on the desired waveform and/or magnetic flux for the particular subject. FIG. 11B is similar to FIG. 11A but with the magnets 102*b*1, 102*b*2 having opposite polarity to the magnets 102*a*1, 102*a*2 of FIG. 11A.

Figure 11D:
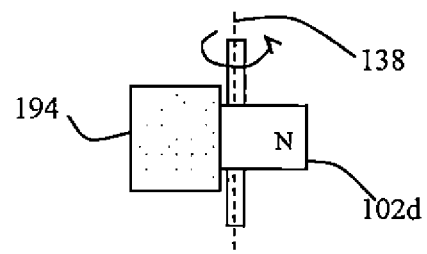

FIG. 11C depicts another embodiment device having a single magnet 102*c* having a shield 194 covering the north pole of the magnet 102*c*. The magnet 102*c* spins about a rotation axis 138 along the neutral plane of the magnet (i.e. between the north and south poles of the magnet 102*c*). In the embodiment of FIG. 11C, the subject (not shown) could be positioned, for example, such that the rotation axis 138 is generally perpendicular with the scalp of the subject, or wherein the rotation axis 138 is generally parallel to the scalp of the subject, depending on the desired waveform and/or magnetic flux for the particular subject. FIG. 11D is similar to FIG. 11C but with the magnet 102*d* having opposite polarity to the magnet 102*c* of FIG. 11C. FIG. 11D shows single magnet 102*d* having a shield 194 covering the south pole of the magnet 102*d*.

Figure 11E:
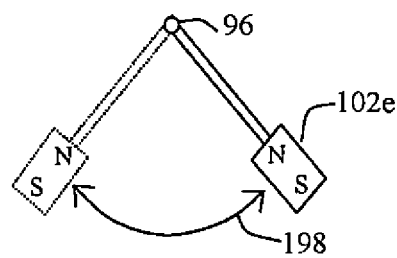
Figure 11F:
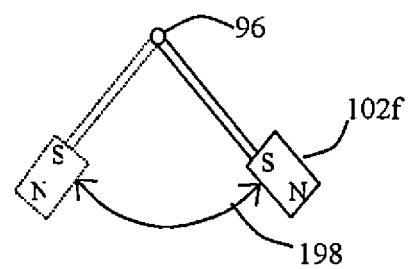

FIG. 11E shows another embodiment device having a single magnet 102*e* that swings with pendulum-like motion along a pendulum path 198, the pendulum path 198 at least in part defined by the distance between magnet 102*e* and the pendulum pivot 96. In the shown embodiment, the south pole (S) of the magnet 102*e* is farther from the pendulum pivot 96 than the north pole (N) of the magnet 102*e*. In the embodiment of FIG. 11E, the subject (not shown) could be positioned, for example, such that the pendulum path 198 is generally perpendicular with the scalp of the subject, or wherein the pendulum path 198 is generally parallel to the scalp of the subject, depending on the desired waveform and/or magnetic flux for the particular subject. FIG. 11F has similar characteristics to FIG. 11E, but with the magnet 102*f* of FIG. 11F having opposite polarity to magnet 102*e* of FIG. 11E.

Figure 11G:
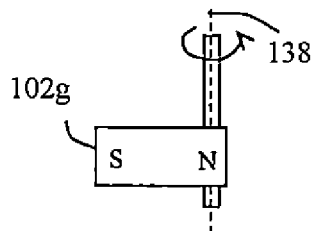
Figure 11H:
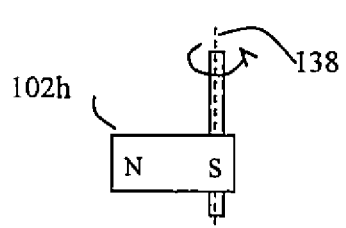

FIG. 11G depicts another embodiment device having a single magnet 102*g* that is configured to spin about a rotation axis 138 positioned in the north pole region of the magnet 102*g* (i.e. somewhere between the neutral plane of the magnet and the north pole (N) end of the magnet 102*g*). The rotation axis 138 is generally parallel to the neutral plane (not shown) of the magnet 102*g*. In the embodiment of FIG. 11G, the subject (not shown) could be positioned, for example, such that the rotation axis 138 is generally perpendicular with the scalp of the subject, or wherein the rotation axis 138 is generally parallel to the scalp of the subject, depending on the desired waveform and/or magnetic flux for the particular subject. FIG. 11H is similar to FIG. 11G but with the magnet 102*h* having opposite polarity to the magnet 102*g* of FIG. 11G, and wherein the rotation axis 138 positioned in the south pole region of the magnet 102*h* (i.e. somewhere between the neutral plane of the magnet and the south pole (S) end of the magnet 102*h*).

Figure 11I:
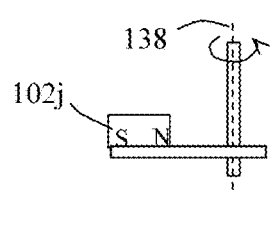
Figure 11J:
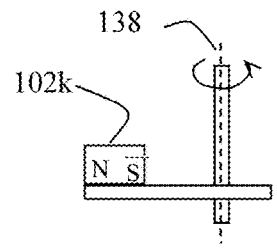

FIG. 11I shows another embodiment device having a single magnet 102*j* mounted a distance away from the rotation axis 138 of the device, and having the north pole (N) of the magnet 102*j* closer to the rotation axis 138 than the south pole (S) of the magnet 102*j*. In the embodiment of FIG. 11I, the subject (not shown) could be positioned, for example, such that the rotation axis 138 is generally perpendicular with the scalp of the subject, or wherein the rotation axis 138 is generally parallel to the scalp of the subject, depending on the desired waveform and/or magnetic flux for the particular subject. FIG. 11J is similar to FIG. 11I but with the magnet 102*k* having opposite polarity to the magnet 102*j* of FIG. 11I.

Figure 11K:
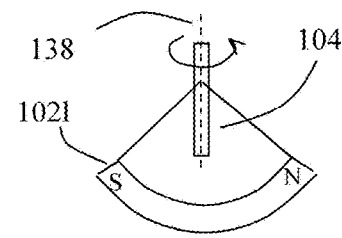

FIG. 11K depicts an alternate embodiment device having a single arc-like magnet 102*l* (which may be, for example, a horseshoe magnet), that is coupled to a drive shaft 104 aligned with the rotation axis 138. As the drive shaft 104 spins about the rotation axis 138, the magnet 102*l* likewise rotates about the rotation axis 138. In the embodiment of FIG. 11K, the subject (not shown) could be positioned, for example, such that the rotation axis 138 is generally perpendicular with the scalp of the subject, or wherein the rotation axis 138 is generally parallel to the scalp of the subject, depending on the desired waveform and/or magnetic flux for the particular subject.

The phrase "continuously applied" or "continuous application" refer to treatments where an application area is subject to at least one magnetic field with a full waveform or a half waveform for a period of time typically longer than 2 minutes. Such phrases are distinguished from short pulse application (typically microseconds) of a magnetic field.

In some embodiments, the devices described can be powered with a rechargeable battery. One battery charge can be enough for one or more therapy sessions. In some embodiments, a display can indicate battery life remaining and signal when the device should be recharged.

In some embodiments, the devices described use at least one connection to a computer to allow for upload of therapy information, download of software upgrades, and to order more sessions to be allowed for the device. The connection may be a USB type of connection, or another type of connection known or contemplated.

The speed of rotation can be critical to the specific therapy that is delivered. Therefore, in some embodiments, the speed of rotation is tightly controlled. In some embodiments, the speed setting may be set by the user or may be set by a controller that uses a biological sensor as feedback to optimize the magnetic field frequency.

In some embodiments, the methods and devices described use at least one bio-feedback sensor, the sensor can be an EEG lead placed on the scalp, along with a reference electrode that can be placed in an area of little sensed brain activity. When more than one EEG sensor is used, correlation information can be gained among separate areas of the brain. The EEG and reference leads can be connected through a differential amplifier to a controller module that regulates the speed of at least one motor to rotate at least one magnet above the scalp.

Sensing EEG with a magnet rotating in the vicinity can be difficult, since the magnet can affect the electrode. To allow proper EEG measurement, a technique may be used to subtract the pure sine wave from the sensed EEG. In some embodiments, the magnet rotation can be stopped temporarily in order to take an EEG measurement that does not include the effect of the rotating magnet.

Figure 27:
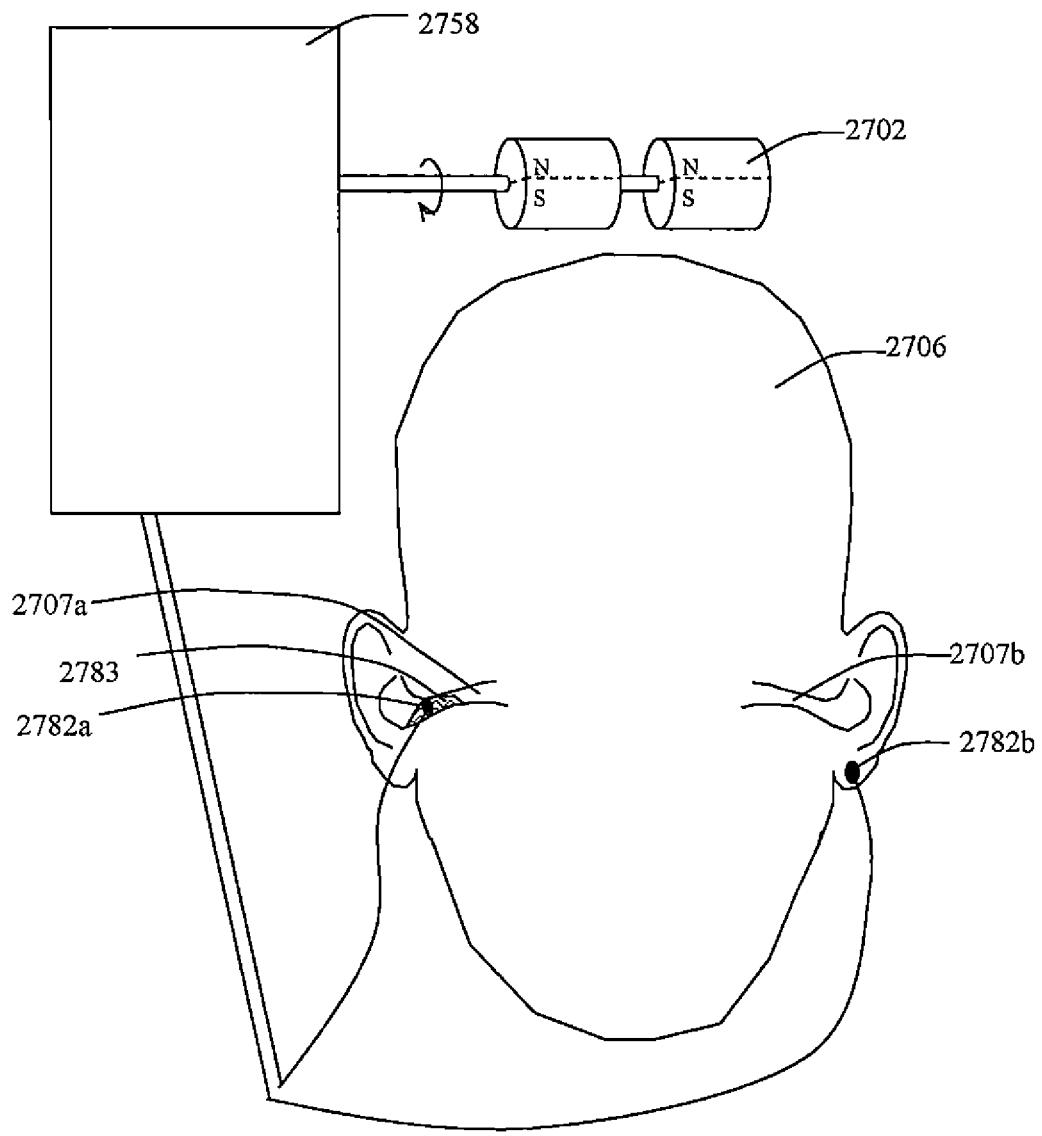
FIG. 27 shows an example embodiment of a NEST device having an EEG electrode located in the subject's ear canal, and a reference EEG electrode located on an earlobe of the subject.
Figure 28:
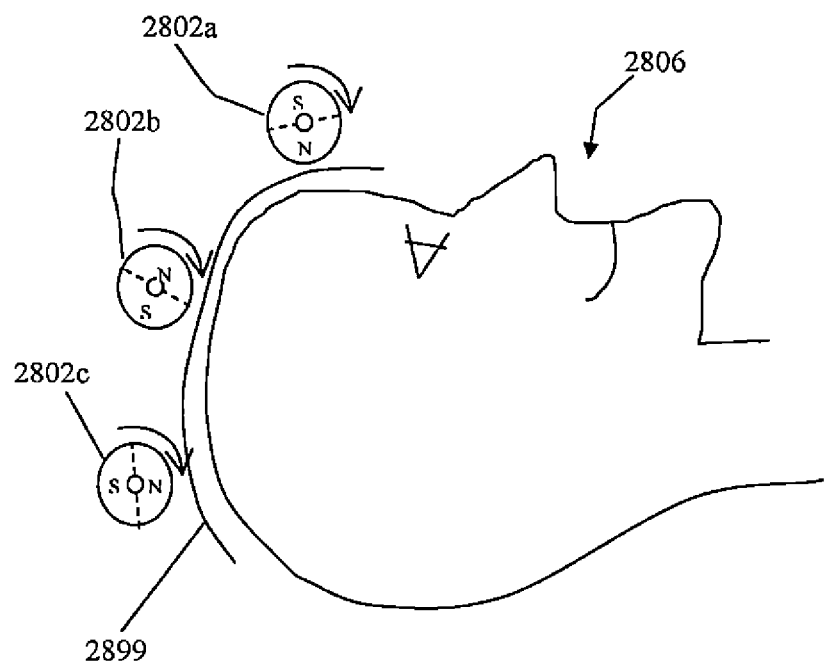
FIG. 28 shows an example embodiment of a NEST device applied to a subject, wherein the NEST device has three diametrically magnetized cylindrical magnets rotating about their cylinder axes having a magnetic phase between at least two of the magnets that is not zero.

Provided herein is a device operable to influence an EEG phase between two sites in the brain of a subject 2806 within a specified EEG band, for example, as shown in FIG. 28. Any of the devices described herein may be used to influence the EEG phase between two sites in the brain of a subject within a specified EEG band. The device may comprise at least two permanent magnets 2802*a*, 2802*b*, wherein the subunit (not shown in FIG. 28, but shown in other figures, for example, FIG. 1-4, 24, 25, 27) of the device is coupled to both the first and the second magnet, and wherein the subunit enables movement of the second magnet at a frequency between about 0.5 Hz and about 100 Hz. The subunit may enable movement of the second magnet at a frequency between about 2 Hz and about 20 Hz. The subunit may enable movement of the first and second magnet at the same frequencies.

FIG. 28 shows an example embodiment of a NEST device applied to a subject 2806, wherein the NEST device has three diametrically magnetized cylindrical magnets 2802*a*, 2802*b*, 2802*c*, rotating about their cylinder axes having a magnetic phase between at least two of the magnets that is not zero. As shown in FIG. 27, a first permanent magnet 2802*a* of a device operable to influence an EEG phase may have a first rotational orientation relative to a treatment surface 2899 of the device and the second permanent magnet 2802*b* may have a second rotational orientation relative to the treatment surface 2899 of the device. The device may be operable to move the first permanent magnet 2802*a* at the same frequency as the second permanent magnet 2802*b*.

Figure 29:
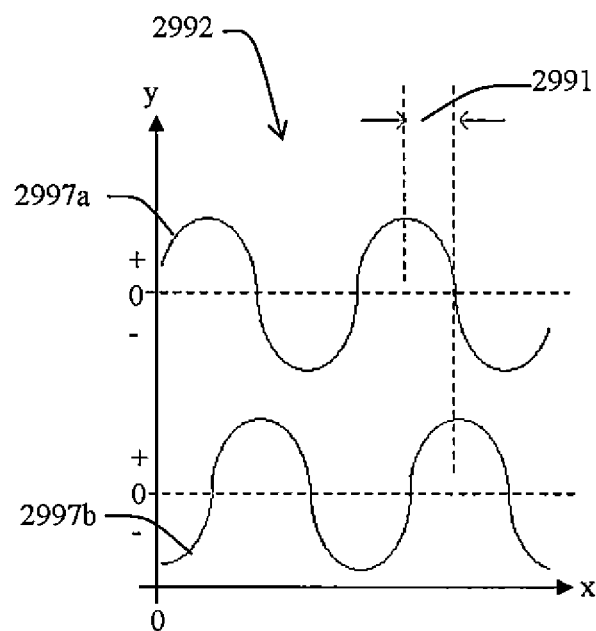
FIG. 29 shows the magnetic field strengths of two magnets moving at the same frequency at the same time, but having a magnetic phase relative to one another (out of phase relative to each other).

In some embodiments, a magnetic field results from a first magnetic source and a second magnetic source. FIG. 29 shows the magnetic field strengths 2997*a*, 2997*b* of two magnets moving at the same frequency at the same time 2992, but having a magnetic phase 2991 relative to one another (out of phase relative to each other). The magnetic field strengths in this graph are plotted with time on the x axis, and magnetic field strength on the y axis (with two x axis, to show the relative field strengths of each magnet simultaneously). As depicted in FIG. 29, a first magnetic source and a second magnetic source may be out of phase relative to each other in order to influence the EEG phase of the subject. In some embodiments, the amount that the first magnetic source and the second magnetic source are out of phase relative to each other is called the magnetic phase 2991. The magnetic phase may be measured peak to peak (i.e. peak of the first magnet's field strength to peak of the second magnet's field strength—as shown in FIG. 29, at 2991), or trough to trough, or inflection to inflection, or any similar plot characteristic on both of the magnets' field strength graphs.

In some embodiments, the first portion of the treatment surface is the portion of the treatment surface approximately closest to the first permanent magnet, and wherein the second portion of the treatment surface is the portion of the treatment surface approximately closest to the second permanent magnet. For example, in FIG. 28, the treatment surface 2899 extends between the magnets 2802*a*, 2802*b*, 2802*c* and the head of the subject 2806. The first portion of the treatment surface is that portion of the treatment surface 2899 between the first magnet 2802*a* and the nearest portion of the head of the subject 2806, Likewise, the second portion of the treatment surface is that portion of the treatment surface 2899 between the second magnet 2802*b* and the nearest portion of the head of the subject 2806. In some embodiments, the first portion of the treatment surface is the portion of the treatment surface closest to the first permanent magnet that is intended to be approximately tangential to the head of the subject nearest that treatment surface. In some embodiments, the second portion of the treatment surface is the portion of the treatment surface approximately closest to the second permanent magnet that is intended to be approximately tangential to the head of the subject nearest that treatment surface.

In some embodiments of the devices disclosed herein, the difference between the first rotational orientation and the second rotational orientation results in a magnetic phase when the first permanent magnet is moved at the same frequency as the second permanent magnet. As shown in FIG. 28, for non-limiting example, the first magnet 2802*a* has a rotational orientation relative to the treatment surface 2899 that is different than the rotational orientation of second magnet 2802*b*. The first magnet 2802*a* has a rotational orientation wherein its neutral axis nearly parallel (or tangential, where the treatment surface is curved) to the treatment surface 2899 nearest it, with its north pole closest to the treatment surface 2899. The second magnet 2802*b* has a rotational orientation wherein its neutral axis that is nearly perpendicular to the treatment surface 2899 nearest it, with its north pole only slightly closer to the treatment surface 2899 than its south pole. Relative to the treatment surface nearest each magnet, thus, the first magnet 2802*a* has a rotational orientation that is offset from the rotational axis of the second magnet 2802*b* by around 90 degrees. The first rotational orientation relative to a first portion of a treatment surface of the device may be between at least about 0 degrees and about 360 degrees different from the second rotational orientation relative to a second portion of the treatment surface of the device. The first rotational orientation relative to a first portion of a treatment surface of the device may be at least one of: between at least about 0 degrees and about 180 degrees, between at least about 0 degrees and about 90 degrees, between at least about 0 degrees and about 45 degrees, between at least about 0 degrees and about 30 degrees, between at least about 0 degrees and about 15 degrees, between at least about 0 degrees and about 10 degrees, at least about 5 degrees, at least about 10 degrees, at least about 15 degrees, at least about 30 degrees, at least about 45 degrees, at least about 60 degrees, at least about 90 degrees, at least about 120 degrees, at least about 180 degrees, at least about 240 degrees, and at least about 270 degrees different from the second rotational orientation relative to a second portion of the treatment surface of the device. The specified EEG frequency may be an intrinsic frequency as described herein. The specified EEG frequency may be a pre-selected frequency as described herein. The pre-selected frequency may be an average intrinsic frequency of a healthy population database within a specified EEG band.

Figure 30:
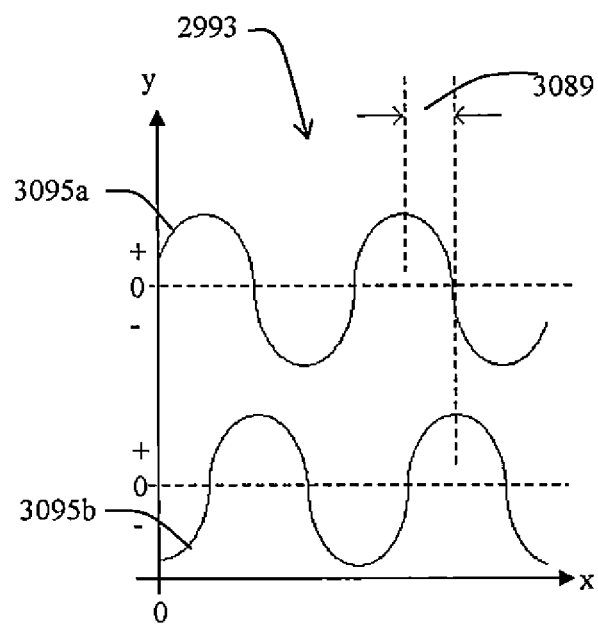
FIG. 30 shows a theoretical EEG electrode readings measured at two locations on a subject's head within a single EEG band when the two locations are exhibiting similar (or the same) frequency, but are out of phase relative to each other, i.e. displaying an EEG phase.

The magnetic phase of the device may be operable to influence an EEG phase between a first site and a second site in the brain of a subject of a specified EEG frequency. FIG. 30 shows theoretical EEG electrode readings 3095a, 3095b measured at two locations on a subject's head within a single EEG band when the two locations are exhibiting similar (or the same) frequency, but are out of phase relative to each other, i.e. displaying an EEG phase 3089. The EEG readings over time in this graph are plotted with time on the x axis, and EEG readings on the y axis (with two x axis, to show two EEG electrode readings taken simultaneously at different locations on the head of the subject). As depicted in FIG. 30, a first EEG reading 3095a, and a second EEG reading 3095b may be out of phase relative to each other. In some embodiments, the amount that the first EEG reading and the second EEG reading are out of phase relative to each other is called the EEG phase 3089. The EEG phase 3089 may be measured peak to peak (i.e. peak of the first EEG reading to peak of the second EEG reading—as shown in FIG. 30, at 3089), or trough to trough, or inflection to inflection, or any similar plot characteristic on both of the EEG reading graphs.

In some embodiments, the first site in the brain of a subject may generally align with a first permanent magnet, and the second site in the brain of a subject may generally align with a second permanent magnet of the device to influence the EEG phase between those two sites. Additional sites also be measured, and additional magnets may additionally be used to influence the EEG phase between given sites toward a pre-selected EEG phase.

Provided herein is a device comprising, a means for applying a first magnetic field to a head of a subject; and a means for applying a second magnetic field to a head of a subject whereby the means for applying the first magnetic field and the means for applying the second magnetic field are capable of influencing an EEG phase between at least two sites in a brain of the subject of a specified EEG frequency. The magnetic fields (first magnetic field, and second magnetic field) may be of the same frequency, but out of phase with each other.

Additional magnetic fields may be provided by additional means for applying such magnetic fields. These too may be out of phase with each other, or with any of the magnetic fields. Nevertheless, the magnetic fields in some embodiments may have the same frequencies. The devices may be a Permanent Magneto-EEG Resonant Therapy (pMERT) (i.e. a Neuro-EEG Synchronization Therapy NEST device) as described herein.

Even a device having a magnetic phase of 0, where the magnets spin at the same frequencies, and in-phase relative to the treatment surface of the device (and/or relative to the head of the subject), may influence the EEG phase between two locations measured on the subject's head. For example, if prior to treatment, two EEG electrodes take EEG readings within an EEG band, and the frequencies are the same (or substantially so), however, the EEG readings have peaks for each electrode at different times (i.e. a non-zero EEG phase), a device as described herein may influence the EEG phase by applying a magnetic field having a magnetic phase (i.e. where the magnets move at the same frequency and in-phase with each other).

In some embodiments, a device comprises a first electrode operable to detect electrical brain activity; and a second electrode operable to detect a reference signal, wherein the first electrode is located on the subject in at least one of: an area of low electrical resistivity on a subject, and an area with substantially no electrical impulse interference on a subject, and wherein the second electrode is located on the subject. In some embodiments, a device comprises a first electrode operable to detect electrical brain activity; and a second electrode operable to detect a reference signal, wherein the first electrode is located on the subject in at least a portion of the ear canal of the subject, and wherein the second electrode is located on the subject. Such electrode placements and configurations may be part of any NEST device described herein. Alternatively, these electrode configurations (including placement and conformation) may be part of any device wherein a clearer EEG signal is desired, since these configurations result in reductions in noise and reduced resistivity from other signals (such as muscle twitches, etc) as compared to electrodes placed on, for example, the head of a subject.

FIG. 27 shows an example embodiment of a NEST device having a first EEG electrode 2782a located in the subject's ear canal 2707, and a reference EEG electrode 2782b (i.e. a second electrode) located on an earlobe of the subject 2706. Conductive gel 2783 may also be used with the first electrode 2782b. In the embodiment shown in FIG. 27, the electrodes 2782a, 2782b, couple by wires to a controller subunit 2758. The controller subunit 2758 also couples to at least one magnet 2702 operable to apply a magnetic field to the subject's 2706 brain by spinning the magnet 2702 about its axis (not shown). Other NEST devices as described herein may be used and may include the EEG electrodes as described. Other magnet, magnets, and/or magnetic field configurations as described herein may be used. Other controller subunits as described herein may be used. The first electrode may be shaped to fit the area having substantially no electrical impulse interference, for non-limiting example, a portion of the ear canal or a portion of the nasal cavity. The electrode may be shaped like a hearing aid, including, for non-limiting example, completely in the canal shaped, canal shaped, half-shell shaped, full shell shaped, behind the ear shaped, and open ear shaped. The first electrode may be conformable to the area having substantially no electrical impulse interference. The first electrode may be compliant such that it fits the specific anatomy of the subject. The first electrode may come in multiple sizes to accommodate a range of subjects' anatomy. The first electrode may be configured such that the subject may place the electrode in the area having substantially no electrical impulse interference without assistance from, for non-limiting example, a second person, a trained EEG technician, or a medical professional.

The area having substantially no electrical impulse interference may be a location having substantially no muscle activity. The area having substantially no muscle activity may naturally have substantially no muscle activity. Alternatively, the area having substantially no muscle activity may be relaxed by a muscle relaxation means such as, for non-limiting example, an injection with a substance that relaxes (and/or paralyzes) the muscles in the area, a topical application of a substance that relaxes (and/or paralyzes) the muscles in the area, and/or by an ingested muscle relaxation substance.

While an anatomical location of substantially no electrical impulse interference (but where brain activity may be measured) may provide a clearer EEG signal resulting in less noise and reduced resistivity from the skull, the first electrode may alternatively be placed on the scalp (either directly, and/or with hair between the scalp and the electrode). A single or a plurality of electrodes may be placed on the scalp for coherence measurement, phase measurement, intrinsic frequency measurement, and/or Q-factor measurement. Noise from scalp movement and/or resistivity from the skull may be filtered from the signal (or signals) received from the EEG electrodes, however, such filtering may not be necessary. Curve smoothing may be applied to the signal (or signals) received from the EEG electrodes, however, such curve smoothing may not be necessary. Using any of the EEG recording means noted herein, multiple signal recordings may be taken and combined to determine, for non-limiting example, a coherence measurement, an intrinsic frequency measurement, and/or a Q-factor measurement. An EEG electrode cap may be used, and signals from one or more electrodes of the cap may be used as described herein to determine an intrinsic frequency, a Q-factor, or coherence.

The area of the scalp upon which the first EEG electrode (or the plurality of electrodes) is/are placed may be induced to have less muscle activity, or it may naturally have less muscle activity than other areas on the scalp. Inducing less muscle activity in the area of the scalp may be achieved in various ways. For non-limiting example, the area may be relaxed by a muscle relaxation means such as an injection with a substance that relaxes (and/or paralyzes) the muscles in the area, a topical application of a substance that relaxes (and/or paralyzes) the muscles in the area, and/or by an ingested muscle relaxation substance.

In some embodiments, the second electrode operable to detect a reference signal is a ground reference. The second electrode may be an ear clip attached to, for non-limiting example, a subject's earlobe. The second electrode may be attached to a location showing substantially no EEG activity. The second electrode may be an ear clip.

The device as described herein may be operable to measure the EEG signal from the subject's brain prior to and/or after the application of the magnetic field to the subject. The device as described herein may comprise logic (in a computer readable format—for non-limiting example, hardware, software) that receives and records the EEG signal prior to and/or following application of the magnetic field to the subject's brain (or a portion thereof). The device as described herein may comprise logic (in a computer readable format) that determines the intrinsic frequency of a specified EEG band of the subject using the EEG signal prior to and/or following application of the magnetic field to the subject's brain (or a portion thereof). The device as described herein may comprise logic (in a computer readable format) that determines the Q-factor of an intrinsic frequency of a specified EEG band of the subject using the EEG signal prior to and/or following application of the magnetic field to the subject's brain (or a portion thereof). The device as described herein may comprise logic (in a computer readable format) that determines the coherence of the intrinsic frequencies of a specified EEG band of the subject measured at multiple brain locations. The device as described herein may comprise logic (in a computer readable format) that determines the phase of the intrinsic frequencies of a specified EEG band of the subject measured at multiple brain locations.

Provided herein is a method of treating a subject, comprising adjusting output of a magnetic field for influencing an intrinsic frequency of a specified EEG band of the subject toward a pre-selected intrinsic frequency of the specified EEG band; and applying said magnetic field close to a head of the subject. In some embodiments, a NEST device, such as one of the NEST devices (pMERT devices) described herein is used to create the magnetic field of the method. In some embodiments, influencing an intrinsic frequency may include influencing harmonics of the pre-selected intrinsic frequency of the specified EEG band. In some embodiments, the pre-selected intrinsic frequency is a harmonic of the peak intrinsic frequency of a specified EEG band. In some embodiments, influencing an intrinsic frequency may include providing a magnetic field having a target frequency that can be represented in the frequency domain by an impulse function. In some embodiments, influencing an intrinsic frequency may include providing a magnetic field having a target frequency having no variation (standard of deviation around the target frequency is 0). In some embodiments, influencing an intrinsic frequency may include providing a magnetic field having a target frequency plus or minus at most 1% of the target frequency. In some embodiments, influencing an intrinsic frequency may include providing a magnetic field having a target frequency plus or minus at most 5% of the target frequency. In some embodiments, influencing an intrinsic frequency may include providing a magnetic field having a target frequency plus or minus at most 10% of the target frequency. In some embodiments, influencing an intrinsic frequency may include providing a magnetic field having a target frequency plus or minus at most 10% of the target frequency. In some embodiments, influencing an intrinsic frequency may include providing a magnetic field having a target frequency plus or minus at most 15% of the target frequency. In some embodiments, influencing an intrinsic frequency may include providing a magnetic field having a target frequency plus or minus at most 20% of the target frequency.

Provided herein is a method of treating a subject, comprising adjusting output of a magnetic field for influencing a Q-factor a measure of frequency selectivity of a specified EEG band of the subject toward a pre-selected Q-factor of the band; and applying said magnetic field close to a head of the subject. In some embodiments, a NEST device, such as one of the NEST devices (pMERT devices) described herein is used to create the magnetic field of the method.

Provided herein is a method of treating a subject, comprising adjusting output of a magnetic field for influencing a coherence of intrinsic frequencies among multiple sites in a brain of the subject within a specified EEG band toward a pre-selected coherence value; and applying said magnetic field close to a head of the subject. In some embodiments, a NEST device, such as one of the NEST devices (pMERT devices) described herein is used to create the magnetic field of the method.

Provided herein is a method of altering an intrinsic frequency of a brain of a subject within a specified EEG band, comprising determining the intrinsic frequency of the subject within the specified EEG band; comparing the intrinsic frequency from step (a) to an average intrinsic frequency of a healthy population database; if the intrinsic frequency from step (a) is higher than the average intrinsic frequency of the healthy population database, shifting down the intrinsic frequency of the subject by applying a specific magnetic field close to a head of the subject, wherein said specific magnetic field has a frequency lower than the intrinsic frequency of the subject; and if the intrinsic frequency from step (a) is lower than the average intrinsic frequency of the healthy population database, shifting up the intrinsic frequency of the subject by applying a specific magnetic field close to a head of the subject, wherein said specific magnetic field has a frequency higher than the intrinsic frequency of the subject. In some embodiments, a NEST device, such as one of the NEST devices (pMERT devices) described herein is used to create the magnetic field of the method.

Provided herein is a method of altering a Q-factor of an intrinsic frequency within a specified EEG band of a subject, comprising determining the Q-factor of the intrinsic frequency within the specified EEG band of the subject;

comparing the Q-factor of the intrinsic frequency from step (a) to an average Q-factor of the intrinsic frequency of a healthy population database; if the Q-factor of the intrinsic frequency from step (a) is higher than the average Q-factor of the intrinsic frequency of the healthy population database, tuning down the Q-factor of the intrinsic frequency of the subject by applying a magnetic field with varying frequencies close to a head of the subject; and if the Q-factor of the intrinsic frequency from step (a) is lower than the average Q-factor of the intrinsic frequency of the healthy population database, tuning up the Q-factor of the intrinsic frequency of the subject by applying a specific magnetic field with a pre-selected frequency close to a head of the subject. In some embodiments, a NEST device, such as one of the NEST devices (pMERT devices) described herein is used to create the magnetic field of the method.

Provided herein is a method of improving coherence of intrinsic frequencies within a specified EEG band among multiple locations of a brain of a subject, comprising determining the coherence value of the intrinsic frequencies among multiple locations throughout a scalp of the subject; comparing the coherence value from step (a) to an average coherence value of a healthy population database; if the coherence value from step (a) is higher than the average coherence value of the healthy population database, lowering the coherence value of the subject by applying at least two asynchronous magnetic fields close to a head of the subject; if the coherence value from step (a) is lower than the average coherence value of the healthy population database, raising the coherence value of the subject by applying at least one synchronized magnetic field close to a head of the subject. In some embodiments, a NEST device, such as one of the NEST devices (pMERT devices) described herein is used to create the magnetic field of the method.

Provided herein is a method comprising adjusting an output current of an electric alternating current source for influencing a Q-factor of an intrinsic frequency of an EEG band of a subject toward a target Q-factor; and applying said output current across a head of the subject.

Provided herein is a method comprising adjusting output of a magnetic field for influencing an EEG phase between two sites in the brain of a subject of a specified EEG frequency toward a pre-selected EEG phase of the specified EEG frequency; and applying said magnetic field close to a head of the subject.

In some embodiments, the pre-selected EEG phase is lower than the EEG phase between the two sites in the brain of the subject. In some embodiments, the pre-selected EEG phase is any EEG phase lower than the EEG phase between the two sites in the brain of the subject. In some embodiments, the pre-selected EEG phase is higher than the EEG phase between the two sites in the brain of the subject. In some embodiments, the pre-selected EEG phase is any EEG phase higher than the EEG phase between the two sites in the brain of the subject. In some embodiments, the pre-selected EEG phase is an EEG phase of a population of people. The population of people may be a set of people having a particular trait, characteristic, ability, or feature. The population may be a healthy population of people. The population of people may be a set of people not having a particular disorder, such as anxiety, depression, or other disorders mentioned herein. In some embodiments, the methods comprise measuring EEG data of two sites in the brain of the subject, and calculating the EEG phase between the two sites in the brain of a subject.

In some embodiments, there is no pre-selected EEG phase. Rather, the method comprises adjusting output of a magnetic field for influencing an EEG phase between two sites in the brain of a subject within a specified EEG band; and applying said magnetic field close to a head of the subject. The EEG phase may be influenced to be lower, or higher.

In another aspect are methods for influencing an EEG phase of a specified EEG frequency between multiple locations of a brain of a subject, comprising determining the EEG phase the between at least two locations measured on the head of the subject; comparing the EEG phase to an average EEG phase of a healthy population; and applying a magnetic field close to a head of the subject. Applying the magnetic field may influences the determined EEG phase toward the average EEG phase of a healthy population. The specified EEG frequency may be an intrinsic frequency as described herein. The specified EEG frequency may be a pre-selected frequency as described herein. The pre-selected frequency may be an average intrinsic frequency of a healthy population database within a specified EEG band.

In another aspect are methods for using a Transcranial Magnetic Stimulation (TMS) device for influencing an EEG phase of a subject within a specified EEG band, comprising: adjusting output of said TMS device; changing the EEG phase by repetitive firing of at least one magnetic field using said TMS device; and applying said magnetic field close to a head of the subject.

In some embodiments, the magnetic field results from a first magnetic source and a second magnetic source. In some embodiments, the first magnetic source and the second magnetic source are out of phase relative to each other. In some embodiments, the amount that the first magnetic source and the second magnetic source are out of phase relative to each other is called the magnetic phase.

In some embodiments of at least one aspect described herein, the step of applying the magnetic field is for a pre-determined cumulative treatment time. In some embodiments of at least one aspect described above, the pre-selected or target intrinsic frequency with the specified EEG band is from about 0.5 Hz to about 100 Hz. In some embodiments of at least one aspect described above, the pre-selected or target intrinsic frequency with the specified EEG band is from about 1 Hz to about 100 Hz. In some embodiments of at least one aspect described above, the pre-selected or target intrinsic frequency with the specified EEG band is not greater than about 50 Hz. In some embodiments of at least one aspect described above, the pre-selected or target intrinsic frequency with the specified EEG band is not greater than about 30 Hz. In some embodiments of at least one aspect described above, the pre-selected or target intrinsic frequency with the specified EEG band is not greater than about 20 Hz. In some embodiments of at least one aspect described above, the pre-selected or target intrinsic frequency with the specified EEG band is not greater than about 10 Hz. In some embodiments of at least one aspect described above, the pre-selected or target intrinsic frequency with the specified EEG band is greater than about 3 Hz. In some embodiments of at least one aspect described above, the pre-selected or target intrinsic frequency with the specified EEG band is greater than about 1 Hz.

In some embodiments, of at least one aspect described above, the pre-selected or target intrinsic frequency with the specified EEG band is up to about 25 Hz. As used herein, the term "about" when referring to a frequency can mean variations of 0.1 Hz-0.2 Hz, 0.1 Hz to 0.5 Hz, 0.5 Hz to 1 Hz, or 1 Hz to 5 Hz.

In some embodiments, the pre-selected and/or target intrinsic frequency is chosen from a plurality of intrinsic frequencies in the specified EEG band. In some embodiments the pre-selected and/or target intrinsic frequency is chosen from a plurality of intrinsic frequencies across a plurality of EEG bands. In some embodiments the specified EEG band is the Alpha band. In some embodiments the specified EEG band is the Beta band.

In some embodiments of the methods described herein, the method or methods may comprise locating a first electrode operable to detect electrical brain activity on the subject in an area of low electrical resistivity on a subject. In some embodiments of the methods described herein, the method or methods may comprise locating a first electrode operable to detect electrical brain activity on the subject in an area with substantially no electrical impulse interference on a subject. In some embodiments of the methods described herein, the method or methods may comprise locating a first electrode operable to detect electrical brain activity on the subject in an area having substantially no electrical impulse interference. In some embodiments of the methods described herein, the method or methods may comprise locating a first electrode operable to detect electrical brain activity on the subject in a location having substantially no muscle activity. The method or methods may further comprise locating a second electrode operable to detect a reference signal on the subject. The method or methods may further comprise determining the intrinsic frequency from: the electrical brain activity detected by the first electrode, and the reference signal detected by the second electrode.

In some embodiments of the methods described herein, the method or methods may comprise locating a first electrode operable to detect electrical brain activity on the subject in at least a portion of the ear canal of the subject. The method or methods may further comprise locating a second electrode operable to detect a reference signal on the subject. The method or methods may further comprise determining the intrinsic frequency from the electrical brain activity detected by the first electrode and the reference signal detected by the second electrode.

The method or methods described herein may comprise applying conductive gel to the area of low electrical resistivity on a subject (i.e. the location at which the first electrode is placed). The method or methods described herein may comprise applying conductive gel to the area having substantially no electrical impulse interference on a subject (i.e. the location at which the first electrode is placed). The method or methods described herein may comprise applying conductive gel to the area having substantially no muscle activity (i.e. the location at which the first electrode is placed). Alternatively, or in addition to the applying the gel, the method may comprise shaping the first electrode to fit the area at which the first electrode is placed, for non-limiting example, the portion of the ear canal or the portion of the nasal cavity in which the first electrode is placed. The electrode may be pre-shaped to generally fit the intended anatomical location of electrode placement, or the electrode may be shaped in-situ to fit the specific subject's anatomical location of electrode placement. The method may comprise shaping the electrode to fit an anatomical location (for example, the area at which the first electrode is to be placed). The method may comprise providing an electrode that fits an anatomical location (for example, the area at which the first electrode is to be placed). The first electrode may come in multiple sizes to accommodate a range of subjects' anatomy. The first electrode may be configured such that the subject may place the electrode in the area having substantially no electrical impulse interference without assistance from, for non-limiting example, a second person, a trained EEG technician, or a medical professional.

The method or methods described herein may comprise placing the first electrode in a location having substantially no electrical impulse interference may be a location having substantially no muscle activity. The area having substantially no muscle activity may naturally have substantially no muscle activity. The method or methods described herein may comprise relaxing the area of the subject at which the first electrode is placed by a muscle relaxation means such as by, for non-limiting example, injecting with a substance that relaxes the muscles in the area, applying a topical substance that relaxes the muscles in the area, and/or by providing an ingestible muscle relaxation substance to the subject that relaxes the muscles in the area. The method or methods described herein may comprise paralyzing the area of the subject at which the first electrode is placed by a muscle paralysis means such as by, for non-limiting example, and/or injecting with a substance that substantially paralyzes the muscles in the area, applying a topical substance that substantially paralyzes the muscles in the area.

While an anatomical location of substantially no electrical impulse interference, and/or a location having substantially no muscle activity (but where brain activity may be measured) may provide a clearer EEG signal resulting in less noise and reduced resistivity from the skull, nevertheless, the methods provided herein may comprise placing the first electrode on the scalp (either directly, and/or with hair between the scalp and the electrode). The methods provided herein may comprise placing a plurality of electrodes on the scalp for coherence measurement, intrinsic frequency measurement, and/or Q-factor measurement. The methods provided herein may comprise filtering from the signal (or signals) received from the EEG electrodes noise from scalp movement and/or resistivity from the skull. The methods provided herein may comprise smoothing the signal curve received and/or determined from the EEG electrodes. The methods provided herein may comprise determining from multiple signal recordings: a coherence measurement, an intrinsic frequency measurement, and/or a Q-factor measurement using any of the EEG recording means noted herein. An EEG electrode cap may be used, and signals from one or more electrodes of the cap may be used as described herein to determine an intrinsic frequency, a Q-factor, or coherence.

The area of the scalp upon which the first EEG electrode (or the plurality of electrodes) is/are placed may be induced to have less muscle activity, or it may naturally have less muscle activity than other areas on the scalp. Inducing less muscle activity in the area of the scalp may be achieved in various ways. For non-limiting example, the methods may comprise relaxing the area where the first electrode is placed, for non-limiting example, by injecting the area with a substance that relaxes (and/or paralyzes) the muscles in the area, applying a topical substance that relaxes (and/or paralyzes) the muscles in the area, and/or by providing an ingestible muscle relaxation substance that relaxes the muscles in the area.

In some embodiments, the method comprises placing a second electrode operable to detect a reference signal, wherein the second electrode is a ground reference. The method may comprise attaching an ear clip electrode to, for non-limiting example, a subject's earlobe. The ear clip may be removable. The method may comprise attaching the second electrode to a location showing substantially no EEG activity.

Measuring the EEG signal from the subject's brain (i.e. measuring EEG data of the subject) may be done prior to and/or after the application of the magnetic field to the subject. The method may comprise receiving the EEG signals (i.e. receiving the reference signal from the reference electrode and receiving the brain activity from the first electrode) prior to application of the magnetic field to the subject's brain (or a portion thereof). The method may comprise recording the EEG signals prior to application of the magnetic field to the subject's brain (or a portion thereof). The EEG signals (i.e. receiving the reference signal from the reference electrode and receiving the brain activity from the first electrode) received and/or recorded prior to application of the magnetic field to the subject's brain (or a portion thereof) may be used in determining at least one of the intrinsic frequency of a specified EEG band of the subject, the Q-factor of an intrinsic frequency of a specified EEG band of the subject, the phase of the intrinsic frequencies of a specified EEG band of the subject, and the coherence of the intrinsic frequencies of a specified EEG band of the subject measured at multiple brain locations. The method may comprise receiving the EEG signals (i.e. receiving the reference signal from the reference electrode and receiving the brain activity from the first electrode) following (or after) application of the magnetic field to the subject's brain (or a portion thereof). The method may comprise recording the EEG signals (i.e. the reference signal from the reference electrode and the brain activity from the first electrode) following or after application of the magnetic field to the subject's brain (or a portion thereof). The EEG signals received and/or recorded (i.e. the reference signal from the reference electrode and the brain activity from the first electrode) following (or after) application of the magnetic field to the subject's brain (or a portion thereof) may be used in determining at least one of the post-treatment intrinsic frequency of a specified EEG band of the subject, the post-treatment Q-factor of an intrinsic frequency of a specified EEG band of the subject, the post-treatment phase of the intrinsic frequencies of a specified EEG band of the subject, and the post-treatment coherence of the intrinsic frequencies of a specified EEG band of the subject measured at multiple brain locations. Determining the intrinsic frequency may comprise removing the reference signal detected by the second electrode from the electrical brain activity detected by the first electrode. Determining the Q-factor of an intrinsic frequency of the specified EEG band comprises ascertaining the Q-factor from the electrical brain activity detected by the first electrode and the reference signal detected by the second electrode by removing the reference signal detected by the second electrode from the electrical brain activity detected by the first electrode and calculating the Q-factor from the intrinsic frequency fo and the Δf as shown in FIG. 12.

rTMS Therapy

Repetitive Transcranial Magnetic Stimulation (rTMS) refers to uses of a magnetic field administered in very short grouped pulses (microseconds in length) to a patient's head to achieve a constant train of activation over brief periods of a treatment session. These brief magnetic fields can stimulate small areas of the brain non-invasively. During a single session, about 3,000 magnetic pulses can be given over an interval of about 30 minutes.

The short pulses of magnetic energy generated by rTMS devices can stimulate nerve cells of the brain, often at frequencies close to thresholds of exciting brain cells. Magnetic fields generated by rTMS devices can pass through the skull and into the cortex without being distorted. The result is a very focal type of stimulation, minimizing stimulation of brain tissue not intended to be stimulated.

The magnetic pulses generated by rTMS devices are generally believed to induce electrical charges to flow. The amount of electricity created in the brain is very small, and can not be felt by the patient. These flowing electric charges can cause the neurons to fire or become active under certain circumstances. Typically, an objective of rTMS Therapy is to stimulate (or activate) brain cells.

Jin Y et al. Therapeutic effects of individualized alpha frequency transcranial magnetic stimulation (alphaTMS) on the negative symptoms of schizophrenia. Schizophr Bull. 32(3):556-61 (2006 July; Epub 2005 Oct. 27), which is incorporated by reference in its entirety, described four stimulation parameters that require optimization for rTMS:
(a) Frequency—Higher frequencies (>10 Hz) are believed to increase cortical excitability;
(b) Intensity—As a percentage of the threshold at which motor activity can be elicited (~1-2 Tesla);
(c) Duration—Pulse trains are brief (1-2 seconds), and intertrain intervals can be 30-60 seconds; and
(d) Site of Stimulation—Depending on patient population or specific brain functions.

In some embodiments, severity of psychosis, depression, and movement disorders can be assessed with PANSS, Montgomery-Asberg Depression Rating Scale (MADRS), Barnes Akathisia Rating Scale (BARS), and Simpson-Angus Scale (SAS), as described by Jin Y et al. above. In some embodiments, severity of psychosis, depression, and movement disorders can be assessed with the Hamilton Anxiety Scale (HAMA), the Hamilton Depression Scale (HAMD), or any methods known in the art. In some embodiments, efficacy in clinical ratings can be evaluated by using analyses of variance (ANOVA) as described by Jin Y et al. above. In some embodiments, raw EEG data can be edited offline by an experienced technician who is blind to the treatment conditions to eliminate any significant or apparent artifact as described in Jin Y et al. above. In some embodiments, multivariate analysis of variance (MANOVA) with repeated measures can be used to determine the main effect interactions as described in Jin Y et al. above.

Since EEG changes can be direct consequences of treatments using the methods or devices described herein, those EEG changes can be used to clinically correlate improvement in symptoms of mental disorders. Improvement in symptoms can include positive symptoms and negative symptoms. In some embodiments, the EEG changes after using the methods or devices described correlated to both positive symptoms and negative symptoms. In some embodiments, the EEG changes after using the methods or devices described correlated to only positive symptoms. In some embodiments, the EEG changes after using the methods or devices described correlated to only negative symptoms. In some embodiments, correlations between EEG changes and improvement in negative symptoms are only significant in the absence of positive symptoms. In some embodiments, correlations between EEG changes and improvement in positive symptoms are only significant in the absence of negative symptoms.

In some embodiments, negative symptoms include, but not limited to, loss of motivation, anhedonia, emotional flattening, and psychomotor retardation. These negative symptoms can be associated with patient's cognitive deficits and poorer clinical prognosis, and often resistant to antipsychotic medications. See Gasquet et al., Pharmacological treatment and other predictors of treatment outcomes in previously untreated patients with schizophrenia: results from the European Schizophrenia Outpatient Health Outcomes (SOHO) study. *Int Clin Psychopharmacol.* 20: 199-205 (2005), which is incorporated by reference in its entirety.

CES Therapy

Cranial Electrotherapy Stimulation (CES) is a method of applying microcurrent levels of electrical stimulation across the head via transcutaneous electrodes. Provided herein is method including applying an electric alternating current (AC) across a head of a subject, and adjusting and/or varying the frequency of the AC current to effect at least one of a characteristic, mental disorder, and an indication presented herein. In some embodiments, the AC current is a microcurrent.

Provided herein is a method comprising adjusting an output of an electric alternating current source for influencing an intrinsic frequency of a EEG band of a subject toward a target frequency of the EEG band; and applying said electric alternating current across a head of the subject. In some embodiments of the methods, a CES therapy is used to influence the intrinsic frequency of a patient's brain toward a target frequency as measured by EEG.

Provided herein is a method comprising adjusting an output current of an electric alternating current source for influencing an intrinsic frequency of an EEG band of a subject toward a target frequency of the EEG band; and applying said output current across a head of the subject. In some embodiments, the step of adjusting the output current comprises setting the output current to a frequency that is lower than the intrinsic frequency of the subject. In some embodiments, the step of adjusting the output current comprises setting the output current to a frequency that is higher than the intrinsic frequency of the subject. In some embodiments, the step of adjusting the output current comprises setting the output current to the target frequency. In some embodiments, the method further comprises determining the intrinsic frequency of the EEG band of the subject; and comparing the intrinsic frequency to the target frequency of the EEG band, wherein the target frequency is an average intrinsic frequency of the EEG bands of a healthy population of people, wherein if the intrinsic frequency is higher than the target frequency, the step of adjusting the output current comprises setting the output current to a frequency that is lower than the intrinsic frequency of the subject, and if the intrinsic frequency is lower than the target frequency, the step of adjusting the output current comprises setting the output current to a frequency that is higher than the intrinsic frequency of the subject.

Provided herein is a method comprising adjusting an output of an electric alternating current source for influencing a Q-factor a measure of frequency selectivity of a specified EEG band of a subject toward a target Q-factor of the band; and applying said electric alternating current across a head of the subject. In some embodiments of the methods, a controlled waveform CES therapy is used to influence a Q-factor of an intrinsic frequency of a patient's brain. FIG. 12 shows an example of the Q-factor as used in this invention. The figure shows a sample graph of the frequency distribution of the energy of an EEG signal. It can be seen that a frequency range, $\Delta f$ can be defined as the frequency bandwidth for which the energy is above one-half the peak energy. The frequency $f_0$ is defined as the intrinsic frequency in the specified band. The Q-factor is defined as the ratio of $f_0/\Delta f$. As can be seen, when $\Delta F$ decreases for a given $f_0$, the Q-factor will increase. This can occur when the peak energy $E_{max}$ of the signal increases or when the bandwidth of the EEG signal decreases.

Provided herein is a method comprising adjusting an output current of an electric alternating current source for influencing a Q-factor of an intrinsic frequency of an EEG band of a subject toward a target Q-factor; and applying said output current across a head of the subject. In some embodiments, the step of adjusting the output current comprises varying a frequency of the output current. In some embodiments, the step of adjusting the output current comprises setting the output current to a frequency that is higher than the intrinsic frequency of the subject. In some embodiments, the step of adjusting the output current comprises setting the output current to a frequency that is lower than the intrinsic frequency of the subject. In some embodiments, the step of adjusting the output current comprises setting the output current to the target frequency. In some embodiments, the method further comprises determining the Q-factor of the intrinsic frequency of the EEG band of the subject; and comparing the Q-factor to the target Q-factor, wherein the target Q-factor is an average Q-factor of the intrinsic frequencies of the EEG bands of a healthy population of people, wherein if the intrinsic frequency is higher than the target frequency, the step of adjusting the output current comprises varying a frequency of the output current, and if the intrinsic frequency is lower than the target frequency, the step of adjusting the output current comprises setting the output current to a frequency that is higher than the intrinsic frequency of the subject.

In some embodiments, the frequency of the output current has a waveform. In some embodiments, the waveform is a sinusoidal or near-sinusoidal AC microcurrent waveform (i.e. a controlled waveform). In some embodiments, the waveform is any waveform described herein, including but not limited to a half waveform and/or a full waveform. In some embodiments, the EEG band is the alpha band measured by EEG. In some embodiments, the intrinsic frequency is the alpha frequency of the patient's brain measured by EEG. In some embodiments, the target frequency is a target frequency of the alpha band as measure by EEG. In some embodiments the target frequency is an average frequency of a group of at least two people of the specified EEG band. In some embodiments, the healthy population of people comprises at least two healthy people. In some embodiments, the healthy population of people comprises at least two people, each of whom do not have at least one of the mental disorders listed above. In some embodiments, the healthy population of people comprises at least two people without any of the mental disorders listed above.

It will be understood by those of skill in the art that numerous and various modifications can be made without departing from the spirit of the present invention. Therefore, it should be clearly understood that the forms of the present invention are illustrative only and are not intended to limit the scope of the present invention.

EXAMPLES

The invention is described in greater detail by the following non-limiting examples.

Example 1

In some embodiments, described are devices that provide low frequency near-sinusoidal TMS therapy by rotating at least one permanent magnet in close proximity to the subject's head. The direction of rotation relative to the subject can vary depending on the specific therapy desired. Also, the speed of rotation can be adjusted to provide the optimal therapeutic benefit. The speed adjustment itself can come from the user of the device or from a controller that uses feedback from a bio-sensor to determine the optimal speed.

In particular embodiments, a bar magnet can be mounted at the end of the shaft with the line through the poles perpendicular to the axis of the shaft. The shaft can be rotated by an adjustable motor. The magnet can rotate so that the plane of rotation is perpendicular to the surface of the scalp. Accordingly, the positive and negative poles of the magnet can be alternately brought in close proximity to the scalp. This can create a near-sinusoidal magnetic field in the brain in which the location where the field is strongest is that which is closest to the magnet.

Example 2

In particular embodiments, a horseshoe magnet can be mounted at the end of the shaft with the poles positioned at the far end from the shaft. The shaft can be rotated by an adjustable motor, as in the previous example. The magnet can be positioned above the subject's scalp such that the plane of rotation is parallel to the surface of the scalp. Accordingly, the positive and negative poles can rotate in a circle around the scalp. This can create a sinusoidal magnetic field in the brain in which the phase of the magnetic field is dependent on where the magnetic poles are in their rotation. In general, the magnetic field under one pole will be of opposite polarity to the magnetic field under the opposite pole.

Example 3

In particular embodiments, two bar magnets can be used, each mounted at the end of a shaft. The shafts can be rotated by adjustable motors. The magnets can be positioned on opposite sides of the subject's head, and they are rotated synchronously to provide a more uniform phase for the magnetic field in the brain. When the north Pole of one bar magnet is next to the subject's scalp, the south Pole of the other magnet will be next to the subject's scalp on the opposite side of the subject's head.

Example 4

Figure 7:
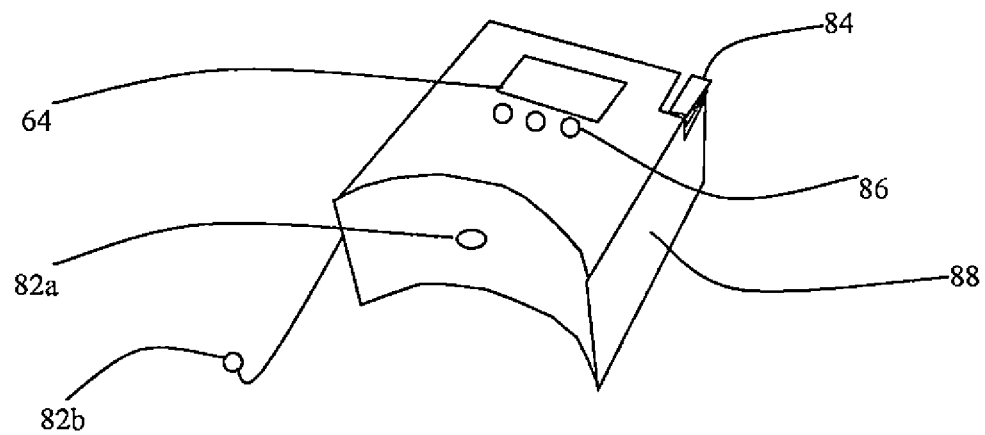
FIG. 7 shows an exemplary embodiment of the pMERT or NEST device. In this embodiment, a button EEG electrode is located on the concave surface of the device and a second reference electrode extends via a wire from the side of the device. The display and control buttons are located on top of the device to provide information and allow the user to adjust parameters and enter patient data. A USB port is located at the top rear of the device, to allow it to be connected via a USB cable to a PC, allowing uploading of data and downloading of a dosage quota.
Figure 8:
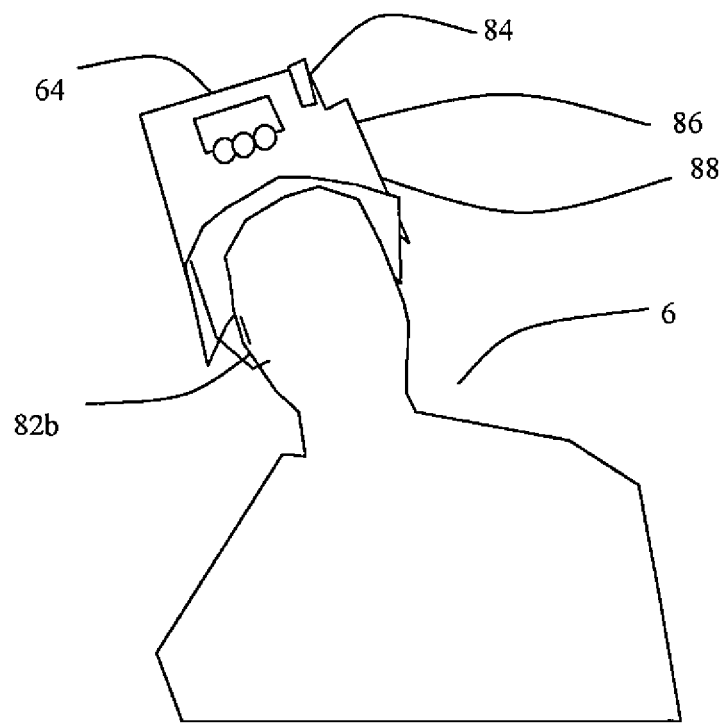
FIG. 8 shows the pMERT or NEST device from FIG. 7 in which a subject is lying with the head against the concave surface. At least one moving magnet is unseen inside the pMERT or NEST device in order to deliver therapy to the subject. The subject's head is pressed against the button EEG electrode, with the second electrode attached to the subject's right ear.
Figure 9:
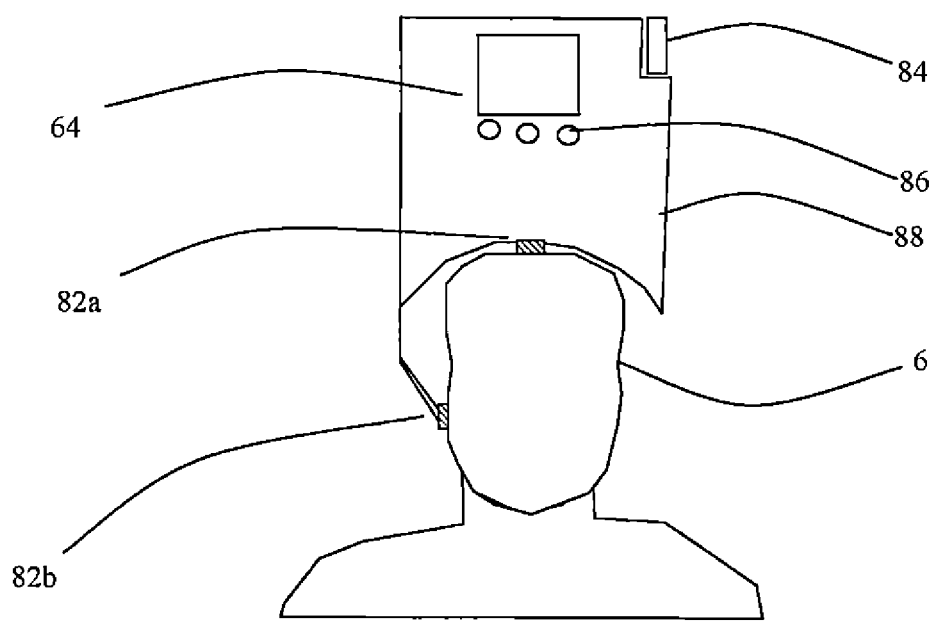
FIG. 9 shows an alternate angle of the subject receiving therapy from the pMERT or NEST device as described in FIG. 8.

In particular embodiments, the NEST (pMERT) device is a small, generally cube-shaped device with one side that is curved to allow contact with the top of the subject's head. FIGS. 7-9 show the NEST (pMERT) device in such embodiments, and also show the NEST (pMERT) device with a subject lying on his/her back with his/her head resting in the device to receive therapy.

FIGS. 7, 8, and 9 show an exemplary embodiment of the pMERT (NEST) device 88. In this embodiment, a button EEG electrode 82a is located on the concave surface of the device 88 and a second reference electrode 82b extends via a wire from the side of the device 88. The display 64 and control buttons 86 (device controls) are located on top of the device 88 to provide information and allow the user to adjust parameters and enter patient data. A USB port 84 (which may also and/or alternatively be at least one of an internet connection port, a power supply, a modem connection, and another type of communications means) is located at the top rear of the device 88, to allow it to be connected via a USB cable to a PC, allowing uploading of data and downloading of a dosage quota. FIG. 8 shows the pMERT (NEST) device 88 from FIG. 7 in which a subject 6 is lying with his/her head against the concave surface of the device 88. At least one moving magnet is unseen inside the pMERT (NEST) device 88 in order to deliver therapy to the subject 6. Moving magnets such as those in configurations described herein may be used in the device 88 shown in FIGS. 7, 8, and 9. The subject's head is pressed against the button EEG electrode (not shown), with the second electrode 82b attached to the subject's right ear. FIG. 9 shows an alternate angle of the subject 6 receiving therapy from the pMERT (NEST) device 88 as described in FIG. 7 and/or FIG. 8.

In these particular embodiments, the pMERT as shown in FIGS. 7-9 contains a single EEG lead (i.e. electrode) which is to be placed at the top of the subject's head. Alternatively, multiple EEG electrodes may be used in recording and/or monitoring the subject's brain waves at least one of before, during, and after the therapy is applied to the subject. The subject or nurse can prepare the EEG leads (and/or electrodes) with an electrolytic gel beforehand to lower the impedance. The reference electrode can be placed on the subject's ear. In some embodiments, the reading from a reference EEG electrode is subtracted and/or otherwise removed from the reading from the second EEG electrode.

When therapy is needed, the subject or nurse can follow the instructions on the display, which will provide a walk-through of the EEG electrode preparation. Once complete and the patient is situated in the device, the EEG is checked by the pMERT to ensure that the electrode is placed correctly. If not, an audible tone or instruction is given to allow the patient to resituate himself/herself until proper contact is made.

Once contact is made, the patient lies still with eyes closed while the pMERT (NEST) acquires a representative EEG sample. The EEG data is analyzed and, depending on the therapy to be delivered, the magnet or magnets are rotated at the appropriate speed. The patient does not feel anything during the procedure, except for a diminution of the symptoms of the disorder, and perhaps a feeling of calm. During therapy, the device may sample the EEG data either by subtracting out the influence of the magnet or by temporarily halting the magnet while the EEG data is sampled. The display is used to show time remaining and any other necessary status information for the device. After the therapy time, the magnet stops and a second EEG is taken, to be compared to the first EEG. Upon completion of the second EEG acquisition, an audible signal is given to indicate end of therapy.

Example 5 Purchasing Dosage Quotas and Report Generation

The methods and devices described are intended to be used by psychiatrists/therapists to treat patients with mental disorders. Psychiatrists who take advantage of this therapy can register accounts with a vendor of the devices described and be given a username and password. When a psychiatrist sees a patient with a disorder and the psychiatrist feels that the patient could benefit from the methods or devices described herein, the psychiatrist either orders a device or selects one that has been pre-purchased.

The psychiatrist (or administrative assistant) can plug a pMERT (NEST) device into a USB port on a PC connected to an internet. Using web access and their username/password, the psychiatrist can login to the NeoSync website. The pMERT (NEST) will be automatically detected by the NeoSync website, and any necessary software upgrades will be downloaded.

The psychiatrist can then order a number of dosage quotas for a particular disorder from the website, such as 15 20-minute therapy treatment, one per day, to treat depression. An encrypted key will be downloaded to the pMERT (NEST), which will be set to allow the dosage quotas requested by the psychiatrist. Once this occurs, the psychiatrist will automatically be billed based on the number and type of dosage quotas. The psychiatrist will then bill the patient (or eventually the patient's insurance) for the procedure. The patient can take the pMERT (NEST) device to his/her home to use the device in accordance with the therapy prescribed by the psychiatrist or the patient can be treated in the psychiatrist's office.

Once the patient has used up all the dosage quotas the psychiatrist has loaded onto the device, the patient returns to the psychiatrist with the pMERT (NEST) device. The psychiatrist will connect the pMERT (NEST) device to the PC via a USB cable and will login to the NeoSync website as before. The website will detect the pMERT (NEST) and will upload all treatment information. A report can be generated with this information, giving the psychiatrist a quantitative indication of progress. The report can include for each treatment the date, start time, end time, initial EEG alpha parameters (i.e., power and Q-factor), and the final EEG alpha parameters. The psychiatrist can print the report or save it to a file to be placed in the patient's record. At this point, the psychiatrist can clear the memory of the device and use it for another patient or he/she can order more dosage quotas for the current patient.

If the psychiatrist decides that the patient should use the pMERT (NEST) for a longer period, the psychiatrist can set up an account for the patient with NeoSync, Inc. This way, the patient is able to order more dosage quotas without returning to the psychiatrist. Only the dosage quotas approved by the psychiatrist will be allowed for the patient to order. The patient can pay NeoSync directly with a credit card or (eventually) insurance. For each session, the psychiatrist may also be paid. The psychiatrist would have access to all reports uploaded from the pMERT (NEST) via the website.

Example 6

Each patient admitted to the study is randomly assigned into one of the two study groups based on treatment using a plugged pMERT (NEST) device and sham, where a pMERT (NEST) device rotates a non-magnetic metal block instead of a magnet. Patients are kept blind to the treatment condition. Each treatment consists of 22 daily sessions during a 30-day period (and/or at least 10 sessions during a 2 week period or more). Patients' current antipsychotic treatments are kept unchanged during the study.

EEG data during treatments are recorded and individualized according to the alpha EEG intrinsic frequency (8-13 Hz). The precision of the stimulus rate can be refined to the level of 10% of a hertz. It is determined on each patient's average alpha frequency, obtained from 3 central EEG leads (C3, C4, and Cz).

EEG data during treatments are recorded from each subject in a supine position with their eyes closed throughout the testing period. Nineteen EEG electrodes (Ag—Ag Cl) are used according to the International 10-20 system and referenced to linked mastoids. Electrooculograms (EOGs) from the outer canthus of both eyes are recorded simultaneously to monitor eye movements. At least two minutes of EEG epochs are collected and digitized by a 12-bit A/D (analog/digital) converter at the rate of 200 Hz by a Cadwell EZ II acquisition system. Sixty seconds of artifact free epochs are utilized for fast Fourier transformations (FFT). FFT window is set at 512 data points with 80% overlap.

Severity of psychosis, depression, and movement disorders are assessed with the Hamilton Anxiety Scale (HAMA), the Hamilton Depression Scale (HAMD), PANSS, Montgomery-Asberg Depression Rating Scale (MADRS), Barnes Akathisia Rating Scale (BARS), and Simpson-Angus Scale (SAS), respectively. All rating scales and EEGs are administered at screening, baseline (immediately prior to first treatment), immediately following the fifth and tenth treatments.

While the technician administering the pMERT (NEST) device cannot be blinded, the evaluating physicians and EEG technicians remain unaware of the type of treatment throughout the duration of study. A priori categorical definition for clinical response is >30% baseline-to-post treatment reduction at the end of treatment on PANSS negative symptom subscale.

Patients with a baseline and at least 1 additional set of completed assessments (at least 5 treatment sessions) are included in the analysis of mean treatment effect. Efficacy in clinical ratings is evaluated by using analyses of variance (ANOVA) with repeated measure over time. The models include 2 between-subject factors of treatment and location, and 1 within-subject factors of time. Effect of concomitant antipsychotic treatment can be tested based on the categorization of typical and atypical neuroleptic medications. Grouping differences of all other measures are tested individually using the same statistical model. Using a predefined response criterion, a contingent table analysis can be used to test the group difference in responding rate.

Raw EEG data are edited offline by an experienced technician who is blind to the treatment conditions to eliminate any significant (>3_arc) eye movements or any other type of apparent artifact. Ten to twenty-four artifact-free epochs (1,024 data points per epoch) in each recording channel are calculated by a fast Fourier transform (FFT) routine to produce a power spectrum with 0.2 Hz frequency resolution. The intrinsic frequency of alpha EEG is defined as the mean peak frequency (Fp) of 3 central leads (C3, C4, and Cz). EEG variables used in the analysis included power density (Pwr), peak frequency (Fp), Fp longitudinal coherence, and frequency selectivity (Q). See Jin Y et al. Alpha EEG predicts visual reaction time. *Int J Neurosci.* 116: 1035-44 (2006), which is incorporated by reference in its entirety.

Coherence analysis is carried out between Fz and Pz in the peak alpha frequency. Recording from Cz is chosen to calculate the Q-factor (peak freq/half-power bandwidth), a measure of the alpha frequency selectivity. It is measured in the frequency domain by using a 60 sec artifact free EEG epoch and a 2,048 data point FFT with a 10-point smooth procedure. Multivariate analysis of variance (MANOVA) across all channels for each variable is performed to test the treatment and stimulus location effects. Change score for each variable before and after pMERT (NEST) treatment is used to correlate with the change score of each clinical measure from the same time points.

FIG. 12 shows an example of the Q-factor as used in this invention. The figure shows a sample graph of the frequency distribution of the energy of an EEG signal. It can be seen that a frequency range, $\Delta f$ can be defined as the frequency bandwidth for which the energy is above one-half the peak energy. The frequency $f_0$ is defined as the intrinsic frequency in the specified band. The Q-factor is defined as the ratio of $f_0/\Delta f$. As can be seen, when $\Delta F$ decreases for a given $f_0$, the Q-factor will increase. This can occur when the peak energy $E_{max}$ of the signal increases or when the bandwidth of the EEG signal decreases.

Example 7: Effect of NEST Device Lowering Blood Pressure

An effect of use of a NEST (i.e. pMERT) device using a method provided herein was shown to lower blood pressure in a female patient. The patient, originally using a NEST to treat anxiety, complained of a moderate tension headache and her blood pressure was taken, and read at 110/90 mmHg. A NEST device was set at a fixed specified frequency equal to an intrinsic frequency within her alpha EEG band and the magnetic field emanating from the device was applied to the patient's head (cerebral cortex). During treatment using the NEST device, three consecutive blood pressure measurements were taken at ten minute intervals, showing 110/85 mmHg, 100/82 mmHg, and 100/70 mmHg, respectively. An hour after treatment with the NEST device had ceased, the patient's tension headache returned, and her blood pressure was measured, reading 110/90 mmHg.

Example 8

In particular embodiments, a single cylindrical magnet that is diametrically magnetized (pole on the left and right sides of the cylinder) spins about the cylinder axis. The magnet can be placed anywhere around the patient's head, and locations can be chosen based on the desire for a more focal therapy at a particular location. Alternative embodiments can include stringing two or more cylindrical magnets together on the same shaft, or along different shafts, to spin the magnets in unison to create a particular magnetic field in treating the patient. A non-limiting examples of this are found in FIGS. 13 through 15.

Figure 13:
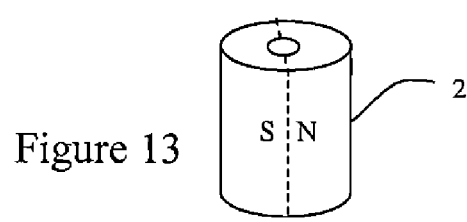
FIG. 13 shows an example embodiment of a diametrically magnetized cylindrical magnet for use in a NEST device.
Figure 14:
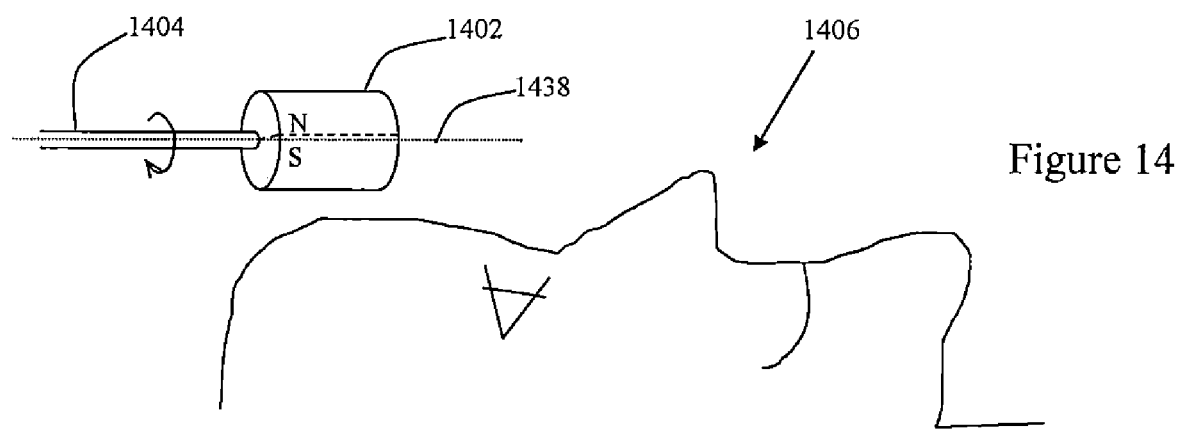
FIG. 14 shows an example embodiment of a NEST device having a diametrically magnetized cylindrical magnet rotating about its cylinder axis and applied to a subject.
Figure 15:
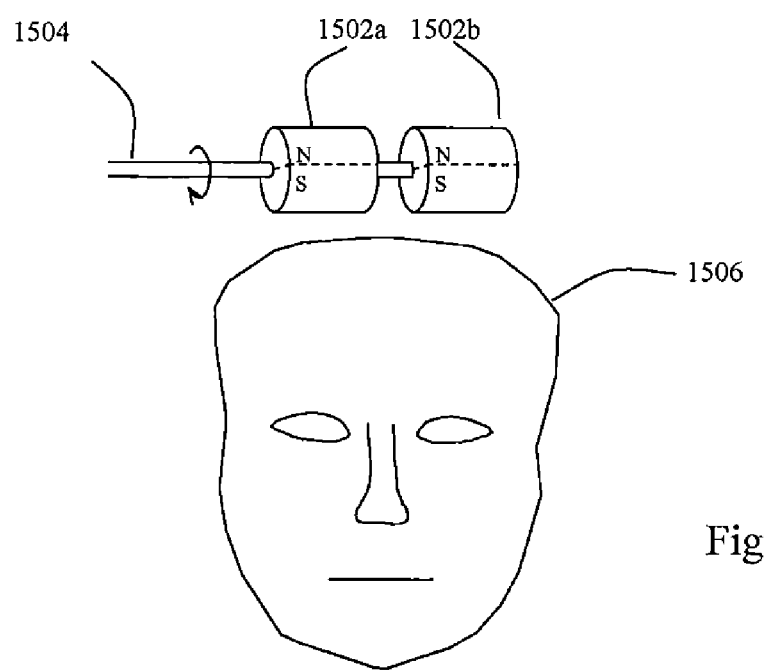
FIG. 15 shows an example embodiment of a NEST device having two diametrically magnetized cylindrical magnets rotating about their cylinder axes and applied to a subject.

FIG. 13 shows an example embodiment of a diametrically magnetized cylindrical magnet 2 for use in a NEST device. FIG. 14 shows an example embodiment of a NEST device applied to a subject 1406, the device having a diametrically magnetized cylindrical magnet 1402 and a drive shaft 1404 that rotates the magnet 1402 about its cylinder axis, wherein the cylinder axis coincides with rotation axis 1438. FIG. 15 shows an example embodiment of a NEST device applied to a subject 1506, the device having two diametrically magnetized cylindrical magnets 1502a, 1502b and a drive shaft 1404 that simultaneously rotates the magnets 1502a, 1502b about their cylinder axes, wherein the cylinder axes are coincident with each other and with rotation axis. In this example embodiment device, the north pole of magnet 1502a and the north pole of magnet 1502b are aligned to provide a more uniform magnetic field to the subject 1506.

Example 9

In particular embodiments, multiple cylindrical magnets can be arrayed above a patient's head so they spin in unison. These may be connected to each other by belts or gears so that they are driven by at least one motor. Non-limiting examples of these embodiments are shown in FIGS. 16 through 21.

Figure 16:
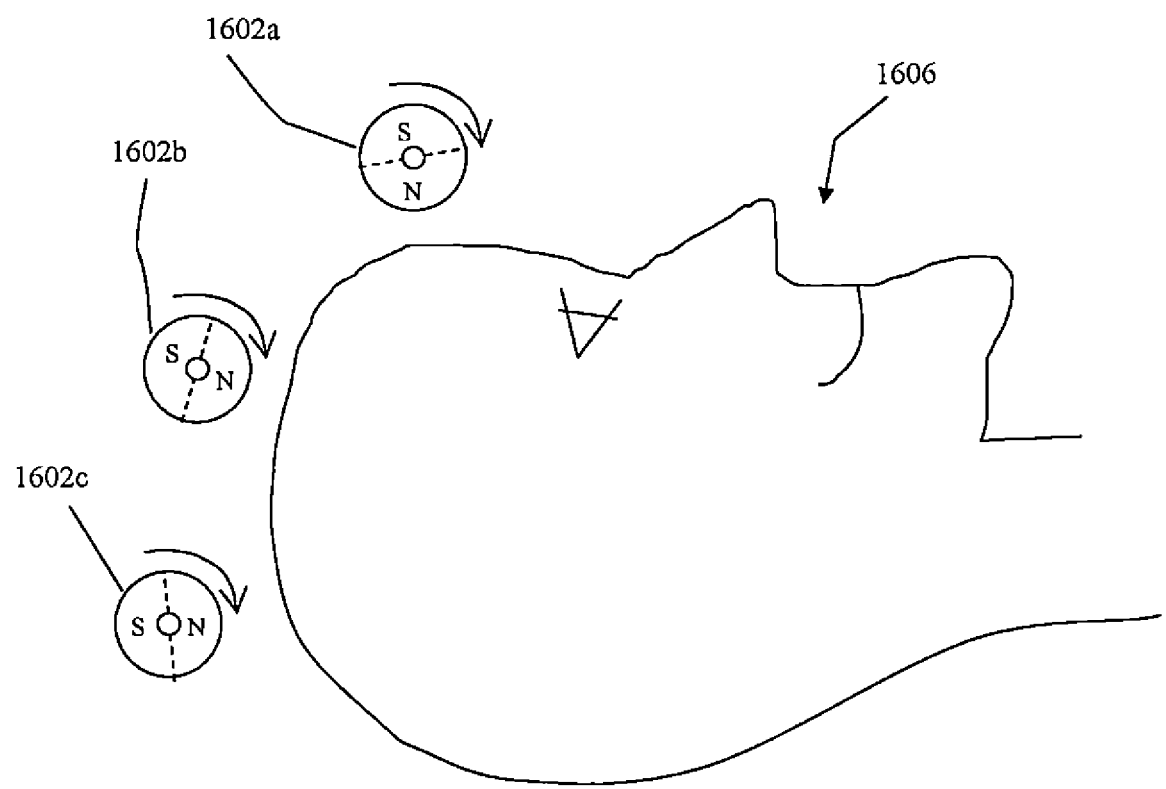
FIG. 16 shows an example embodiment of a NEST device having three diametrically magnetized cylindrical magnets rotating about their cylinder axes and applied to a subject.

FIG. 16 shows an example embodiment of a NEST device having three diametrically magnetized cylindrical magnets 1602a, 1602b, 1602c rotating about their cylinder axes and applied to a subject 1606. The poles of each the magnets 1602a, 1602b, 1602c of the shown device are aligned generally to provide a peak magnetic field to the subject 1606 that is coincident with the peak magnetic fields delivered to the subject 1606 from each of the other magnets 1602a, 1602b, 1602c. Another way of saying this is that each of the magnets 1602a, 1602b, 1602c has a neutral plane indicated by the dotted line on each of magnets 1602a, 1602b, and 1602c, and each the neutral planes is aligned to be generally parallel to the scalp of the subject 1606. This configuration provides a more uniform field to the subject 1606 than if the magnets 1602a, 1602b, 1602c are not aligned in such a manner.

Figure 17:
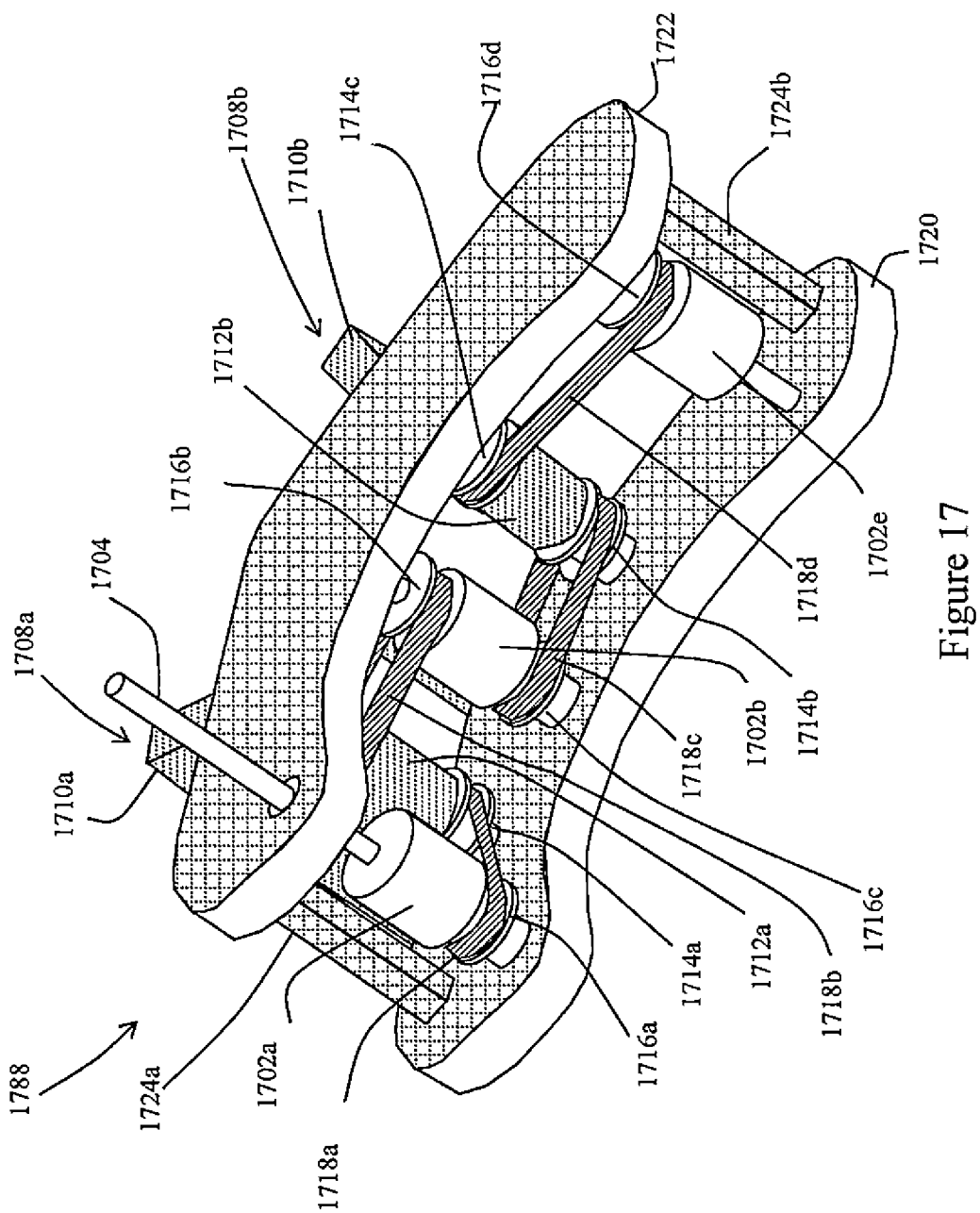
FIG. 17 shows an example embodiment of a NEST device having three diametrically magnetized cylindrical magnets configured to rotate about their cylinder axes.

FIG. 17 shows an example embodiment of a NEST device 1788 having three diametrically magnetized cylindrical magnets 1702a, 1702b, 1702c configured to rotate about their cylinder axes (not shown). Each of the magnets 1702a, 1702b, 1702c of this example embodiment is coupled to at least one magnet drive pulley 1716a, 1716b, 1716c, 1716d. Each of the magnet drive pulleys 1716a, 1716b, 1716c, 1716d has at least one drive belt 1718a, 1718b, 1718c, 1718d wrapped at least partially about it. The device 1788 also comprises two tensioner assemblies 1708a, 1708b, each comprising a tensioner block 1710a, 1710b, a tensioner arm 1712a, 1712b, and at least one tensioner drive pulley 1714a, 1714b, 1714c each rotating about an axis going through the tensioner arm 1712a, 1712b, respectively, the axis generally being parallel to the rotation axis of the magnets and to the drive shaft 1704 of the device 1788. In the embodiment shown in FIG. 17, each of the tensioner assemblies has two tensioner drive pulleys 1714a, 1714b, 1714c, (one tensioner drive pulley of tensioner assembly 1708 is not shown in FIG. 17—obscured by the side support 1722, but can be seen, for example, in FIG. 18). The drive belts 1718a, 1718b, 1718c, 1718d are each also wrapped at least partially about at least one tensioner drive pulley 1714a, 1714b, 1714c, (one tensioner drive pulley of tensioner assembly 1708 is not shown in FIG. 17—obscured by the side support 1722), such that each the drive belts 1718a, 1718b, 1718c, 1718d is wrapped at least partially around at least one of the magnet drive pulleys 1716a, 1716b, 1716c, 1716d and is also wrapped at least partially around at least one of the tensioner drive pulleys 1714a, 1714b, 1714c, (one tensioner drive pulley of tensioner assembly 1708 is not shown in FIG. 17—obscured by the side support 1722, but can be seen, for example, in FIG. 18) of the tensioner subassemblys 1708a, 1708b.

The device 1788 shown in FIG. 17 is held together by two side supports 1722, 1720 connected by a support column 1724a. In some embodiments, a second support column 1724b, a third support column (not shown) may also connect the side supports 1722, 1720. Each of the tensioner assemblies 1708a, 1708b and each of the magnets 1702a, 1702b, 1702c are mounted to (coupled to) at least one of these supports, if not both the side supports 1722, 1720. Each of the magnets 1702a, 1702b, 1702c are rotatably mounted to at least one of the side supports 1722, 1720, such that each of the magnets 1702a, 1702b, 1702c can rotate about their rotation axes (cylinder axes) without motion of either of the side supports 1722, 1720. Likewise, at least the tensioner drive pulleys 1714a, 1714b, 1714c, (and one tensioner drive pulley unshown in FIG. 17) of the tensioner assemblies 1708a, 1708b are rotatably mounted (coupled) to at least one of the side supports 1722, 1720, such that each of the tensioner drive pulleys 1714a, 1714b, 1714c, (and one tensioner drive pulley unshown in FIG. 17) can rotate about their rotation axes (not shown) without motion of the side supports 1722, 1720.

For example, drive belt 1718a wraps at least partially around the magnet drive pulley 1716a of magnet 1702a, and also wraps at least partially around the tensioner drive pulley 1714*a* of the first tensioner assembly 1708*a*. The drive shaft 1704, coupled to a motor (not shown), drives the rotation of all of the magnets 1702*a*, 1702*b*, 1702*c* of the shown device 1788. The drive shaft 1704 is coupled to a first magnet 1702*a* which, through its magnet drive pulley 1716*a* and associated belt 1718*a* turns the first tensioner drive pulley 1714*a* of the first tensioner assembly 1708*a*. The first tesnioner drive pulley 1714*a* of the first tensioner assembly 1708*a* is coupled to the second tensioner pulley (not shown-obscured by side support 1722) of the first tensioner assembly 1708*a*, and, thus, when the first tensioner pulley 1714*a* is turned by the first drive belt 1718*a*, the second tensioner pulley (not shown) is also turned. Since the second drive belt 1718*b* is wrapped at least partially around the second tensioner pulley (not shown) as well as the second magnet drive pulley 1716*b* of the second magnet 1702*b*, the motion of the second tensioner pulley (not shown) moves the second drive belt 1718*b* and likewise drives the rotation of the second magnet 1702*b*. The second magnet 1702 has a third magnet drive pulley 1716*c* which is coupled to the second drive pulley 1716*b*, and the third drive belt 1718*c* wraps at least partially around the third magnet drive pulley 1716*c*, thus, motion of the second drive belt 1718*b* also causes motion of the third drive belt 1718*c* wrapped at least partially around the third magnet drive pulley 1716*c*. The motion of the third drive belt 1718*c*, also wrapped at least partially around the third tensioner pulley 1714*b* of the second tensioner assembly 1708*b* thus drives the rotation of the fourth tensioner pulley 1714*c* of the second tensioner assembly 1708*b* which is coupled to the third tensioner pulley 1714*b* of the second tensioner assembly 1708*b*. Furthermore, since the fourth drive belt 1718*d* is wrapped at least partially around the fourth tensioner pulley 1714*c* of the second tensioner assembly 1708*b*, and is also wrapped at least partially around the fourth magnet pulley 1716*d* of the third magnet 1702*c*, the motion of the fourth drive belt 1718*d* drives the rotation of the third magnet 1702*c* simultaneously with the rotation of the other two magnets 1702*a*, 1702*b*.

In an alternative embodiment, the tensioner assemblies are not present, and the drive shaft drives the magnets connected only to each other using drive belts. In an alternative embodiment, only one tensioner assembly is present and is coupled to at least two magnets. In an alternative embodiment, only one tensioner assembly is present and is coupled to each of the magnets. In an alternative embodiment, the magnets are coupled to each other by gears. In an alternative embodiment, the magnets are coupled to each other by a combination of at least one gear and at least one belt. In an alternative embodiment, the magnets are coupled to each other by a combination of at least one gear and at least two belts, wherein each belt is coupled to a tensioner assembly as generally described herein. In an alternative embodiment, the magnets are coupled to each other by a rotation means, wherein the rotation means is configured to drive the rotation of the magnets simultaneously.

Figure 18:
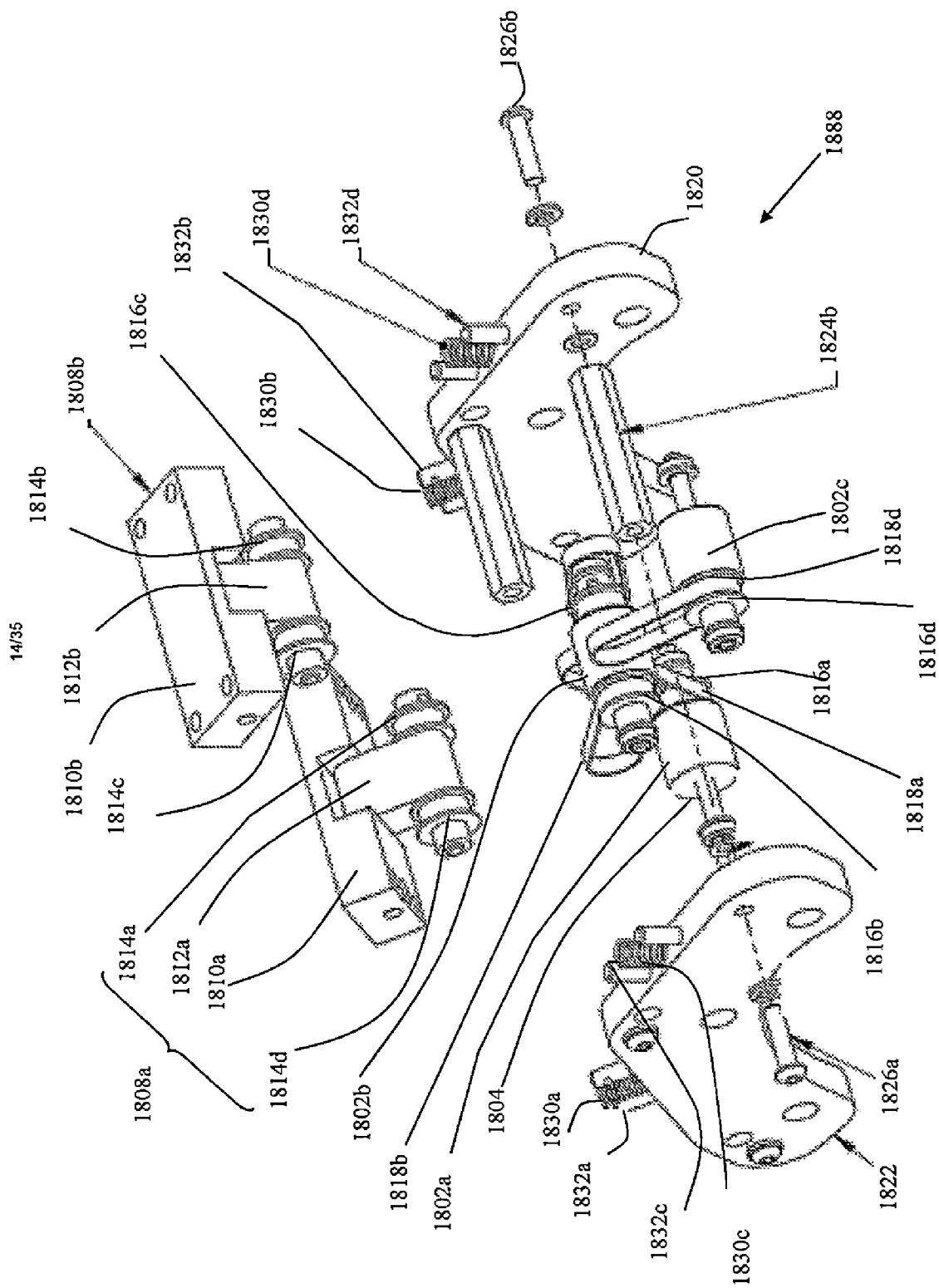
FIG. 18 shows an exploded view of the example embodiment of the NEST device of FIG. 17 having three diametrically magnetized cylindrical magnets configured to rotate about their cylinder axes.
Figure 19:
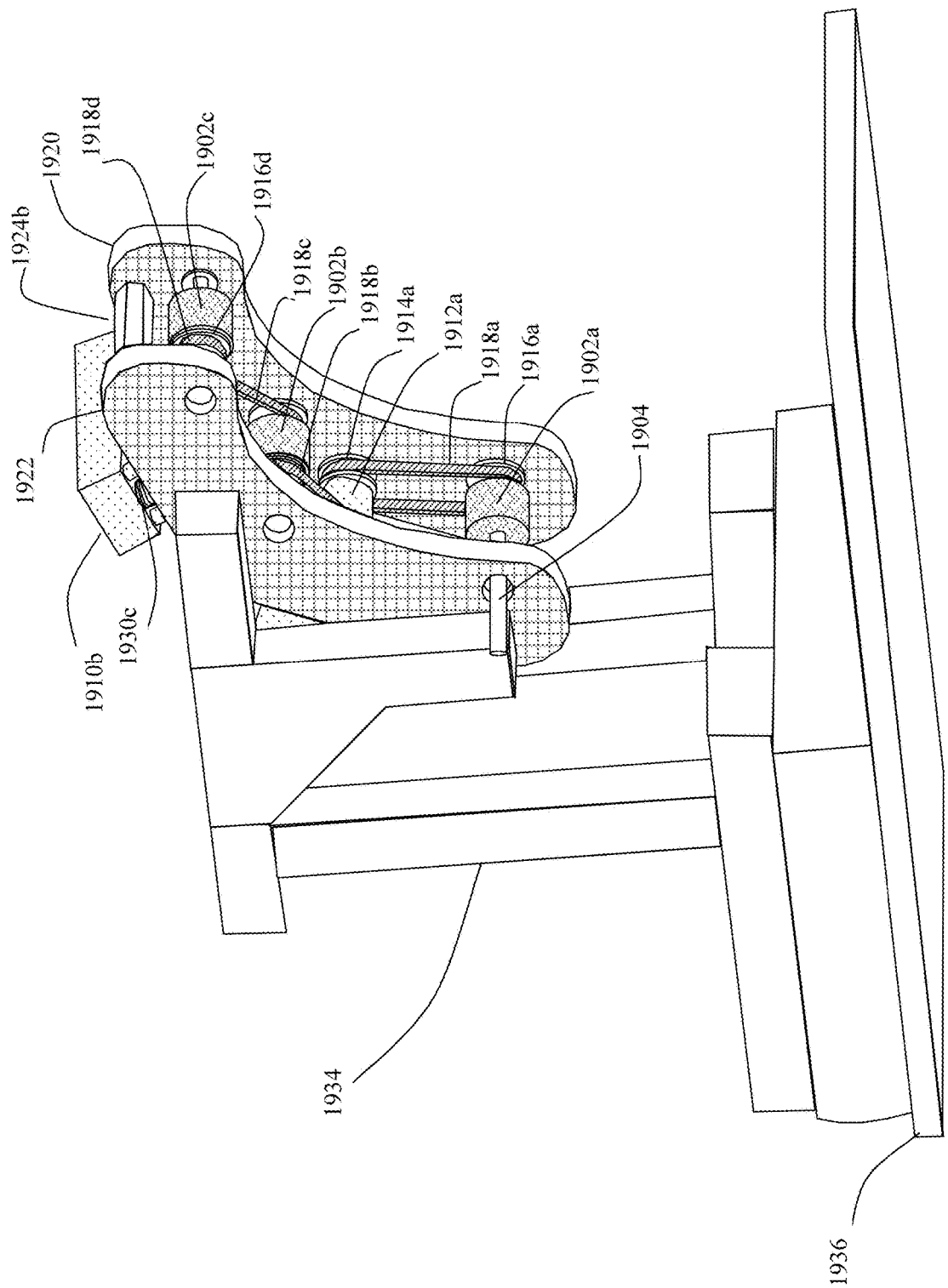
FIG. 19 shows the example NEST device embodiment of FIG. 17 having three diametrically magnetized cylindrical magnets configured to rotate about their cylinder axes and including a frame and base for mounting the NEST device.

The tensioner assemblies in the embodiments shown in FIG. 17, FIG. 18, and FIG. 19, for non-limiting example, are configured to keep the drive belts taut during use and, therefore, ensure that the rotation of the magnets is simultaneous and generally in-phase as applied to the subject where the magnets are aligned such that each of the neutral planes of each of the three magnets are generally aligned to be parallel to the scalp of the subject.

FIG. 18 depicts an exploded view of the example embodiment of the NEST device 1888 of FIG. 17 having three diametrically magnetized cylindrical magnets configured to rotate about their cylinder axes. Shown in FIG. 18 is a NEST device 1888 having two tensioner assemblies 1808*a*, 1808*b*. Tensioner assembly 1808*a* comprises a tensioner block 1810*a* that couples to the side support 1822 by at least one tensioner dowel pin 1832*a*. The tensioner block 1810*a* also couples to the side support 1820 by at least one tensioner dowel pin 1832*b*. The tensioner block 1810*a* floats freely along at least a portion of the dowel pins 1832*a*, 1832*b*. The tensioner block 1810*a* is attached to a tensioner arm 1812*a* which has two tensioner drive pulleys 1814*a*, 1814*d*, which couple to drive belts 1818*a*, 1818*b* (respectively) which themselves are coupled to magnets 1802*a*, 1802*b* (respectively) of the device 1888 through magnet drive pulleys 1816*a*, 1816*b*. The tensioner block 1810*a* exerts a force on the belts 1818*a*, 1818*b* to keep the belts taut during use, since the tensioner block 1810*a* is also coupled to tensioner springs 1830*a*, 1830*b* which push the tensioner block 1810*a* away from the side supports 1822, 1820, and thus, away from the magnet drive pulleys 1816*a*, 1816*b* coupled to the side supports 1822, 1820 by center pins (not shown) that run through each of the drive pulleys 1816*a*, 1816*b* and the magnets 1802*a*, 1802*b*. When the center pin is also attached to a motor, it may also rotate the magnet and its associated magnet drive pulley(s), and it may be called a drive shaft. Nevertheless, the magnet drive pulleys 1816*a*, 1816*b* can rotate, and with their rotational movement the magnet drive pulleys 1816*a*, 1816*b* can rotate, or be rotated by, the magnets 1802*a*, 1802*b*.

Likewise, tensioner assembly 1808*b* comprises a tensioner block 1810*b* that couples to the side support 1822 by at least one tensioner dowel pin 1832*c*. The tensioner block 1810*b* also couples to the side support 1820 by at least one tensioner dowel pin 1832*c*. The tensioner block 1810*b* floats freely along at least a portion of the dowel pins 1832*c*, 1832*d*. The tensioner block 1810*b* is attached to a tensioner arm 1812*b* which has two tensioner drive pulleys 1814*b*, 1814*c*, which couple to drive belts 1818*d*, 1818*c* (not shown) (respectively) which themselves are coupled to magnets 1802*b*, 1802*c*(respectively) of the device 1888 through the magnet drive pulleys 1816*c*, 1816*d*. The tensioner block 1810*b* exerts a force on the belts 1818*d*, 1818*c* (not shown) to keep the belts taut during use, since the tensioner block 1810*b* is also coupled to tensioner springs 1830*c*, 1830*d* which push the tensioner block 1810*b* away from the side supports 1822, 1820, and thus, away from the magnet drive pulleys 1816*c*, 1816*d* coupled to the side supports 1822, 1820 by center pins (not shown) that run through each of the drive pulleys 1816*c*, 1816*d* and the magnets 1802*b*, 1802*c*. When the center pin is also attached to a motor, it may also rotate the magnet(s) and its associated magnet drive pulley(s), and it may be called a drive shaft. Nevertheless, the magnet drive pulleys 1816*c*, 1816*d* can rotate, and with their rotational movement the magnet drive pulleys 1816*c*, 1816*d* can rotate, or be rotated by, the magnets 1802*b*, 1802*c*.

Also shown in FIG. 18 are support screws 1826*a*, 1826*b* which attach the support columns 1824*b* (other support columns are either not called-out or not shown in FIG. 18) to the side support 1822 and/or to the side support 1820.

FIG. 19 shows the example NEST device embodiment of FIG. 17 and/or of FIG. 18 having three diametrically magnetized cylindrical magnets 1902*a*, 1902*b*, 1902*c* configured to rotate about their cylinder axes and including a frame 1934 and base 1936 for mounting the NEST device. The embodiment shown in FIG. 19 includes a NEST device having three magnets 1902*a*, 1902*b*, 1902*c*, each having magnet drive pulleys 1916a, 1916b, 1916c, 1916d at least partially about which is wrapped a drive belt 1918a, 1918b, 1918c, 1918d each of which is also at least partially wrapped around a tensioner drive pulley 1914a, 1914b (not shown) 1914c (not shown) 1914d (not shown) coupled to a tensioner arm 1912a, 1912b (not shown) of a tensioner assembly. Each tensioner assembly may include a tensioner block 1910a (not shown) 1910b, and a tensioner spring 1930a (not shown), 1930c which cooperate with at least one of the side supports 1922, 1920 to pull the drive belts 1918a, 1918b, 1918c, 1918d taut. The magnets 1902a, 1902b, 1902c are rotatably coupled to side supports 1922, 1920, and at least one magnet 1902a in the embodiment shown is coupled to a drive shaft 1904 which rotates the magnet 1902a to which it is directly coupled, and through the cooperation of the magnet drive pulleys 1916a, 1916b, 1916c, 1916d, drive belts 1918a, 1918b, 1918c, 1918d, and tensioner drive pulleys 914a, 1914b (not shown) 1914c (not shown) 1914d (not shown), also rotates the other magnets 1902b, 1902c of the NEST device such that all of the magnets 1902a, 1902b, 1902c rotate simultaneously.

Figure 20:
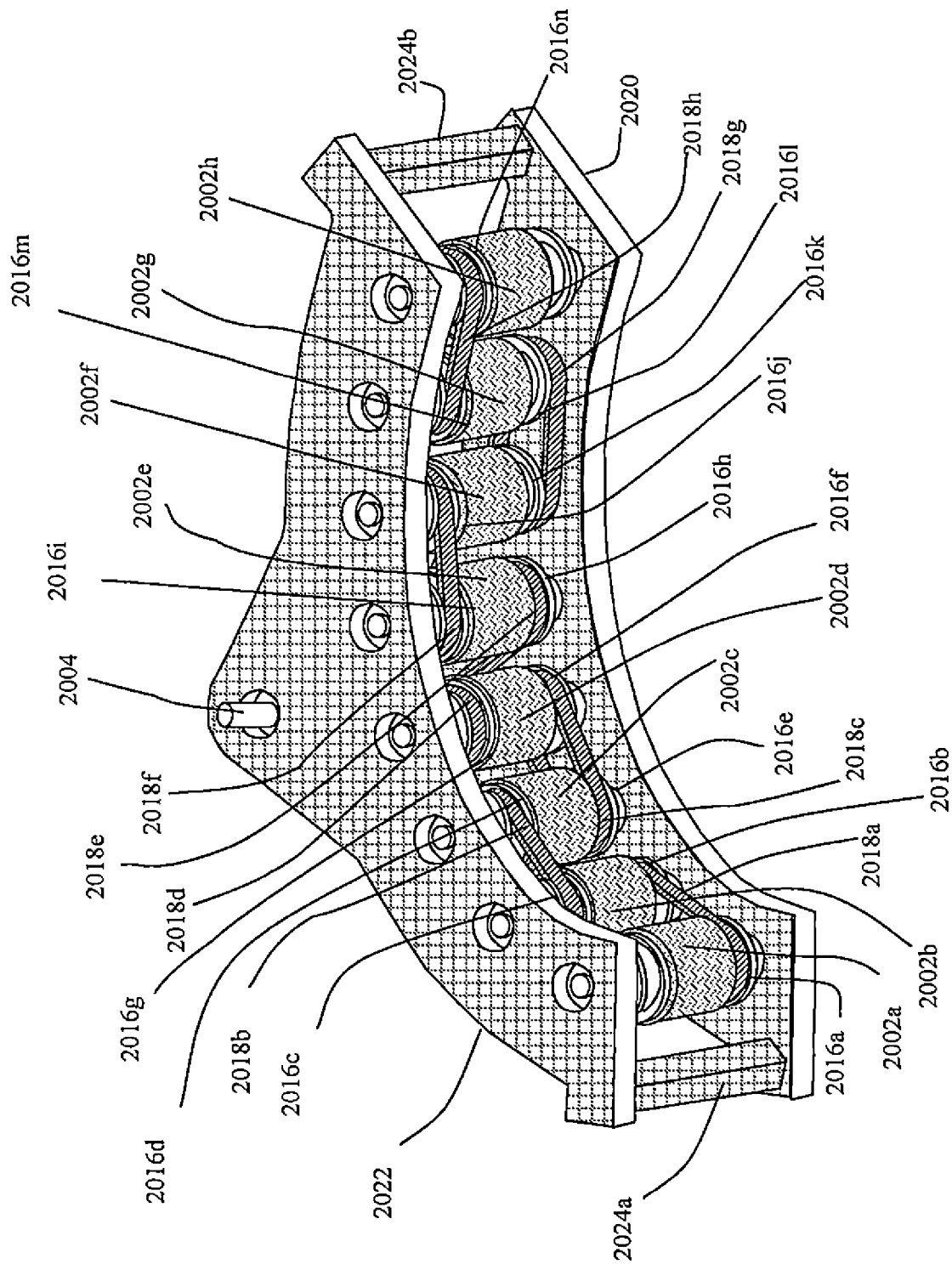
FIG. 20 shows an example embodiment of a NEST device having eight diametrically magnetized cylindrical magnets configured to rotate about their cylinder axes.

FIG. 20 shows an example embodiment of a NEST device having eight diametrically magnetized cylindrical magnets 2002a-2002h, configured to rotate about their cylinder axes. Each of the magnets 2002a-2002h has at least one magnet drive pulley 2016a-2016n coupled to it which rotates the magnet 2002a-2002h when the magnet drive pulley 2016a-2016n is rotated by a belt 2018a-2018h that is at least partially wrapped around at least one of the magnet drive pulleys 2016a-2016n. In the embodiment shown, a drive shaft 2004 has two drive belts 2018d, 2018e wrapped at least partially around the drive shaft 2004. The drive shaft 2004 thus rotates all of the magnets 2002a-2002h simultaneously through a series of drive belts 2018a-2018h and magnet drive pulleys 2016a-2016n all coupled to the drive shaft 2004.

For example, the first drive belt 2018e is wrapped at least partially around the drive shaft 2004, and is also wrapped at least partially around a first magnet drive pulley 2016h of a first magnet 2002e. A second drive belt 2018f is wrapped at least partially around a second magnet drive pulley 2016i of the first magnet 2002e. The second drive belt 2018f is also wrapped at least partially around a third magnet drive pulley 2016j of the second magnet 2002f. A third drive belt 2018g is wrapped at least partially around a fourth magnet drive pulley 2016k of the second magnet 2002f. The third drive belt 2018g is also wrapped at least partially around a fifth magnet drive pulley 2016l of a third magnet 2002g. A fourth drive belt 2018h is wrapped at least partially around a sixth magnet drive pulley 2016m of the third magnet 2002g. The fourth drive belt 2018h is also wrapped at least partially around a seventh magnet drive pulley 2016n of a fourth magnet 2002h. As arranged, therefore, the motion of the first drive belt 2018e coupled to the drive shaft 2004 rotates the first magnet 2002e, the second magnet 2002f, the third magnet 2002g, and the fourth magnet 2002h simultaneously.

Similarly, the fifth drive belt 2018d is wrapped at least partially around the drive shaft 2004, and is also wrapped at least partially around an eighth magnet drive pulley 2016g of a fifth magnet 2002d. A sixth drive belt 2018c is wrapped at least partially around a ninth magnet drive pulley 2016f of the fifth magnet 2002d. The sixth drive belt 2018c is also wrapped at least partially around a tenth magnet drive pulley 2016e of the sixth magnet 2002c. A seventh drive belt 2018b is wrapped at least partially around an eleventh magnet drive pulley 2016d of the sixth magnet 2002c. The seventh drive belt 2018b is also wrapped at least partially around a twelfth magnet drive pulley 2016c of a seventh magnet 2002b. An eighth drive belt 2018a is wrapped at least partially around a thirteenth magnet drive pulley 2016b of the seventh magnet 2002b. The eighth drive belt 2018a is also wrapped at least partially around a fourteenth magnet drive pulley 2016a of an eighth magnet 2002a. As arranged, therefore, the motion of the fifth drive belt 2018d coupled to the drive shaft 2004 rotates the fifth magnet 2002d, the sixth magnet 2002c, the seventh magnet 2002b, and the eighth magnet 2002a simultaneously. In an alternative embodiment, the drive shaft has only one drive belt that drives all of the rotation of all of the magnets. Also shown in FIG. 20 are the side supports 2022, 2020 connected by at least two support columns 2024a, 2024b. The supports 2020, 2022 hold each of the magnets 2002a-2002h in place relative to the supports 2020, 2022 while allowing rotational motion of the magnets 2002a-2002h and of the drive shaft 2004 which may me driven, for non-limiting example, by a motor (not shown).

Figure 21:
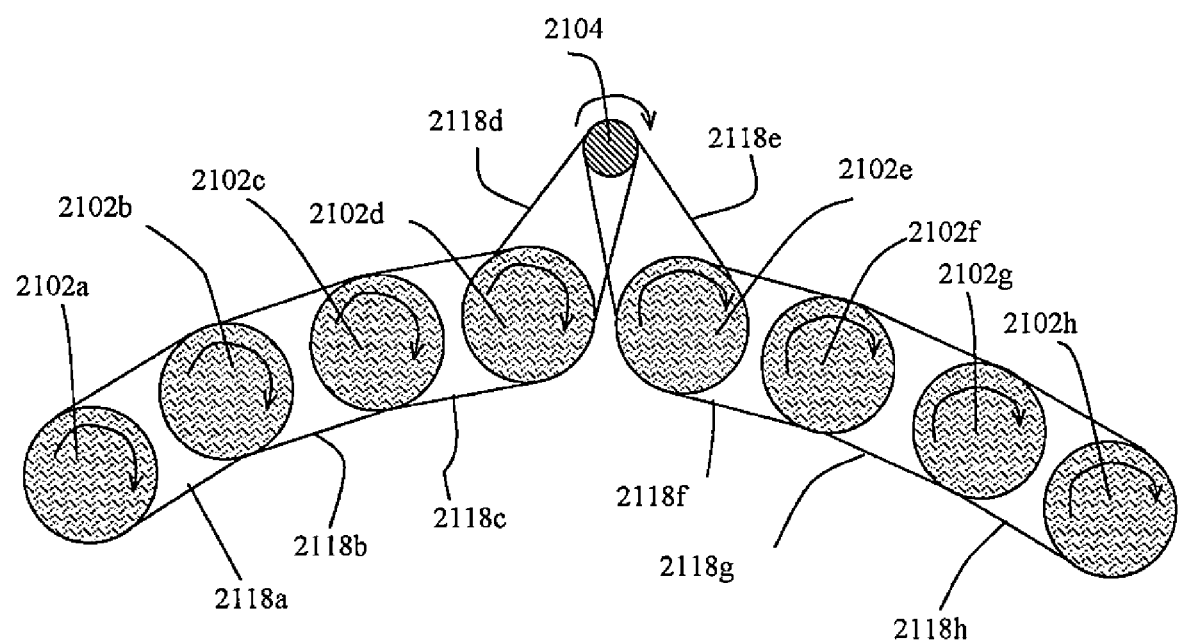
FIG. 21 shows the magnet rotation of the example NEST device embodiment of FIG. 20 having eight diametrically magnetized cylindrical magnets configured to rotate about their cylinder axes.

FIG. 21 shows the magnet rotation of the example NEST device embodiment of FIG. 20 having eight diametrically magnetized cylindrical magnets 2102a-2102h configured to rotate about their cylinder axes. FIG. 21 shows a side view of an embodiment of a NEST device (not showing, for example, side supports), which is similar to the embodiment shown in FIG. 20. In this embodiment, each of the magnets 2102a-2102h has at least two drive belts (for example, drive belts 2118a-2118h) coupled to it which rotate the magnet 2102a-2102h, or which are rotated by the magnet 2102a-2102h, when the drive shaft 2104 is rotated. In the embodiment shown, two drive belts 2118d, 2118e are wrapped at least partially around the drive shaft 2104. The drive shaft 2104 thus rotates all of the magnets 2102a-2102h simultaneously through a series of drive belts 2118a-2118h all coupled to the drive shaft 2104. Shown in this embodiment is an example of the direction of rotation of the magnets 2102a-2102h (indicated by arrows) resulting from a clockwise rotation of the drive shaft 2104. An opposite direction of movement is achieved when the drive shaft is rotated in a counter-clockwise direction. In the embodiment shown, the clockwise rotation of the drive shaft 2104 rotates all of the magnets 2102a-2102h in a clockwise direction due to the belt 2118a-2118h arrangement shown. Each of the belts 2118a-2118h shown is wrapped either around two magnets or around a magnet and the drive shaft.

Example 10

In particular embodiments, a disc shaped magnet that is axially magnetized (the poles are on the top and bottom faces) can be cut in half, one half turned over (aligning N of one half with S of the other half) and placed together. This disc can be spun about the center of the disc to get a magnetic field that is uniform over a large area. In a similar embodiment, two rectangular magnets having poles aligned and positioned similarly to the disc as previously described can be spun about the center of the rectangular magnets to create a similarly uniform field. An example of the disc magnet is shown in FIG. 22, and an example of the rectangular magnet similar to the disc magnet is shown in FIG. 23.

Figure 22:
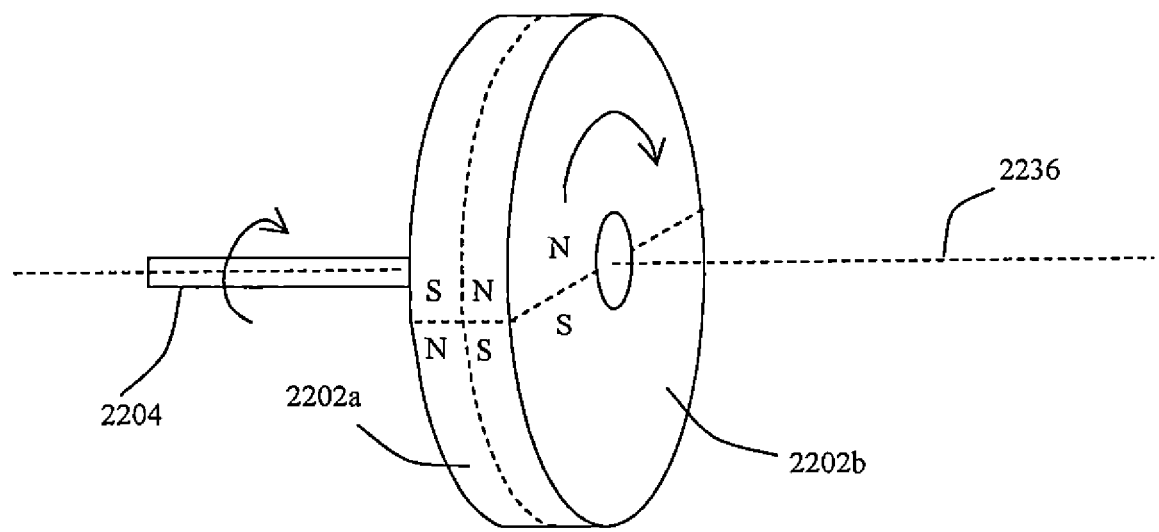
FIG. 22 shows an example embodiment of a NEST device having two axially polarized half-disc magnets that rotate about a common rotation axis.

FIG. 22 shows an example embodiment of a NEST device having two disc magnets 2202a, 2202b that rotate about a common rotation axis 2236. The device comprises two disc shaped magnets 2202a, 2202b that are axially magnetized (the poles are on the top and bottom faces). The north pole of the first magnet 2202a aligns with the south pole of the second magnet 2202b (aligning their neutral planes). The device further comprises a drive shaft 2204 that aligns with the center of the disc magnets 2202a, 2202b and with, therefore, the rotation axis 2236 of the magnets 2202a, 2202b.

Figure 23:
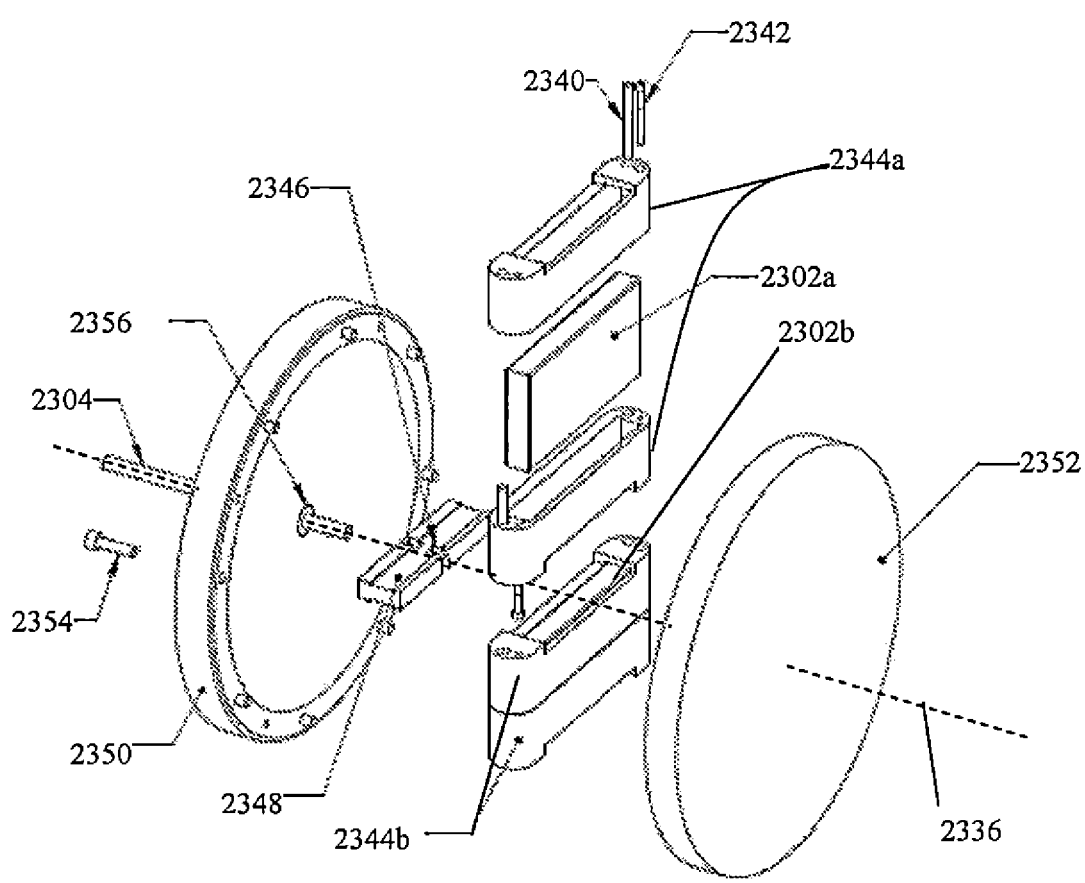
FIG. 23 shows an exploded view of an alternate embodiment of an example NEST device embodiment similar to that of FIG. 22 having two rectangular magnets that rotate about a common rotation axis.

FIG. 23 shows an exploded view of an alternate embodiment of an example NEST device embodiment similar to that of FIG. 22 having two rectangular magnets 2302a, 2302b that rotate around a common rotation axis 2336. The device comprises two rectangular magnets 2302a, 2302b that are magnetized such that the north pole of the first magnet 2302a faces away from the drive shaft 2304, and the south pole of the first magnet 2302a faces the drive shaft 2304, and the north pole of the second magnet 2302b faces the drive shaft 2304 while the south pole of the second magnet 2302b faces away from the drive shaft 2304. The poles of each of the magnets 2302a, 2302b, thus, face the top cover 2352 and the bottom cover 2350 of the device, but the magnets 2302a, 2302b, have opposite polarity. In the embodiment shown, the first magnet 2302a is held in place in the device by a first magnet holder 2344a having two pieces that are connected by a magnet holder cap screw 2342 and a magnet holder dowel pin 2340. The first magnet 2302a is placed between and at least partially within the pieces of the first holder 2344a. Likewise, the second magnet 2302b is held in place in the device by a second magnet holder 2344b having two pieces that are connected by a magnet holder cap screw (not shown) and a magnet holder dowel pin (not shown). The second magnet 2302b is placed between and at least partially within the pieces of the second holder 2344b. The two holders 2344a, 2344b are coupled together, and may have a center beam 2348 that holds the first and second holders 2344a, 2344b together. The holders 2344a, 2344b may also be held together additionally or alternatively by adhesive 2346. The drive shaft 2304 is coupled to the holders 2344a, 2344b, in the embodiment shown, by attaching to the center beam 2348, which thus couples the magnets 2302a, 2302b to the drive shaft 2304 such that rotation of the drive shaft 2304 likewise spins the magnets 2302a, 2302b within the holders 2344a, 2344b about the rotation axis 2336. The drive shaft 2304 may alternatively and/or additionally be coupled to the holders 2344a, 2344b and to the center beam 2348 by adhesive 2346. The magnets 2302a, 2302b encased in the holders 2344a, 2344b are additionally housed within a top cover 2352 and a bottom cover 2350. The covers 2350, 2352 are connected to one another by at least one cover cap screw 2354. The drive shaft 2304 fits through at a hole 2356 in at least one of the covers, for example, the bottom cover 2350. Where the cover 2350 is disc-shaped, as shown in FIG. 23, the hole 2356 is located the center of the disc cover 2350, and the hole 2356 is configured such that the drive shaft 2304 may rotate freely within the hole 2304, for example, with aid of a bearing which allows drive shaft rotation (and, thus, magnet rotation) relative to the covers 2350, 2352.

Example 11

Figure 24:
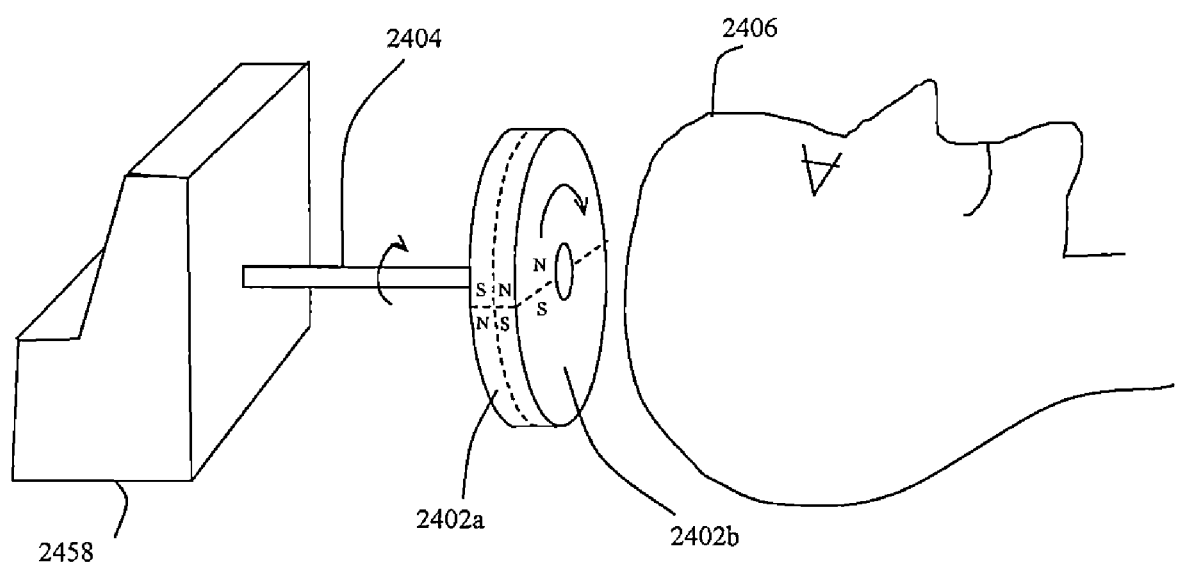
FIG. 24 shows an example embodiment of a NEST device similar to the embodiments depicted in FIGS. 22 and/or 23 having two magnets rotating about a common rotation axis applied to a subject and showing the controller subunit.

FIG. 24 shows an example embodiment of a NEST device similar to the embodiments depicted in FIGS. 22 and/or 23 having two magnets 2402a, 2402b rotating about a common rotation axis applied to a subject 2406 and showing the controller subunit 2458 coupled to a drive shaft 2404 that rotates the magnets 2402a, 2402b. The controller subunit 2458 may contain a motor (not shown) that cooperates with the drive shaft 2404 to rotate the magnets 2402a, 2402b.

Figure 25:
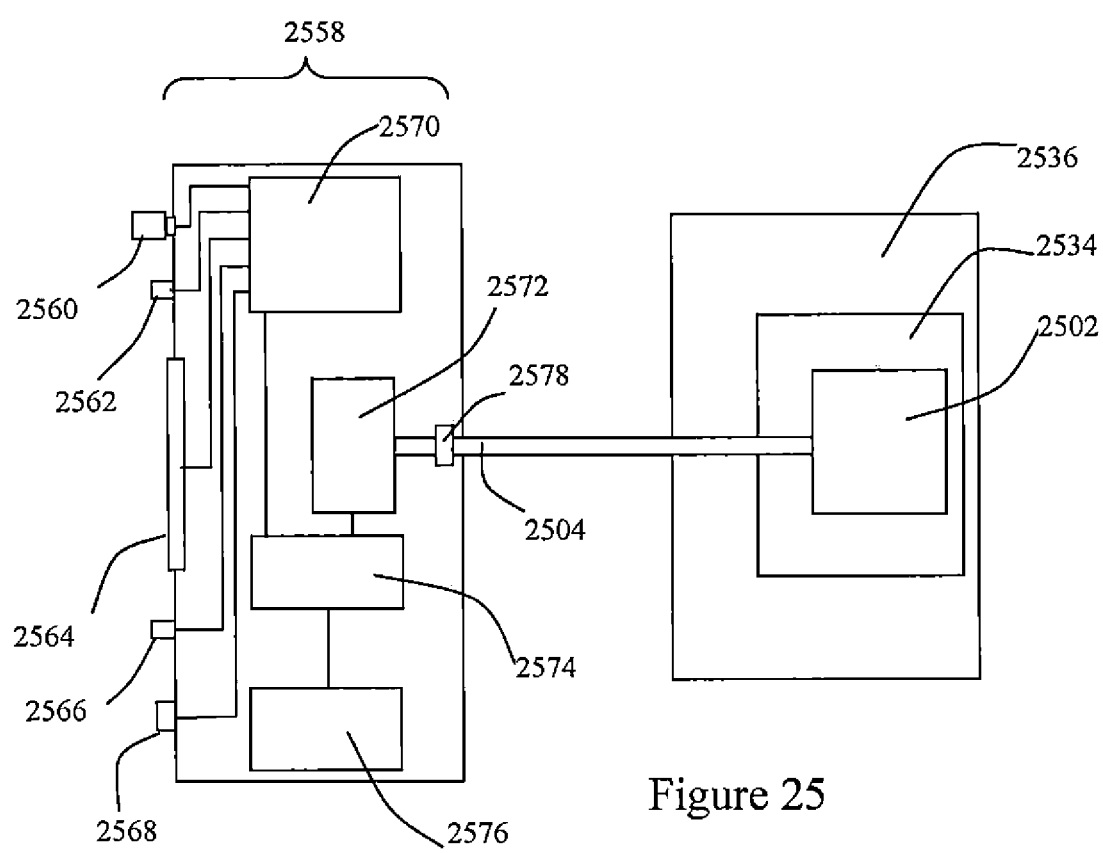
FIG. 25 shows block diagram of an example embodiment of a NEST showing the elements of the NEST device and its controller subunit.

FIG. 25 shows block diagram of an example embodiment of a NEST device showing example elements of the NEST device and of its controller subunit. For example the embodiment shown depicts a magnet 2502 that is mounted by a frame 2534 to a base 2536. This allows the magnet 2502 to be held stationary as the device treats a subject whose head may be positioned near to the magnet 2502 (within the magnetic field produced by the magnet 2502). The magnet 2502 is coupled to the controller subunit 2558 by a drive shaft 2504. The drive shaft 2504 may couple to a motor 2572 of the controller subunit 2558 by a coupling 2578. The coupling may allow for various magnet arrangements to be interchanged by merely decoupling the drive shaft from the controller subunit and coupling a device having another arrangement of magnets (such as, for example, those described herein). The magnet 2502 may be controlled by the controller subunit 2558 through the motor 2572 that may be driven by a motor driver 2574. The motor driver 2574 may be coupled (directly or indirectly) to a power supply 2576. The motor driver 2574, which can control, for non-limiting example, the speed, direction, acceleration, etc, of the magnet 2502 through the drive shaft 2504, can be directed and/or monitored by controls such as, for example, a device speed control 2560, an on/off control 2562, a display 2564, a random/continuous control 2566, and a high/low control 2568. A user can adjust each of these controls, which are coupled to a processor circuit board 2570 and thus coupled to the motor driver 2574.

Alternatively, and/or additionally, the drive shaft 2504 and/or the magnet(s) may be controlled automatically based on a prescribed treatment (time of treatment, frequency of magnet rotation, etc) that is downloaded and/or programmed into the processor circuit board 2570 from a source external or internal to the controller subunit, as previously described herein. Treatments received may be stored by the controller subunit. Additionally and/or alternatively, where EEG electrodes are also present in the device and are capable of measuring the subject's brain waves, the device may adjust the treatment automatically by a biofeedback system. Additionally and/or alternatively, where EEG electrodes are present in the device and are capable of measuring the subject's brain waves, the treatment may be chosen based on the readings of the subject's brain waves prior to the treatment. Additionally and/or alternatively, where EEG electrodes are present in the device and are capable of measuring the subject's brain waves, the treatment may be chosen automatically by the device based on the readings of the subject's brain waves prior to the treatment and based on a set of rules stored in the controller subunit. Additionally and/or alternatively, where EEG electrodes are present in the device and are capable of measuring the subject's brain waves, the controller subunit is capable of storing the output of the EEG electrodes prior to, during, and/or after treatment with the NEST device. Additionally and/or alternatively, where EEG electrodes are present in the device and are capable of measuring the subject's brain waves, the controller subunit is capable of transmitting the output of the EEG electrodes prior to, during, and/or after treatment with the NEST device. This transmitting may be real-time (during measurement), or after storage of the EEG electrode outputs and during an upload or download from the NEST device.

Example 12: Effect of a Device Lowering Blood Pressure

An effect of use of a modified rTMS device according to the methods and device descriptions provided herein was shown to reduce the symptoms of fibromyalgia. The patient complained of chronic widespread pain and tenderness to light touch, and was diagnosed with fibromyalgia. The NEST device was used to tune an intrinsic frequency (of the patient's alpha wave). Following treatment, the patient reported a reduction of the symptoms of fibromyalgia.

Example 13

Figure 26:
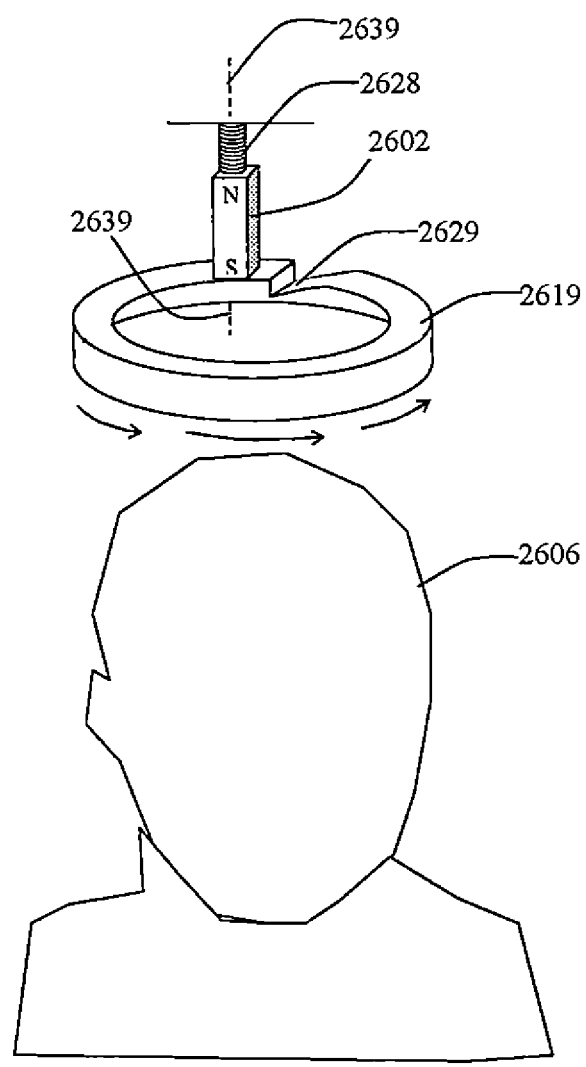
FIG. 26 shows an example embodiment of a NEST device having a single bar magnet that moves linearly along its north-south axis once each time the supporting ring is rotated, providing a pulse-type alternating magnetic field at the frequency of rotation.

FIG. 26 shows an example embodiment of a NEST device having a single bar magnet 2602 that moves linearly along its north-south axis 2639 once each time the supporting ring (or annulus) 2619 is rotated (rotation shown by arrows in FIG. 26), providing a pulse-type alternating magnetic field at the frequency of rotation. In this embodiment, a magnet 2602 is secured against a rotating ring (or annulus) 2619 with a spring 2628, where the ring 2619 has one or more detents 2629. The subject 2606 is shown below the ring 2619 in FIG. 26. When the ring 2619 is rotated, as shown with the arrows in FIG. 26, the magnet 2602 will be thrust into each detent 2629 once per rotation. As the ring 2619 continues to rotate, the magnet 2602 will move back to its original position. This periodic thrust may generate a more unipolar pulsatile magnetic field than that generated by a rotating magnet. The width and amplitude of the magnetic pulse depends on the mass and strength of the magnet, as well as the strength of the spring, and the depth of the detent.

In alternative embodiments to that shown in FIG. 26, there could be multiple detents in the ring. The ring could be non-circular. The magnet could rotate around the ring, while the ring is stationary. There could be multiple magnets and a single detent. There could be multiple magnets and multiple detents. Instead of a detent, the magnet or magnets could encounter a ridge, or multiple ridges. The magnet or magnets could encounter slopes, rather than sharp detents or ridges. The magnet could be positioned such that the north pole is closer to the treatment area than the south pole, or such that the south pole is closer to the treatment area than the north pole (such as is shown in FIG. 26). In some embodiments, the number of detents is the same as the number of magnets of the device. In some embodiments, the number of detents is not the same as the number of magnets of the device. In some embodiments, the number of detents is a multiple of the number of magnets of the device. In some embodiments, the number of detents is not a multiple of the number of magnets of the device.

In an alternative embodiments of the device, the magnet may flip (or rotate) about an axis between the north pole and south pole as a ring similar to that shown in FIG. 26 rotates. The magnet may be freely rotatable about the axis between the north pole and south pole, and the magnet may be rotatable about a shaft. The shaft, in this embodiment, is not coupled to a drive source. Rather, the ring itself may drive the flipping (rotating) of the magnet by capturing a first portion of the magnet in a first detent and moving that first portion as the ring moves until a second portion of the magnet is captured by second detent of the ring which likewise moves the second portion of the magnet. In some embodiments, the first portion is associated with a first pole of the magnet, and the second portion is associated with a second pole of the magnet. In one embodiment, the first pole may be the north pole of the magnet and the second pole may be the south pole of the magnet. In another embodiment, the first pole may be the south pole of the magnet and the second pole may be the north pole of the magnet. A drive source may drive the movement of the ring which, in turn, drives the rotation of the magnet. The drive source may be motor, for non-limiting example.

Example 14

Figure 31:
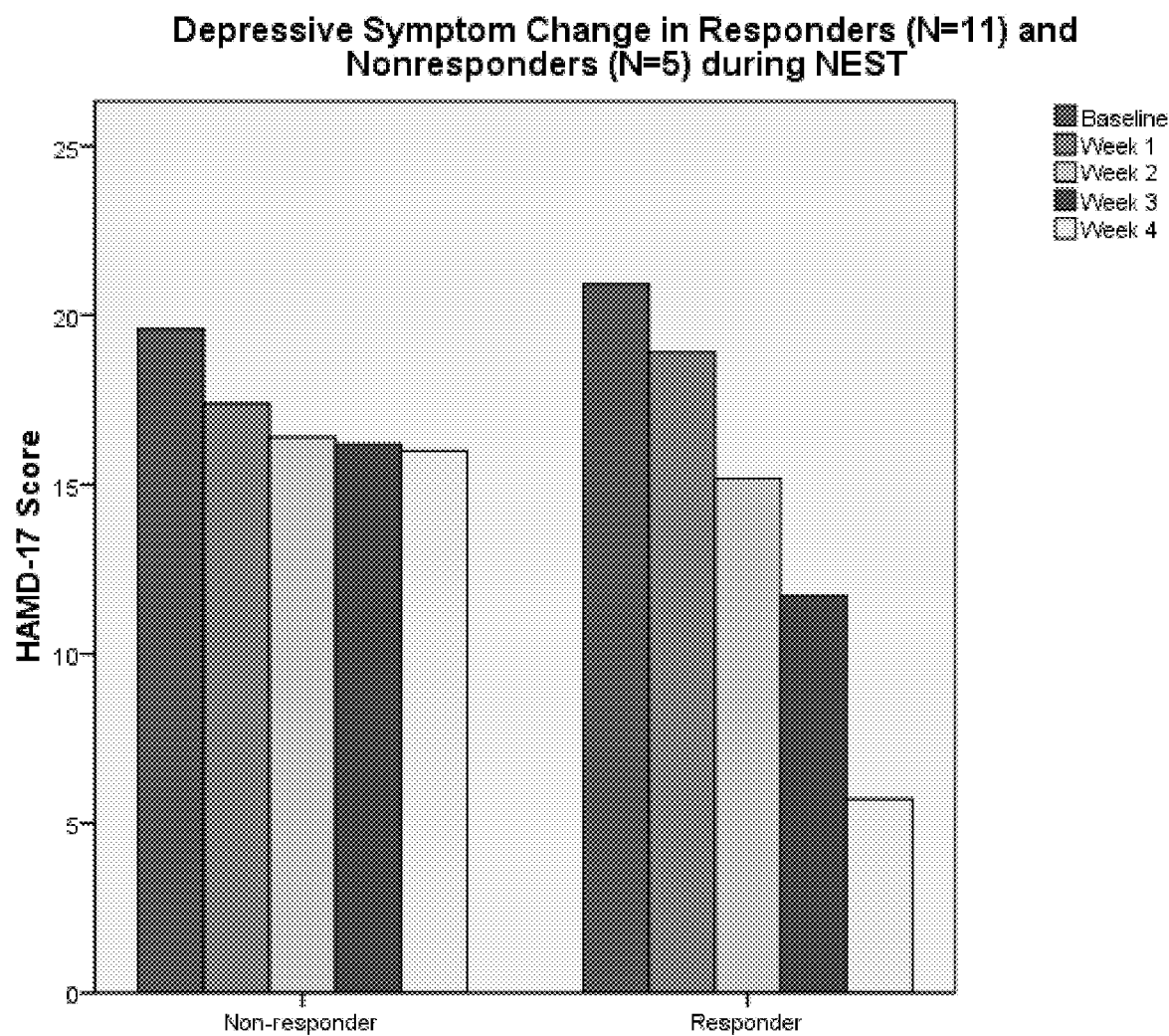
FIG. 31 is a comparison of change in the HAMD score of Responders versus Non-Responders.
Figure 32:
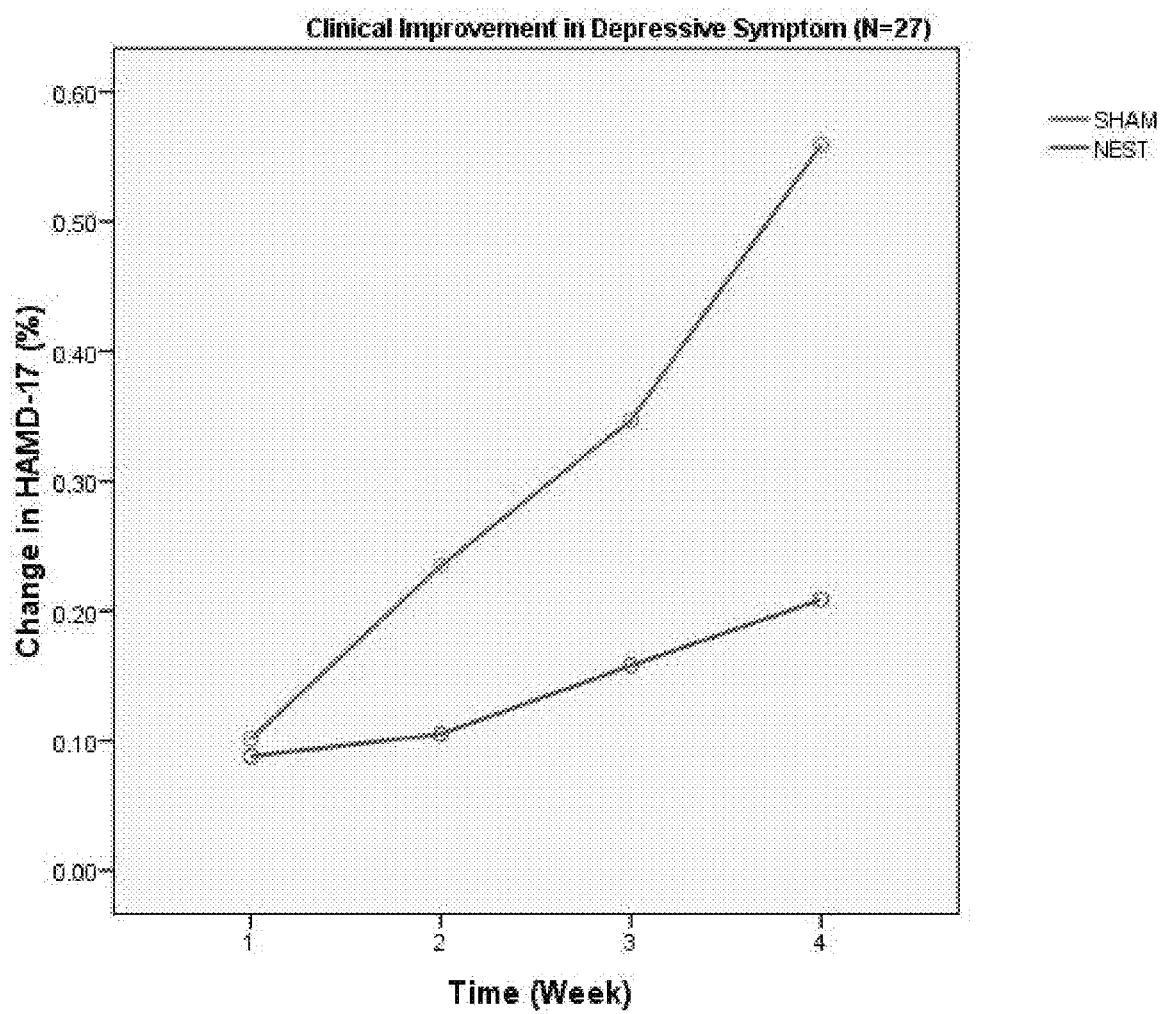
FIG. 32 is a comparison of the change in HAMD scores Subjects receiving NEST therapy versus Subjects receiving SHAM (i.e. control) therapy.

FIGS. 31 and 32 show the results of a clinical trial utilizing the NEST device and methods for the treatment of depression as provided herein. A device was used such as shown in FIG. 19, with permanent magnets arranged as shown in FIG. 16. In the method used in this trial, a magnetic field was adjusted to influence the Q-factor of an intrinsic frequency of each subject within the alpha-band. The magnetic field was applied close to the head of the subject. EEG readings were taken before treatment began. A Cadwell Easy 2.1 EEG system was used to take a 19-lead EEG reading. The intrinsic frequency in the alpha band (7-11 Hz) was determined using the initial EEG reading. Patients were placed in one of three groups: constant frequency, random frequency, or sham, with equal probability for each group. Patients received treatment every weekday for 30 days. EEG readings were taken after treatment at least on a weekly basis. If the patient was in the "constant frequency" group, the NEST was set to rotate the magnets at the intrinsic frequency. If the patient was in the "random frequency" group, the NEST was set to rotate the magnets at random frequencies between 6 Hz and 12 Hz, changing frequencies once per second. If the patient was in the "SHAM" group, the magnets in the NEST were replaced with steel cylinders, thereby imparting no magnetic field to a head of the patient. The patients in this group were divided into two subgroups with equal probability, with one group having the cylinders rotated at the intrinsic frequency and the other group having the cylinders rotated at random frequencies as noted above. For this clinical trial sixteen (16) subjects received treatment with the NEST device. Eleven (11) subjects responded to treatment (i.e. the Responders) and five (5) subjects did not respond to treatment (i.e. Non-Responders). Eleven (11) patients received treatment with the SHAM device.

FIG. 31 shows the percentage change in HAMD score in subjects being treated with the NEST device over the course of four (4) weeks. It is divided between subjects who responded to treatment (i.e. Responders) and subjects who did not respond to treatment (i.e. Non-Responders). Responders were classified as such when their HAMD scores decreased by 50% at least over the course of the four (4) weeks of treatment. The first bar is the average baseline HAMD score. Each subsequent bar represents the average HAMD score at the end of a week, weeks 1, 2, 3, and 4, left to right, respectively.

FIG. 32 shows the percentage change in HAMD score in subjects being treated with the NEST device versus the SHAM device over the course of four (4) weeks, as described in reference to FIG. 31 above. Baseline is not represented on the graph—it should be assumed to be 0.00. The first data point represents the average change after one (1) week of treatment. The second data point is the average change after two (2) weeks of treatment. The third data point is the average change after three (3) weeks of treatment. The fourth data point is the average change after four (4) weeks of treatment. The top line represents the average HAMD score for subjects treated with the NEST device, the bottom line represents the average HAMD score for subjects treated with the SHAM device.

Example 15

Figures 33, 34:
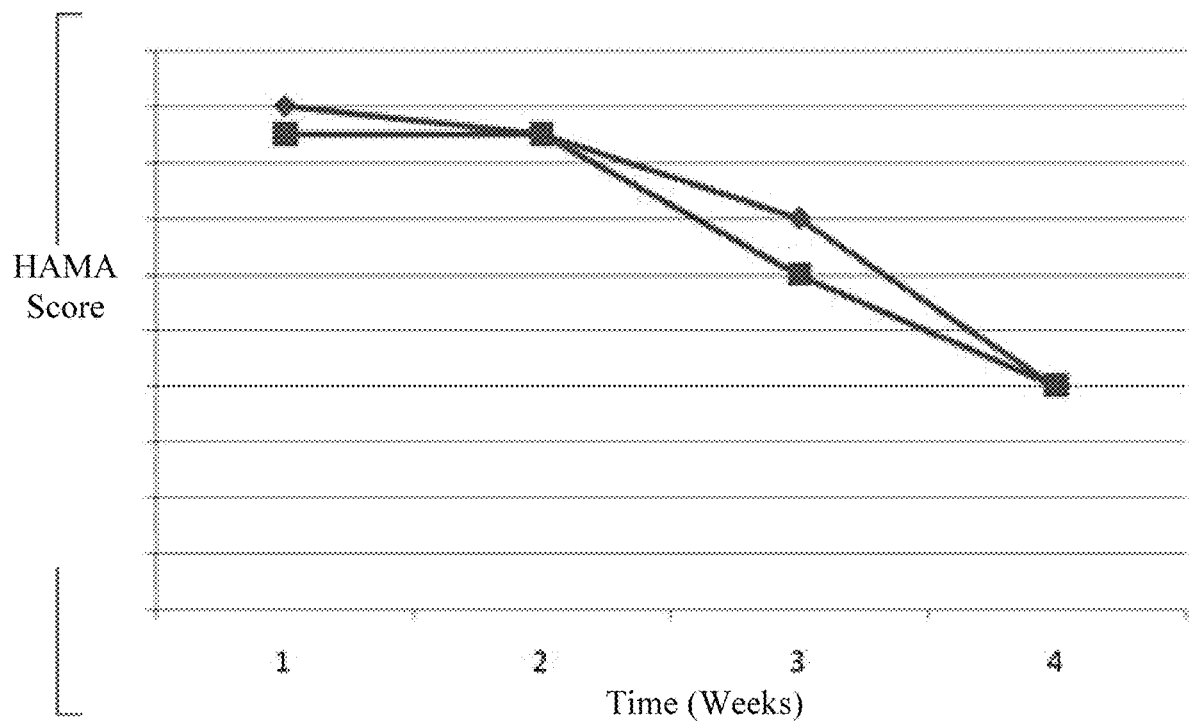
FIG. 33 shows the change in HAMA score of two patients over a period of three weeks.
FIG. 34 shows an equation that may be used to determine the fitted Gaussian curve A(f) of EEG data from a subject.

FIG. 33 shows the results of a clinical trial utilizing the NEST device for the treatment of anxiety. This trial involved two (2) patients (subjects). Both patients received treatment with the NEST device as shown in FIG. 19, with permanent magnets arranged as shown in FIG. 16. In the method used for these patients, a magnetic field was adjusted to influence the Q-factor of an intrinsic frequency of each subject within the alpha-band. The magnetic field was applied close to the head of the subject. EEG readings were taken before treatment began. A Cadwell Easy 2.1 EEG system was used to take a 19-lead EEG reading. The intrinsic frequency in the alpha band (7-11 Hz) was determined using the initial EEG reading. Both patients were treated with a constant frequency, wherein for each patient the NEST was set to rotate the magnets at the intrinsic frequency detected for that patient. Patients received treatment every weekday for 30 days. EEG readings were taken after treatment at least on a weekly basis. The first data point is the baseline HAMA score. The second data point for each line represents the HAMA score after one (1) week of treatment for each patient. The third data point for each line represents the HAMA score after two (2) weeks of treatment for each patient. The fourth data point for each line represents the HAMA score after four (4) weeks of treatment for each patient.

Example 16

Devices and methods are described herein for predicting efficacy of the NEST and related devices described herein. By reading the EEG output for a subject, the efficacy of the NEST device and/or related devices (e.g. TMS adjusted to affect the alpha frequency and/or Q-factor, etc. as noted elsewhere herein) may be predicted for treating the subject having a particular indication, disorder, symptom, dysfunction, and/or characteristic.

In one test, predicting the effect of magnetic therapy described herein on the subject is performed by providing EEG measurements for the subject; determining a subject's Q-factor in a specified EEG band; comparing the subject's Q-factor to a pre-selected Q-factor; if the subject's Q-factor is higher than the pre-selected Q-factor, providing a prediction that treatment with magnetic therapy that reduces the subject's Q-factor will improve at least one of: an indication in the subject, a disorder in the subject, a symptom in the subject, a dysfunction in the subject, and a characteristic in the subject. The magnetic therapy may include use of a device and/or process described elsewhere herein. The method may include measuring the electrical activity in the subject's brain (electroencephalography), as described elsewhere herein. The EEG measurements are measurements of brain activity of the subject while at rest with eyes closed in this test.

In some embodiments, the pre-selected Q-factor is at least one of: a Q-factor for a second subject who does not have the same indication, disorder, symptom, dysfunction and characteristic that the subject has; and a Q-factor for a healthy population of people not having the same indication, disorder, symptom, dysfunction and characteristic that the subject has, wherein the population comprises at least two people.

In another test, predicting the effect of magnetic therapy described herein on the subject is performed by providing EEG measurements for the subject; determining a subject's alpha-frequency in a specified EEG band; comparing the subject's alpha-frequency to a pre-selected alpha-frequency; if the subject's alpha-frequency is lower than the pre-selected alpha-frequency, providing a prediction that treatment with magnetic therapy that raises the subject's alpha-frequency will improve at least one of: an indication in the subject, a disorder in the subject, a symptom in the subject, a dysfunction in the subject, and a characteristic in the subject. The magnetic therapy may include use of a device and/or process described elsewhere herein. The method may include measuring the electrical activity in the subject's brain (electroencephalography), as described elsewhere herein. The EEG measurements are measurements of brain activity of the subject while at rest with eyes closed in this test.

In some embodiments, the pre-selected alpha-frequency is at least one of: an alpha-frequency for a second subject who does not have the same indication, disorder, symptom, dysfunction and characteristic that the subject has and an alpha-frequency for a healthy population of people not having the same indication, disorder, symptom, dysfunction and characteristic that the subject has, wherein the population comprises at least two people.

In some embodiments, the pre-selected alpha-frequency is about 9.0 Hz. As used herein, "about" with respect to alpha frequency includes variations of at least one of: 10%, 20%, 25%, 50%, 1 Hz, 0.5 Hz, 0.4 Hz, 0.3 hz, 0.2 Hz, and 0.1 Hz.

In yet another test, predicting the effect of magnetic therapy described herein on the subject is performed by providing EEG measurements for the subject; determining if the subject's EEG measurements exhibit a double hump comprising a peak in the theta band and a peak in the alpha band; if the subject's theta band does not have a double hump, providing a prediction that treatment with magnetic therapy that reduces the subject's Q-factor and/or shifts the subject's alpha band frequency, will improve at least one of: an indication in the subject, a disorder in the subject, a symptom in the subject, a dysfunction in the subject, and a characteristic in the subject. The magnetic therapy may include use of a device and/or process described elsewhere herein. The method may include measuring the electrical activity in the subject's brain (electroencephalography), as described elsewhere herein. The EEG measurements are measurements of brain activity of the subject while at rest with eyes closed in this test.

In some embodiments, the peak in the theta band exists if the subject's frequency domain EEG measurement has a peak that is at least about 10% higher than an affected population's theta band EEG measurement in the frequency domain, wherein the affected population comprises at least one person having the same indication, disorder, symptom, dysfunction and characteristic that the subject has. In some embodiments, the peak in the theta band exists if the subject's frequency domain EEG measurement has a peak that is at least about 25% higher than an affected population's theta band EEG measurement in the frequency domain. In some embodiments, the peak in the theta band exists if the subject's frequency domain EEG measurement has a peak that is at least about 40% higher than an affected population's theta band EEG measurement in the frequency domain. In some embodiments, the peak in the theta band exists if the subject's frequency domain EEG measurement has a peak that is at least about 50% higher than an affected population's theta band EEG measurement in the frequency domain. As used herein, "about" with respect to theta band peak differences between the subject and the affected population includes variations of at least one of: 1%, 5%, 10%, 20%, 25%, 30%, 40%, 50%, 60%, and 75% (e.g. a peak that is 10% higher than the affected population's peak may vary 10% of 10%, or 1%, or be from 9%-11% higher and still be considered to be about 10% higher).

In some embodiments, the peak in the theta band exists if the subject's frequency domain EEG measurement has a peak that is at least about 10% higher than a normal population's theta band EEG measurement in the frequency domain, wherein the normal population comprises at least one person not having the same indication, disorder, symptom, dysfunction and characteristic that the subject has. In some embodiments, the peak in the theta band exists if the subject's frequency domain EEG measurement has a peak that is at least about 25% higher than normal population's theta band EEG measurement in the frequency domain. In some embodiments, the peak in the theta band exists if the subject's frequency domain EEG measurement has a peak that is at least about 40% higher than normal population's theta band EEG measurement in the frequency domain. In some embodiments, the peak in the theta band exists if the subject's frequency domain EEG measurement has a peak that is at least about 50% higher than normal population's theta band EEG measurement in the frequency domain. As used herein, "about" with respect to theta band peak differences between the subject and the normal population includes variations of at least one of: 1%, 5%, 10%, 20%, 25%, 30%, 40%, 50%, 60%, and 75% (e.g. a peak that is 10% higher than the affected population's peak may vary 10% of 10%, or 1%, or be from 9%-11% higher and still be considered to be about 10% higher).

In yet another test, predicting the effect of magnetic therapy described herein on the subject is performed by providing EEG measurements for the subject; determining if the subject's EEG measurements exhibit a high power beta band; if the subject's EG measurements do not exhibit a high power beta band, providing a prediction that treatment with magnetic therapy that reduces the subject's Q-factor and/or shifts the subject's alpha band frequency, will improve at least one of: an indication in the subject, a disorder in the subject, a symptom in the subject, a dysfunction in the subject, and a characteristic in the subject. The magnetic therapy may include use of a device and/or process described elsewhere herein. The method may include measuring the electrical activity in the subject's brain (electroencephalography), as described elsewhere herein. The EEG measurements are measurements of brain activity of the subject while at rest with eyes closed in this test.

In some embodiments, the subject's EEG measurements exhibit a high power beta band if the subject's beta band power is at least about 10% higher than an affected population's beta band power, wherein the affected population comprises at least one person having the same indication, disorder, symptom, dysfunction and characteristic that the subject has. In some embodiments, the subject's beta band power is at least about 25% higher than an affected population's beta band power. In some embodiments, the subject's beta band power is at least about 40% higher than an affected population's beta band power. In some embodiments, the subject's beta band power is at least about 50% higher than an affected population's beta band power. As used herein, "about" with respect to beta band power differences between the subject and the affected population includes variations of at least one of: 1%, 5%, 10%, 20%, 25%, 30%, 40%, 50%, 60%, and 75% (e.g. a peak that is 10% higher than the affected population's band power may vary 10% of 10%, or 1%, or be from 9%-11% higher and still be considered to be about 10% higher).

In some embodiments, the subject's EEG measurements exhibit a high power beta band if the subject's beta band power is at least about 10% higher than a normal population's beta band power, wherein the normal population comprises at least one person not having the same indication, disorder, symptom, dysfunction and characteristic that the subject has. In some embodiments, the subject's beta band power is at least about 25% higher than normal population's beta band power. In some embodiments, the subject's beta band power is at least about 40% higher than normal population's beta band power. In some embodiments, the subject's beta band power is at least about 50% higher than normal population's beta band power. As used herein, "about" with respect to beta band power differences between the subject and the normal population includes variations of at least one of: 1%, 5%, 10%, 20%, 25%, 30%, 40%, 50%, 60%, and 75% (e.g. a peak that is 10% higher than the affected population's band power may vary 10% of 10%, or 1%, or be from 9%-11% higher and still be considered to be about 10% higher).

In some embodiments, the indication comprises at least one of: replacement for meditation, quick nap, stress release, attention span, comprehension, memory, lowered blood pressure, increased libido, sports performance, academic performance, increased blood flow, lowered blood flow, increased metabolism, and a lowered metabolism.

In some embodiments, the disorder is depression.

In some embodiments, the disorder comprises at least one of: bipolar, anxiety, obsessive-compulsive, seizure, Parkinson's disease, ADHD, autism, substance abuse, head injury, Alzheimer's disease, eating disorder, sleep disorder, tinnitus, and fibromyalgia.

In some embodiments, the disorder is a neurologic disorder.

In some embodiments, the symptom is neuropathic pain.

In some embodiments, the symptom is psychogenic pain.

In some embodiments, the symptom is a brain damage symptom.

In some embodiments, the dysfunction is a brain dysfunction.

In some embodiments, the characteristic is at least one of: peripheral visual response, attention span, immediate reaction time (IRT), movement time (MT), simple perceptual reaction time (SPR), and conflict perceptual reaction time (CPR).

As used herein, providing the EEG measurements may or may not comprise generating EEG measurements, depending on the embodiment. In some embodiments, the EEG measurements may be generated at another time, and generating the EEG measurements is not part of the process claimed. In other embodiments, providing the EEG measurements comprises generating EEG measurements.

In yet another test, predicting the effect of magnetic therapy described herein on the subject is performed using a device comprising: a receiving element that receives EEG measurements for the subject; logic that determines a subject's Q-factor in a specified EEG band; logic that compares the subject's Q-factor to a pre-selected Q-factor; and logic that, if the subject's Q-factor is higher than the pre-selected Q-factor, provides a prediction that treatment with magnetic therapy that reduces the subject's Q-factor will improve at least one of: an indication in the subject, a disorder in the subject, a symptom in the subject, a dysfunction in the subject, and a characteristic in the subject. The magnetic therapy may include use of a device and/or process described elsewhere herein. The receiving element may itself measure the electrical activity in the subject's brain (electroencephalography), as described elsewhere herein. The EEG measurements are measurements of brain activity of the subject while at rest with eyes closed in this test.

In some embodiments, the pre-selected Q-factor is at least one of: a Q-factor for a second subject who does not have the same indication, disorder, symptom, dysfunction and characteristic that the subject has, and a Q-factor for a healthy population of people not having the same indication, disorder, symptom, dysfunction and characteristic that the subject has, wherein the population comprises at least two people. The magnetic therapy may include use of a device and/or process described elsewhere herein.

In yet another test, predicting the effect of magnetic therapy described herein on the subject is performed using a device comprising: a receiving element that receives EEG measurements for the subject; logic that determines a subject's alpha-frequency in a specified EEG band; logic that compares the subject's alpha-frequency to a pre-selected alpha-frequency; logic that, if the subject's alpha-frequency is lower than the pre-selected alpha-frequency, provides a prediction that treatment with magnetic therapy that raises the subject's alpha-frequency will improve at least one of: an indication in the subject, a disorder in the subject, a symptom in the subject, a dysfunction in the subject, and a characteristic in the subject. The magnetic therapy may include use of a device and/or process described elsewhere herein. The receiving element may itself measure the electrical activity in the subject's brain (electroencephalography), as described elsewhere herein. The EEG measurements are measurements of brain activity of the subject while at rest with eyes closed in this test.

In some embodiments, the pre-selected alpha-frequency is at least one of: an alpha-frequency for a second subject who does not have the same indication, disorder, symptom, dysfunction and characteristic that the subject has, and an alpha-frequency for a healthy population of people not having the same indication, disorder, symptom, dysfunction and characteristic that the subject has, wherein the population comprises at least two people.

In some embodiments, the pre-selected alpha-frequency is about 9.0 Hz. As used herein, "about" with respect to alpha frequency includes variations of at least one of: 10%, 20%, 25%, 50%, 1 Hz, 0.5 Hz, 0.4 Hz, 0.3 hz, 0.2 Hz, and 0.1 Hz.

In yet another test, predicting the effect of magnetic therapy described herein on the subject is performed using a device comprising a receiving element that receives EEG measurements for the subject; logic that determines if the subject's EEG measurements exhibit a double hump comprising a peak in the theta band and a peak in the alpha band; logic that, if the subject's theta band does not have a double hump, provides a prediction that treatment with magnetic therapy that reduces the subject's Q-factor and/or shifts the subject's alpha band frequency, will improve at least one of: an indication in the subject, a disorder in the subject, a symptom in the subject, a dysfunction in the subject, and a characteristic in the subject. The magnetic therapy may include use of a device and/or process described elsewhere herein. The receiving element may itself measure the electrical activity in the subject's brain (electroencephalography), as described elsewhere herein. The EEG measurements are measurements of brain activity of the subject while at rest with eyes closed in this test.

In some embodiments, the peak in the theta band exists if the subject's frequency domain EEG measurement has a peak that is at least about 10% higher than an affected population's theta band EEG measurement in the frequency domain, wherein the affected population comprises at least one person having the same indication, disorder, symptom, dysfunction and characteristic that the subject has. In some embodiments, the peak in the theta band exists if the subject's frequency domain EEG measurement has a peak that is at least about 25% higher than an affected population's theta band EEG measurement in the frequency domain. In some embodiments, the peak in the theta band exists if the subject's frequency domain EEG measurement has a peak that is at least about 40% higher than an affected population's theta band EEG measurement in the frequency domain. In some embodiments, the peak in the theta band exists if the subject's frequency domain EEG measurement has a peak that is at least about 50% higher than an affected population's theta band EEG measurement in the frequency domain. As used herein, "about" with respect to theta band peak differences between the subject and the affected population includes variations of at least one of: 1%, 5%, 10%, 20%, 25%, 30%, 40%, 50%, 60%, and 75% (e.g. a peak that is 10% higher than the affected population's peak may vary 10% of 10%, or 1%, or be from 9%-11% higher and still be considered to be about 10% higher).

In some embodiments, the peak in the theta band exists if the subject's frequency domain EEG measurement has a peak that is at least about 10% higher than a normal population's theta band EEG measurement in the frequency domain, wherein the normal population comprises at least one person not having the same indication, disorder, symptom, dysfunction and characteristic that the subject has. In some embodiments, the peak in the theta band exists if the subject's frequency domain EEG measurement has a peak that is at least about 25% higher than normal population's theta band EEG measurement in the frequency domain. In some embodiments, the peak in the theta band exists if the subject's frequency domain EEG measurement has a peak that is at least about 40% higher than normal population's theta band EEG measurement in the frequency domain. In some embodiments, the peak in the theta band exists if the subject's frequency domain EEG measurement has a peak that is at least about 50% higher than normal population's theta band EEG measurement in the frequency domain. As used herein, "about" with respect to theta band peak differences between the subject and the normal population includes variations of at least one of: 1%, 5%, 10%, 20%, 25%, 30%, 40%, 50%, 60%, and 75% (e.g. a peak that is 10% higher than the affected population's peak may vary 10% of 10%, or 1%, or be from 9%-11% higher and still be considered to be about 10% higher).

In yet another test, predicting the effect of magnetic therapy described herein on the subject is performed using a device comprising a receiving element that receives EEG measurements for the subject; logic that determines if the subject's EEG measurements exhibit a high power beta band; logic that, if the subject's EG measurements do not exhibit a high power beta band, provide a prediction that treatment with magnetic therapy that reduces the subject's Q-factor and/or shifts the subject's alpha band frequency, will improve at least one of: an indication in the subject, a disorder in the subject, a symptom in the subject, a dysfunction in the subject, and a characteristic in the subject. The magnetic therapy may include use of a device and/or process described elsewhere herein. The receiving element may itself measure the electrical activity in the subject's brain (electroencephalography), as described elsewhere herein. The EEG measurements are measurements of brain activity of the subject while at rest with eyes closed in this test.

In some embodiments, the subject's EEG measurements exhibit a high power beta band if the subject's beta band power is at least about 10% higher than an affected population's beta band power, wherein the affected population comprises at least one person having the same indication, disorder, symptom, dysfunction and characteristic that the subject has. In some embodiments, the subject's beta band power is at least about 25% higher than an affected population's beta band power. In some embodiments, the subject's beta band power is at least about 40% higher than an affected population's beta band power. In some embodiments, the subject's beta band power is at least about 50% higher than an affected population's beta band power. As used herein, "about" with respect to beta band power differences between the subject and the affected population includes variations of at least one of: 1%, 5%, 10%, 20%, 25%, 30%, 40%, 50%, 60%, and 75% (e.g. a peak that is 10% higher than the affected population's band power may vary 10% of 10%, or 1%, or be from 9%-11% higher and still be considered to be about 10% higher).

In some embodiments, the subject's EEG measurements exhibit a high power beta band if the subject's beta band power is at least about 10% higher than a normal population's beta band power, wherein the normal population comprises at least one person not having the same indication, disorder, symptom, dysfunction and characteristic that the subject has. In some embodiments, the subject's beta band power is at least about 25% higher than normal population's beta band power. In some embodiments, the subject's beta band power is at least about 40% higher than normal population's beta band power. In some embodiments, the subject's beta band power is at least about 50% higher than normal population's beta band power. As used herein, "about" with respect to beta band power differences between the subject and the normal population includes variations of at least one of: 1%, 5%, 10%, 20%, 25%, 30%, 40%, 50%, 60%, and 75% (e.g. a peak that is 10% higher than the affected population's band power may vary 10% of 10%, or 1%, or be from 9%-11% higher and still be considered to be about 10% higher).

In some embodiments, the indication comprises at least one of: replacement for meditation, quick nap, stress release, attention span, comprehension, memory, lowered blood pressure, increased libido, sports performance, academic performance, increased blood flow, lowered blood flow, increased metabolism, and a lowered metabolism.

In some embodiments, the disorder is depression.

In some embodiments, the disorder comprises at least one of: bipolar, anxiety, obsessive-compulsive, seizure, Parkinson's disease, ADHD, autism, substance abuse, head injury, Alzheimer's disease, eating disorder, sleep disorder, tinnitus, and fibromyalgia.

In some embodiments, the disorder is a neurologic disorder.

In some embodiments, the symptom is neuropathic pain.

In some embodiments, the symptom is psychogenic pain.

In some embodiments, the symptom is a brain damage symptom.

In some embodiments, the dysfunction is a brain dysfunction.

In some embodiments, the characteristic is at least one of: peripheral visual response, attention span, immediate reaction time (IRT), movement time (MT), simple perceptual reaction time (SPR), and conflict perceptual reaction time (CPR).

In some embodiments, the device for predicting efficacy of magnetic therapy is called an efficacy prediction device. In some embodiments, the efficacy prediction device is built into a magnetic therapy device, for non-limiting example, a NEST device.

As used herein, the EEG measurements may or may not be generated by a separate EEG device and downloaded from a saved format (e.g. a file saved in any manner which can be received and processed as described) or directly transferred without being otherwise saved from that separate EEG device, depending on the embodiment. In some embodiments, the EEG measurements may be generated by a separate device, an EEG device for example, and saved. In other embodiments, the EEG measurements may be generated by the efficacy prediction device itself and received by the receiving element within the efficacy prediction device.

Example 17

A test may be run utilizing the NEST device for the treatment of depression or any disorder, indication, symptom, dysfunction, and/or characteristic noted herein. The patient may receive treatment with the NEST device as shown in FIG. 19, with permanent magnets arranged as shown in FIG. 16. In the method used for these patients, a magnetic field may be adjusted to influence the Q-factor of an intrinsic frequency of each subject within the alpha-band, and/or to influence the alpha frequency of the patient's brain. The test may be run in the morning to improve results. The magnetic field may be applied close to the head of the subject. EEG readings may be taken before treatment began. A Cadwell Easy 2.1 EEG system may be used to take a 19-lead EEG reading. The intrinsic frequency in the alpha band (7-11 Hz) may be determined using the initial EEG reading. Patients may be treated with a constant frequency, wherein for each patient the NEST may be set to rotate the magnets at the intrinsic frequency detected for that patient. Patients may, in the alternative, be treated with a frequency selection (hopping, constant higher, or constant lower, or other), as noted elsewhere herein. The patient may receive treatment every weekday for a week minimum, or for as few as one day. EEG readings may be taken after treatment at least on a weekly basis or after each treatment. Improvements in the patient's disorder, indication, symptom, dysfunction, and/or characteristic may be shown.

The various functions or processes disclosed herein (such as, for non-limiting example, logic that performs a function or process) may be described as data and/or instructions embodied in various computer-readable media, in terms of their behavioral, register transfer, logic component, transistor, layout geometries, and/or other characteristics. The logic described herein may comprise, according to various embodiments of the invention, software, hardware, or a combination of software and hardware adjusted and adapted to perform the particular function or process. The logic described herein may comprise computer-readable media, Computer-readable media in which such formatted data and/or instructions may be embodied include, but are not limited to, non-volatile storage media in various forms (e.g., optical, magnetic or semiconductor storage media) and carrier waves that may be used to transfer such formatted data and/or instructions through wireless, optical, or wired signaling media or any combination thereof. Examples of transfers of such formatted data and/or instructions by carrier waves include, but are not limited to, transfers (uploads, downloads, e-mail, etc.) over the Internet and/or other computer networks via one or more data transfer protocols (e.g., HTTP, FTP, SMTP, etc.). When received within a computer system via one or more computer-readable media, such data and/or instruction-based expressions of components and/or processes under the ICS may be processed by a processing entity (e.g., one or more processors) within the computer system in conjunction with execution of one or more other computer programs.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

The above descriptions of illustrated embodiments of the system, methods, or devices are not intended to be exhaustive or to be limited to the precise form disclosed. While specific embodiments of, and examples for, the system, methods, or devices are described herein for illustrative purposes, various equivalent modifications are possible within the scope of the system, methods, or devices, as those skilled in the relevant art will recognize. The teachings of the system, methods, or devices provided herein can be applied to other processing systems, methods, or devices, not only for the systems, methods, or devices described.

The elements and acts of the various embodiments described can be combined to provide further embodiments. These and other changes can be made to the system in light of the above detailed description.

In general, in the following claims, the terms used should not be construed to limit the system, methods, or devices to the specific embodiments disclosed in the specification and the claims, but should be construed to include all processing systems that operate under the claims. Accordingly, the system, methods, and devices are not limited by the disclosure, but instead the scopes of the system, methods, or devices are to be determined entirely by the claims.

While certain aspects of the system, methods, or devices are presented below in certain claim forms, the inventors contemplate the various aspects of the system, methods, or devices in any number of claim forms. For example, while only one aspect of the system, methods, or devices is recited as embodied in machine-readable medium, other aspects may likewise be embodied in machine-readable medium. Accordingly, the inventors reserve the right to add additional claims after filing the application to pursue such additional claim forms for other aspects of the system, methods, or devices.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A device for applying a varying magnetic field to a head of a subject, the device being configured to receive at least a portion of the head of the subject, and comprising:
   a) a first permanent magnet;
   b) a helmet with the first permanent magnet therein, the helmet configured to receive the portion of the head of the subject; and
   c) a second permanent magnet; and
   d) a controller subunit configured to generate a time varying magnetic field by controlling rotation of the first permanent magnet, the rotation being relative about an axis parallel to at least a portion of the head and being at a harmonic frequency of a frequency within a specific EEG band.

2. The device of claim 1, wherein the specified EEG band is an Alpha band, a Beta band, or a Theta band.

3. The device of claim 1, wherein the controller subunit is coupled to the second permanent magnet and operable to rotate the second permanent magnet about a second axis that is parallel to the axis, and wherein the varying magnetic field treats drug addiction or substance abuse.

4. The device of claim 3, wherein the controller subunit is operable to control rotation of the second permanent magnet to be at the frequency within the specific EEG band.

5. The device of claim 4, wherein the specified EEG band is an Alpha band, a Beta band, or a Theta band.

6. A device for applying a varying magnetic field to a head of a subject, the device being configured to receive at least a portion of the head of the subject, and comprising:
   a) a first permanent magnet;
   b) a controller operable to control rotation of the first permanent magnet, the rotation being relative about an axis parallel to at least a portion of the head and being at a harmonic frequency of a frequency within a specific EEG band, thereby generating a varying magnetic field; and
   c) a subunit configured to determine an intrinsic frequency of the subject within the specified EEG band or receive the intrinsic frequency of the subject within the specified EEG band.

7. The device of claim 6, wherein the harmonic frequency of the frequency within the specific EEG band is based on the intrinsic frequency of the subject within the specified EEG band or a harmonic frequency of the intrinsic frequency of the subject.

8. The device of claim 7, wherein the harmonic frequency of the frequency within the specific EEG band is higher than the intrinsic frequency of the subject within the specified EEG band or the harmonic frequency of the intrinsic frequency of the subject.

9. The device of claim 7, wherein the harmonic frequency of the frequency within the specific EEG band is lower than the intrinsic frequency of the subject within the specified EEG band or the harmonic frequency of the intrinsic frequency of the subject.

10. A device for applying a varying magnetic field to a head of a subject, the device being configured to receive at least a portion of the head of the subject, and comprising:
    a) a permanent magnet;
    b) a helmet with the permanent magnet therein that is configured to receive the portion of the head of the subject;
    c) a second permanent magnet; and
    d) a controller subunit configured to generate a time varying magnetic field by controlling rotation of the permanent magnet, the rotation being relative about an axis parallel to at least a portion of the head and being at a frequency based on an intrinsic frequency of the subject within a specified EEG band or a harmonic frequency of the intrinsic frequency of the subject.

11. The device of claim 10, wherein the controller subunit is operable to control rotation of the permanent magnet to be at a frequency within the specified EEG band.

12. The device of claim 11, wherein the specified EEG band is an Alpha band, a Beta band, or a Theta band.

13. The device of claim 10, wherein the controller subunit is operable to control rotation of the second permanent magnet to be at a frequency within the specified EEG band, and wherein the varying magnetic field treats drug addiction or substance abuse.

14. The device of claim 10, wherein the specified EEG band is an Alpha band, a Beta band, or a Theta band.

15. The device of claim 10, wherein the controller subunit is coupled to the second permanent magnet and operable to rotate the second permanent magnet about a second axis that is parallel to the axis, and wherein the varying magnetic field treats drug addiction or substance abuse.

16. A device for applying a varying magnetic field to a head of a subject the device being configured to receive at least a portion of the head of the subject and comprising:
   a) a permanent magnet;
   b) a controller operable to control rotation of the permanent magnet, the rotation being relative about an axis parallel to at least a portion of the head and being at a frequency based on an intrinsic frequency of the subject within a specified EEG band or a harmonic frequency of the intrinsic frequency of the subject thereby generating a varying magnetic field; and
   c) a subunit configured to determine the intrinsic frequency of the subject within the specified EEG band or receive the intrinsic frequency of the subject within the specified EEG band.

17. The device of claim 16, wherein the frequency within the specific EEG band or the harmonic frequency of the frequency within the specific EEG band is higher than the intrinsic frequency of the subject within the specified EEG band or the harmonic frequency of the intrinsic frequency of the subject.

18. The device of claim 16, wherein the frequency within the specific EEG band or the harmonic frequency of the frequency within the specific EEG band is lower than the intrinsic frequency of the subject within the specified EEG band or the harmonic frequency of the intrinsic frequency of the subject.

19. A method for applying a varying magnetic field to a head of a subject, the method comprising: providing a device for treating drug addiction or substance abuse of the subject comprising:
   a) providing a permanent magnet;
   b) providing a helmet with the permanent magnet therein, that receives a portion of the head of the subject;
   c) providing a second permanent magnet; and
   d) providing a controller subunit operable to control rotation of the permanent magnet, the rotation being relative about a first axis parallel to at least a portion of the head and being at a harmonic frequency of a frequency within a specific EEG band, thereby generating a varying magnetic field, wherein the varying magnetic field treats drug addiction or substance abuse.

20. The device of claim 19, wherein the specified EEG band is an Alpha band, a Beta band, or a Theta band.

21. The device of claim 19, further comprising, coupling the controller subunit to the second permanent magnet so that the controller subunit is operable to rotate the second permanent magnet about a second axis that is parallel to the first axis.

22. The device of claim 21, wherein the controller subunit is operable to control rotation of the second permanent magnet to be at the frequency within the specific EEG band.

23. The device of claim 22, wherein the specified EEG band is an Alpha band, a Beta band, or a Theta band.

24. A method for applying a varying magnetic field to a head of a subject the method comprising: providing a device for treating drug addiction or substance abuse of the subject comprising:
   a) providing a permanent magnet:
   b) providing a controller operable to control rotation of the permanent magnet, the rotation being relative about a first axis parallel to at least a portion of the head and being at a harmonic frequency of a frequency within a specific EEG band, thereby generating a varying magnetic field, wherein the varying magnetic field treats drug addiction or substance abuse; and
   c) providing a subunit configured to determine an intrinsic frequency of the subject within the specified EEG band or receive the intrinsic frequency of the subject within the specified EEG band.

25. The device of claim 24, wherein the frequency within the specific EEG band or the harmonic frequency of the frequency within the specific EEG band is based on the intrinsic frequency of the subject within the specified EEG band, or a harmonic frequency of the intrinsic frequency of the subject.

26. The device of claim 25, wherein the frequency within the specific EEG band or the harmonic frequency of the frequency within the specific EEG band, is higher than the intrinsic frequency of the subject within the specified EEG band or the harmonic frequency of the intrinsic frequency of the subject.

27. The device of claim 25, wherein the frequency within the specific EEG band or the harmonic frequency of the frequency within the specific EEG band is lower than the intrinsic frequency of the subject within the specified EEG band or the harmonic frequency of the intrinsic frequency of the subject.

* * * * *